United States Patent
Zimmermann et al.

(10) Patent No.: US 7,091,346 B1
(45) Date of Patent: Aug. 15, 2006

(54) PURINE DERIVATIVES AND PROCESSES FOR THEIR PREPARATION

(75) Inventors: Jürg Zimmermann, Wallbach (CH); Hans-Georg Capraro, Rheinfelden (CH); Patricia Imbach, Riehen (CH); Pascal Furet, Thann (FR)

(73) Assignee: Novartis AG, Basel (CH)

( * ) Notice: Subject to any disclaimer, the term of this patent is extended or adjusted under 35 U.S.C. 154(b) by 1481 days.

(21) Appl. No.: 09/051,827

(22) PCT Filed: Oct. 22, 1996

(86) PCT No.: PCT/EP96/04573

§ 371 (c)(1),
(2), (4) Date: May 1, 1998

(87) PCT Pub. No.: WO97/16452

PCT Pub. Date: May 9, 1997

(30) Foreign Application Priority Data

Nov. 1, 1995 (CH) .................... 3094/95
Sep. 10, 1996 (CH) .................... 2213/96

(51) Int. Cl.
C07D 473/40 (2006.01)
C07D 473/16 (2006.01)
A61K 31/52 (2006.01)
A61P 35/00 (2006.01)
A61P 17/06 (2006.01)

(52) U.S. Cl. .................................... 544/277
(58) Field of Classification Search ................ 544/277; 514/261, 266
See application file for complete search history.

(56) References Cited

U.S. PATENT DOCUMENTS

| | | | |
|---|---|---|---|
| 4,853,386 A | 8/1989 | Friebe et al. | 514/266 |
| 5,663,154 A * | 9/1997 | Burns et al. | 514/45 |
| 5,866,702 A * | 2/1999 | Mackman et al. | 544/277 |
| 6,767,906 B1 * | 7/2004 | Imbach et al. | 514/234.2 |
| 2003/0191312 A1 * | 10/2003 | Ding et al. | 544/235 |
| 2004/0157864 A1 * | 8/2004 | Wu et al. | 514/263.37 |

FOREIGN PATENT DOCUMENTS

| | | |
|---|---|---|
| EP | 212 535 | 3/1987 |
| EP | 773 023 A1 | 5/1997 |
| WO | WO 90/09178 | 8/1990 |
| WO | WO 97/20842 | 6/1997 |
| WO | WO 97 35539 | 10/1997 |
| WO | WO 98/05335 | 2/1998 |
| WO | WO 98 07725 | 2/1998 |
| WO | WO 98/16528 | 4/1998 |

OTHER PUBLICATIONS

Bioorganic & Med. Chem. Letters, vol. 7, No. 21, pp. 2697-2702 (1997).

* cited by examiner

*Primary Examiner*—Mark L. Berch
(74) *Attorney, Agent, or Firm*—Lydia T. McNally

(57) ABSTRACT

2-Amino-6-anilino-purine derivatives of the formula 1

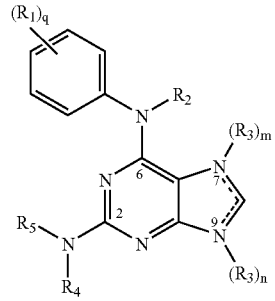

(I)

in which the symbols are as defined in claim 1 are described.

These compounds inhibit $p34^{cdc2}$/cyclin $B^{cdc13}$ kinase and can be used for treatment of hyperproliferative diseases, for example tumour diseases.

1 Claim, No Drawings

PURINE DERIVATIVES AND PROCESSES FOR THEIR PREPARATION

The invention relates to 2-amino-6-anilino-purine derivatives and to processes and novel intermediates for their preparation, pharmaceutical formulations which comprise such derivatives, and the use of these derivatives as medicaments.

The invention relates to 2-amino-6-anilino-purine derivatives of the formula I

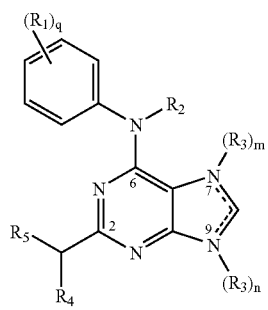

in which q is 1–5, $R_1$ is halogen, lower alkyl, hydroxyl or lower alkanoyloxy; lower alkoxy which is unsubstituted or substituted by hydroxyl, lower alkoxy or carboxyl; a radical of the formula —O(—CH$_2$—CH$_2$—O)$_t$—R$_6$, in which t is 2–5 and $R_6$ is hydrogen or lower alkyl; carboxyl, lower alkoxycarbonyl, piperazin-1-yl-carbonyl or carbamoyl; N-lower alkyl-carbamoyl, which is unsubstituted or substituted by hydroxyl or amino in the lower alkyl moiety; N,N-di-lower alkyl-carbamoyl, cyano, nitro, amino, lower alkanoyl amino, lower alkylamino, N,N-di-lower alkylamino, aminosulfonyl or trifluoromethyl, where, if more than one radical R is present in the molecule, these can be identical to or different from one another, $R_2$ is hydrogen, carbamoyl or N-lower alkyl-carbamoyl, m and n are each 0 or 1, where m is 0 if n is 1 and m is 1 if n is 0, $R_3$ is lower alkyl or phenyl which are unsubstituted or in each case substituted by hydroxyl, lower alkoxy, amino, lower alkylamino or N,N-di-lower alkyl amino, and a) $R_4$ is hydrogen, amino, phenylamino, lower alkylamino, hydroxyl, phenoxy, lower alkoxy, acyl having 1–30 C atoms, a substituted aliphatic hydrocarbon radical having not more than 29 C atoms, a substituted carbocyclic radical having not more than 29 C atoms or a substituted heterocyclic radical having not more than 20 C atoms and not more than 9 heteroatoms and $R_5$ is amino, phenylamino, lower alkylamino, hydroxyl, phenoxy, lower alkoxy, acyl having 2–30 C atoms, a substituted aliphatic hydrocarbon radical having not more than 29 C atoms, a carbocyclic radical having not more than 29 C atoms or a heterocyclic radical having not more than 20 C atoms and not more than 9 heteroatoms, or b) $R_4$ and $R_5$ together are a substituted or unsubstituted alkylene or alkenylene radical having in each case not more than 15 C atoms, in which 1–3 C atoms can be replaced by oxygen, sulfur or nitrogen, and their salts.

Formula I encompasses the formulae Ia and Ib derived from the corresponding tautomeric purine derivatives, in which the symbols are as defined above.

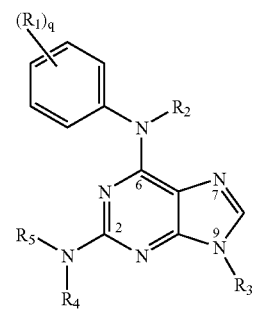

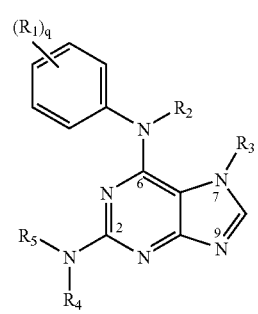

Unless stated otherwise, in the present disclosure organic radicals designated "lower" contain not more than 7, preferably not more than 4, carbon atoms.

q is preferably 1–3, as a rule 1 or 2, preferably 1. Only if it is possible for steric reasons, can q also be 4 or 5, for example if $R_1$ is fluorine. If q is 1, $R_1$ is, for example, in the 4 position or, preferably, in the 3 position.

Halogen $R_1$ is, for example, fluorine or, preferably, chlorine.

Lower alkoxy $R_1$ is, for example, methoxy.

N-Lower alkyl-carbamoyl $R_1$ which is substituted by hydroxyl in the lower alkyl part is, for example, (3-hydroxypropyl-amino)-carbonyl, i.e. N-(3-hydroxy-propyl)-carbamoyl.

$R_2$ is preferably hydrogen.

Preferably, m is 0 and n is 1.

$R_3$ is preferably lower alkyl which is unsubstituted or substituted by hydroxyl, such as methyl, isopropyl or especially preferably ethyl, as well as 2-hydroxy-ethyl.

Acyl $R_4$ or $R_5$ having 1–30 C atoms is derived from an unmodified or functionally modified carboxylic acid and is, in particular, one of the part formula Z—C(=W)—, in which W is oxygen, sulfur or imino and Z is hydrogen, hydrocarbyl $R^0$ having not more than 29 C atoms, hydrocarbyloxy $R^0$—O— or an amino group, in particular one of the formula $R_7(R_8)N$—.

Hydrocarbyl (a hydrocarbon radical) $R^0$ is an acyclic (aliphatic), carbocyclic or carbocyclic-acyclic hydrocarbon radical having not more than 29 C atoms, in particular not more than 18, and preferably not more than 12, carbon atoms, and is saturated or unsaturated and unsubstituted or substituted. Instead of one, two or more carbon atoms, it can also contain identical or different heteroatoms, such as, in particular, oxygen, sulfur and nitrogen, in the acyclic and/or cyclic moiety; in the latter case, it is called a heterocyclic radical (heterocyclyl radical) or a heterocyclic-acyclic radical.

Unsaturated radicals are those which contain one or more, in particular conjugated and/or isolated, multiple bonds (double bonds and/or triple bonds). The term cyclic radicals also encompasses aromatic radicals, for example those in which at least one 6-membered carbocyclic or one 5- to 8-membered heterocyclic ring contains the maximum number of non-cumulative double bonds. Carbocyclic radicals in which at least one ring is present as a 6-membered aromatic ring (i.e. benzene ring) are called aryl radicals.

An acyclic unsubstituted hydrocarbon radical is, in particular, a straight-chain or branched lower alkyl, lower alkenyl, lower alkadienyl or lower alkynyl radical. Lower alkyl is, for example, methyl, ethyl, n-propyl, isopropyl, n-butyl, isobutyl, sec-butyl or tert-butyl, and furthermore also n-pentyl, isopentyl, n-hexyl, isohexyl and n-heptyl. Lower alkenyl is, for example, allyl, propenyl, isopropenyl, 2- or 3-methallyl and 2- or 3-butenyl. Lower alkadienyl is, for example, 1-penta-2,4-dienyl; lower alkynyl is, for example, propargyl or butynyl. In corresponding unsaturated radicals, the double bond is located, in particular, in a position higher than the α position to the free valency.

A carbocyclic hydrocarbon radical is, in particular, a mono-, bi- or polycyclic cycloalkyl, cycloalkenyl or cycloalkadienyl radical, or a corresponding aryl radical. Preferred radicals are those having not more than 14, in particular 12, ring carbon atoms and 3- to 8-, preferably 5- to 7-, especially 6-membered rings, it also being possible for them to carry one or more, for example two, acyclic radicals, for example those mentioned above, and in particular the lower alkyl radicals, or further carbocyclic radicals. Carbocyclic-acyclic radicals are those in which an acyclic radical, in particular one having not more than 7, preferably not more than 4, carbon atoms, such as, in particular, methyl, ethyl and vinyl, carries one or more carbocyclic radicals, which may or may not be aromatic, as defined above. Cycloalkyl-lower alkyl and aryl-lower alkyl radicals, and their analogues unsaturated in the ring and/or chain, which carry the ring on the terminal C atom of the chain are mentioned in particular.

Cycloalkyl contains, in particular, 3 not more than and including 10 C atoms and is, for example, cyclopropyl, cyclobutyl, cyclopentyl, cyclohexyl, cycloheptyl and cyclooctyl, as well as bicyclo[2.2.2]octyl, 2-bicyclo[2.2.1] heptyl and adamantyl, which can also be substituted by 1, 2 or more, for example, lower alkyl radicals, in particular methyl radicals; cycloalkenyl is, for example, one of the monocyclic cycloalkyl radicals already mentioned which carries a double bond in the 1, 2 or 3 position. Cycloalkyl-lower alkyl or -lower alkenyl is, for example, a methyl, 1- or 2-ethyl, 1- or 2-vinyl, 1-, 2- or 3-propyl or allyl which is substituted by one of the abovementioned cycloalkyl radicals, those substituted at the end of the linear chain being preferred.

An aryl radical is, in particular, a phenyl, or furthermore a naphthyl, such as 1- or 2-naphthyl, a biphenylyl, such as, in particular, 4-biphenylyl, and moreover also an anthryl, fluorenyl and azulenyl, as well as their aromatic analogues having one or more saturated rings. Preferred aryl-lower alkyl and -lower alkenyl radicals are, for example, phenyl-lower alkyl or phenyl-lower alkenyl with a terminal phenyl radical, for example benzyl, phenethyl, 1-, 2- or 3-phenyl-propyl, diphenylmethyl (benzhydryl), trityl and cinnamyl, and furthermore also 1- or 2-naphthylmethyl. Aryl radicals which carry acyclic radicals, such as lower alkyl, are, in particular, o-, m- and p-tolyl und xylyl radicals with methyl radicals in various sites.

Heterocyclic radicals, including heterocyclic-acyclic radicals, are, in particular, monocyclic, but also bi- or polycyclic, aza-, thia-, oxa-, thiaza-, oxaza-, diaza-, triaza- or tetracyclic radicals of aromatic character, and corresponding partly or, in particular, completely saturated heterocyclic radicals of this type, it being possible for such radicals to carry, where appropriate, for example as the abovementioned carbocyclic or aryl radicals, further acyclic, carbocyclic or heterocyclic radicals and/or to be mono-, di- or polysubstituted by functional groups. The acyclic moiety in heterocyclic-acyclic radicals is as defined, for example, for the corresponding carbocyclic-acyclic radicals. These are, in particular, unsubstituted or substituted monocyclic radicals with one nitrogen, oxygen or sulfur atom, such as 2-aziridinyl, and in particular aromatic radicals of this type, such as pyrryl, for esterified carboxyl groups, carbamoyl, ureido or guanidino groups which may or may not carry one or two hydrocarbon radicals, and cyano groups.

An etherified hydroxyl group present as a substituent in hydrocarbyl is, for example, a lower alkoxy group, such as the methoxy, ethoxy, propoxy, isopropoxy, butoxy and tert-butoxy group, which can also be substituted. Thus, such a lower alkoxy group can be substituted by halogen atoms, for example once, twice or several times, in particular in the 2 position, as in the 2,2,2-trichloroethoxy, 2-chloroethoxy or 2-iodoethoxy radical, or by hydroxyl or lower alkoxy radicals, in each case preferably once, in particular in the 2-position, as in the 2-methoxyethoxy radical. A particularly preferred embodiment of the etherified hydroxyl groups exists in oxaalkyl radicals in which one or more C atoms in an alkyl, preferably a linear alkyl, are replaced by oxygen atoms, which are preferably separated from one another by more than one (in particular 2) C atoms, so that they form a group (—O—CH$_2$—CH$_2$)$_n$—, which may or may not recur more than one, in which n is 1 to 14. Such etherified hydroxyl groups are furthermore also substituted or unsubstituted phenoxy radicals and phenyl-lower alkoxy radicals, such as, in particular, benzyloxy, benzhydryloxy and triphenylmethoxy (trityloxy), as well as heterocyclyloxy radicals, such as, in particular, 2-tetrahydropyranyloxy. A particular etherified hydroxyl group is the grouping methylenedioxy or ethylenedioxy, the former as a rule bridging 2 adjacent C atoms, in particular in aryl radicals, and the latter being bonded to one and the same C atom and being regarded as a protective group for oxo.

Etherified hydroxyl groups in this connection are also to be understood as meaning silylated hydroxyl groups, such as are present, for example, in tri-lower alkylsilyloxy, such as trimethylsilyloxy and dimethyl-tert-butylsilyloxy, or phenyl di-lower alkylsilyloxy or lower alkyl-diphenylsilyloxy.

An esterified hydroxyl group present as a substituent in hydrocarbyl is, for example, lower alkanoyloxy.

An esterified carboxyl group present as a substituent in hydrocarbyl is one in which the hydrogen atom is replaced by one of the hydrocarbon radicals characterized above, preferably a lower alkyl or phenyl-lower alkyl radical; an example of an esterified carboxyl group is, for example, lower alkoxycarbonyl or phenyl-lower alkoxycarbonyl which is unsubstituted or substituted in the phenyl moiety, in particular the methoxy-, ethoxy-, tert-butoxy- and benzyloxycarbonyl group, and also a lactonized carboxyl group.

A primary amino group —NH$_2$ as a substituent of hydrocarbyl can also be present in protected form. A secondary amino group carries, instead of one of the two hydrogen atoms, a hydrocarbyl radical, preferably an unsubstituted one, such as one of those mentioned above, in particular lower alkyl, and can also be present in a protected form.

A tertiary amino group occurring as a substituent in hydrocarbyl carries 2 different or, preferably, identical hydrocarbyl radicals (including the heterocyclic radicals) such as the unsubstituted hydrocarbyl radicals characterized above, in particular lower alkyl.

In a group of the formula $R_7(R_8)N-$, $R_7$ and $R_8$ independently of one another are each hydrogen, lower alkylsulfonyl, acyclic $C_1-C_7$hydrocarbyl (such as, in particular, $C_1-C_4$alkyl or $C_2-C_4$alkenyl) which is unsubstituted or substituted, for example by amino, guanidino, phenyl, hydroxyphenyl, carboxyl, carbamoyl, imidazolyl, mercapto or methylthio, or monocyclic aryl, aralkyl or aralkenyl which has not more than 10 C atoms and is unsubstituted or substituted by $C_1-C_4$alkyl, $C_1-C_4$alkoxy, halogen and/or nitro, it being possible for the carbon-containing radicals $R_7$ and $R_8$ to be bonded to one another by a carbon—carbon bond or an oxygen atom, a sulfur atom or a nitrogen atom which is unsubstituted or substituted by hydrocarbyl. In such a case, together with the nitrogen atom of the amino group, they form a nitrogen-containing heterocyclic ring. Examples of particularly preferred groups of the formula $R_7(R_8)N-$ are the following: amino, lower alkylamino, such as methylamino, or ω-amino-lower alkylamino, such as 2-aminoethylamino or 3-amino-propylamino; di-lower alkylamino, such as dimethylamino or diethylamino; pyrrolidino, 2-hydroxymethyl-pyrrolidino, piperidino, 4-(2-amino-ethyl)-piperidino, morpholino or thiomorpholino; piperazino, 4-methyl-piperazino, 4-(2-amino-ethyl)-piperazino, or phenylamino, diphenylamino or dibenzylamino which are unsubstituted or, in particular, substituted in the phenyl moiety, for example by lower alkyl, lower alkoxy, halogen and/or nitro, and among the protected groups, in particular lower alkoxycarbonylamino, such as tert-butoxycarbonylamino, phenyl-lower alkoxycarbonylamino, such as 4-methoxybenzyloxycarbonylamino, and 9-fluorenyl-methoxycarbonylamino. Preferred groups of the formula Z—C (=W)— in which Z is a group of the formula $R_7(R_8)N-$ are carbamoyl, N-methyl-carbamoyl, N-(ω-amino-lower alkyl)-carbamoyl, N-(α-amino-acyl)-carbamoyl, N-phenyl-carbamoyl, N-methylsulfonyl-carbamoyl and corresponding radicals in which W is not oxygen but sulfur or imino, such as amidino, N-methyl-amidino $[CH_3-NH-C(=NH)-]$, N-methyl-thiocarbamoyl $[CH_3-NH-C(=S)-]$ or N-(ω-amino-lower alkyl)-thiocarbamoyl. For example, a radical of the formula $-N(R_4)-R_5$ in which $R_4$ is hydrogen and $R_5$ is amidino is guanidino $[H_2N-C(=NH)-NH-]$.

Unless stated otherwise, aromatic carbocyclic and heterocyclic hydrocarbyl radicals above and below can be substituted once or more than once, for example twice or three times, in particular by $C_1-C_4$alkyl, $C_1-C_4$alkoxy, halogen, nitro, trifluoromethyl and furthermore carboxyl, $C_1-C_4$alkoxycarbonyl, methylenedioxy, and/or cyano. Reduced descriptions of substituents given above and below are to be regarded as preferences.

Preferred compounds of the formula I according to the invention are, for example, those in which hydrocarbyl $R^0$ has the following preferred meanings of an acyclic hydrocarbyl: a $C_1-C_{20}$alkyl, a $C_2-C_{20}$hydroxyalkyl, the hydroxyl group of which is in any position other than the 1 position, preferably in the 2 position, a cyano-$[C_1-C_{20}]$-alkyl, the cyano group in which is preferably in the 1 or ω position, or a carboxy-$[C_1-C_{20}]$-alkyl, the carboxyl group of which is preferably in the 1 or ω position and can be present in the free form or also in salt form, or as a $C_1-C_4$alkylester ($C_1-C_4$alkoxycarbonyl) or benzylester (benzyloxycarbonyl), and a $C_3-C_{20}$alkenyl, the free valency of which is not on the same C atom as the double bond, all the radicals mentioned, excluding those having the $C_3-C_5$alkyl base structure, containing a linear (unbranched) alkyl chain; and furthermore also a linear (mono-, di- to hexa)-oxoalkyl having 4–20 chain members, in which one or more of the C atoms, from C-3 on, of a linear $C_4-C_{20}$alkyl is replaced by oxygen atoms, which are separated from one another by at least 2 C atoms and are preferably in positions 3, 6, 9, 12, 15 and 18.

Preferred compounds of the formula I according to the invention are also those in which hydrocarbyl $R^0$ has the following preferred meanings of a carbocyclic or heterocyclic and also carbocyclic-acyclic or heterocyclic-acyclic hydrocarbyl: a bicyclic or preferably monocyclic aryl, in particular phenyl, and furthermore naphthyl, which can carry one or more of the following substituents: halogen atoms, in particular fluorine, chlorine and bromine, $C_1-C_4$alkyl radicals, in particular methyl, $C_1-C_4$alkoxy groups, in particular methoxy, methylenedioxy, nitro groups and/or carboxyl groups, which can be free or present in a salt form or as $C_1-C_4$alkyl esters, in particular methoxycarbonyl or ethoxycarbonyl. Preferably, the aryl radicals carry not more than 2 substituents, in particular those of the same type, or only a single substituent; in particular, they are unsubstituted. Preferred heterocyclic hydrocarbyl (heterocyclyl) is, for example, that which is analogous to the aryl radicals preferred above and, instead of one or 2 C atoms, contains in each case a heteroatom, in particular nitrogen, such as a pyridyl or quinolyl or quinazolyl, where the free valency is located on a C atom, and can also be substituted accordingly. Preferred carbocyclic-acyclic and heterocyclic-acyclic hydrocarbyl radicals are those in which two or three, but preferably only one, of the cyclic radicals defined above, preferably the unsubstituted radical, is carried by a $C_1-C_3$alkyl, all preferably being located on one C atom, preferably the terminal C atom; unsubstituted benzyl is most preferred.

Particularly preferred compounds of the formula I are those in which $R^0$ is $C_1-C_7$alkyl, in particular $C_1-C_4$alkyl, hydroxy-$C_2-C_{18}$alkyl, in particular hydroxy-$C_2-C_{14}$alkyl, cyano-$C_1-C_7$alkyl, in particular cyano-$C_1-C_4$alkyl, carboxy-$C_1-C_7$alkyl, in particular carboxy-$C_1-C_4$alkyl, $C_1-C_7$alkoxy-carbonyl-$C_1-C_7$alkyl, in particular $C_1-C_4$alkoxy-carbonyl-$C_1-C_4$alkyl, benzyloxycarbonyl-$C_1-C_7$alkyl, in particular benzyloxycarbonyl-$C_1-C_4$alkyl, $C_3-C_7$alkenyl, phenyl, naphthyl, pyridyl, quinolyl, or quinazolyl, or phenyl-$C_1-C_7$alkyl, in particular phenyl-$C_1-C_3$alkyl, it also being possible for the particular aromatic radicals furthermore to be substituted by $C_1-C_7$alkyl, in particular $C_1-C_4$alkyl, $C_1-C_7$alkoxy, in particular $C_1-C_4$alkoxy, halogen, nitro, trifluoromethyl or furthermore carboxyl, $C_1-C_4$alkoxy-carbonyl, methylenedioxy and/or cyano, the hydroxyl group in the correspondingly substituted alkyl radical being located, in particular, in the 2 position and the cyano, carboxyl, alkoxycarbonyl, benzyloxy-carbonyl or phenyl group in the correspondingly substituted alkyl radical being located, in particular, in the 1 or ω position.

Particularly preferred compounds of the formula I are those in which $R^0$ is $C_1-C_4$alkyl, such as methyl or ethyl, hydroxy-$C_2-C_{14}$alkyl, such as 2-hydroxy-propyl, -hexyl, -decyl or -tetradecyl, cyano-$C_1-C_4$alkyl, such as 2-cyanoethyl, carboxy-$C_1$–$C_4$alkyl, such as carboxymethyl, $C_1$–$C_4$alkoxycarbonyl-$C_1$–$C_4$alkyl, such as methoxycarbonyl-methyl or -ethyl, $C_3$–$C_7$alkenyl, such as allyl, or phenyl, the hydroxyl group in the correspondingly substituted alkyl preferably being located in the 2 position and the cyano, carboxyl or alkoxycarbonyl group being located, in particular, in the 1 or ω position.

A substituted aliphatic hydrocarbon radical $R_4$ or $R_5$ having not more than 29 C atoms is a substituted alkyl or in each case mono- or polyunsaturated alkenyl or alkynyl radical having in each case not more than 29 C atoms, i.e. a substituted $C_1$–$C_{29}$alkyl, $C_2$–$C_{29}$alkenyl or $C_2$–$C_{29}$alkynyl radical. As a rule, these radicals, including their substituents, have not more than 19, in particular not more than 12, and especially not more than 10, C atoms. Suitable substituents are also cyclic radicals, so that $R_4$ and $R_5$ in each case can also be carbocyclic-aliphatic radicals or heterocyclic-aliphatic radicals having in each case not more than 29 C atoms. The substituted aliphatic hydrocarbon radical, such as, preferably, ethyl or n-propyl radical, can carry one or more identical or different radicals. Depending on the nature of the substituents, these can be attached via a single or multiple bond or linked in spiro form. Preferred substituents are halogen, such as chlorine, fluorine, bromine or iodine, amino, lower alkylamino, ω-amino-lower alkylamino, lower alkanoylamino, aroylamino, such as, in particular, benzoylamino, hydroxylamino, hydroxylimino, lower alkoxyamino, aryloxyamino, such as, in particular, phenyloxyamino, amino-cyclohexyl-amino-, amino-phenyl-amino-, carbamoyl-amino (ureido, —NH—C(=O)—$NH_2$), (N-lower alkyl-carbamoyl)-amino (—NH—C(=O)—NH-lower alkyl), (N-[ω-amino-lower alkyl]-carbamoyl)-amino (—NH—C(=O)—NH-lower alkyl-$NH_2$), (N-phenyl-carbamoyl)-amino (—NH—C(=O)—NH-phenyl), thio, lower alkylthio, such as methylthio, thiocarbamoyl (—C(=S)—$NH_2$), thioureido (—NH—C(=S)—$NH_2$), N-lower alkyl-thioureido (—NH—C(=S)—NH-lower alkyl), N-phenyl-thioureido (—NH—C(=S)—NH-phenyl), guanidino, N-lower alkyl-guanidino, carboxyl, lower alkoxycarbonyl, aryloxycarbonyl, such as, in particular, phenyloxycarbonyl, benzyloxycarbonyl, hydroxylaminocarbonyl, aminoacylamino, carbamoyl, amidino (—C[=NH]—$NH_2$), cyano, hydroxyl, lower alkoxy, aryloxy, such as, in particular, phenyloxy, aminocarbonyl-oxy (—O—C[=O]—$NH_2$), oxo, aminosulfonyl and lower alkylsulfonyl-amino.

Aminoacyl as part of the above mentioned aminoacyl-amino substituent of an aliphatic hydrocarbon radical $R_4$ or $R_5$ is, in particular, the C-terminal radical of an amino acid, such as an α-amino acid, for example one of the naturally occurring α-amino acids, in particular one of the 20 essential α-amino acids which regularly occur in proteins, i.e. glycine, alanine, phenylalanine, proline, valine, leucine, isoleucine, serine, threonine, cysteine, methionine, tyrosine, tryptophan, arginine, histidine, lysine, glutamic acid, glutamine, aspartic acid and asparagine, and in addition phenylglycine. Aminoacyl is preferably amino-lower alkanoyl, which is unsubstituted or substituted by amino, phenyl, hydroxyphenyl, hydroxyl, mercapto, methylthio, indol-3-yl, carbamoyl, carboxyl, guanidino or imidazolyl.

Preferred substituted aliphatic hydrocarbon radicals $R_4$ or $R_5$ without cyclic substituents are, for example, 2-carbamoyl-1-carboxy-eth-1-yl, 3-amino-2-hydroxy-prop-1-yl, 3-amino-prop-1-yl, 3-amino-2,2-dimethyl-prop-1-yl, 3-amino-2-oxo-prop-1-yl, 3-amino-1-carboxy-prop-1-yl, 3-amino-3-carboxy-prop-1-yl, 1,1-dicarbamoyl-methyl, 2-carbamoyl-eth-1-yl, 3-amino-1,3-di-hydroxylimino-prop-1-yl, 2-carbamoyl-1-hydroxylimino-eth-1-yl, 1-hydroxylimino-2-thiocarbamoyl-eth-1-yl, 3-amino-3-hydroxylimino-1-thio-prop-1-yl, 3-amino-pent-1-yl, 1-amino-pent-3-yl, 1-amidino-1-carbamoyl-methyl, 4-amino-1,1,1,3,5,5,5-heptafluoro-pent-2-yl, 3-amino-1,3-dicarboxy-prop-1-yl, 2-carbamoyl-1-ethoxycarbonyl-eth-1-yl, 2-amino-1,2-dithio-eth-1-yl, 2-amino-1,2-dioxo-eth-1-yl, 2-amino-2-methyl-prop-1-yl, 1-amino-2-methyl-prop-2-yl, 2-amino-prop-1-yl, 1-amino-prop-2-yl, 2-amino-eth-1-yl, 2-amino-2-carboxy-eth-1-yl, 2-amino-1-carboxy-eth-1-yl, carbamoyl-methyl, 1-carbamoyl-3-methyl-but-1-yl, 2-amino-1,2-dicarboxy-eth-1-yl, 1-carbamoyl-3-methylthio-prop-1-yl, 1-carbamoyl-2-methyl-prop-1-yl, 1-carbamoyl-eth-1-yl, 1-carbamoyl-1-cyano-methyl, 1-carbamoyl-3-carboxy-3-fluoro-prop-1-yl, 1-carbamoyl-2-carboxy-eth-1-yl, 2-amino-4-carboxy-but-1-yl, 1-amino-4-carboxy-but-2-yl, 1-carbamoyl-4-guanidino-but-1-yl, 1-carbamoyl-5-amino-pent-1-yl, 1-carbamoyl-2-hydroxy-prop-1-yl, 1-carbamoyl-2-methyl-but-1-yl, 1-carbamoyl-2-hydroxy-eth-1-yl, 1,3-dicarbamoyl-prop-1-yl, 2-amino-but-1-yl, 1-amino-but-2-yl, 1-carbamoyl-pent-1-yl, 1-carbamoyl-but-1-yl, 2-hydroxy-ethyl, 3-hydroxy-prop-1-yl, 2-hydroxy-prop-1-yl, 2-hydroxymethyl-prop-2-yl, 1-hydroxy-but-2-yl, 1,3-dihydroxy-prop-2-yl, 2-cyano-ethyl, 2-mercapto-ethyl, 3-amino-2-hydroxy-prop-1-yl, 2-(N-methyl-amino)-ethyl, 2-(2-amino-ethyl-amino)-ethyl, 2-guanidino-ethyl and 2-acetylamino-ethyl.

A carbocyclic-aliphatic radical $R_4$ or $R_5$ can be substituted both in the carbocyclic and in the aliphatic moiety and is, for example, a cycloaliphatic-aliphatic radical, for example cycloalkyl-lower alkyl or -lower alkenyl, for example a methyl, 1- or 2-ethyl, 1- or 2-vinyl, 1-, 2- or 3-propyl or allyl substituted by one of the cycloalkyl radicals mentioned above or below, those substituted at the end of the linear chain being preferred, or an aromatic-aliphatic radical. Preferred carbocyclic-aliphatic radicals $R_4$ or $R_5$ are, for example, benzyl, 2-phenyl-ethyl, 2-amino-benzyl, 3-aminomethyl-benzyl, (1-hydroxy-cyclohex-1-yl)-methyl, (2-amino-3,5,5-trimethyl-cyclopentyl)-methyl, 1-[N-(1-carboxy-2-phenyl-ethyl)-carbamoyl]-2-carbamoyl-eth-1-yl, 1-carbamoyl-1-phenyl-methyl, 1-carbamoyl-2-(4-hydroxyphenyl)-eth-1-yl, 1-carbamoyl-2-phenyl-eth-1-yl, 2-amino-1,2-diphenyl-eth-1-yl, 2-benzyloxycarbonyl-1-carbamoyl-eth-1-yl, 3-benzyloxycarbonyl-1-carbamoyl-prop-1-yl, 1-adamantyl-2-amino-prop-1-yl and 1-adamantyl-1-amino-prop-2-yl.

A heterocyclic-aliphatic radical $R_4$ or $R_5$ can be substituted both in the heterocyclic and in the aliphatic moiety. Preferred heterocyclic aliphatic radicals $R_4$ or $R_5$ are, for example, (2-furyl)-methyl, (2-tetrahydrofuryl)-methyl, 2-pyrid-2-yl-ethyl, 2-piperidino-ethyl, 2-(morpholin-4-yl)-ethyl, 2-(3-indolyl)-ethyl, 2-(4-imidazolyl)-ethyl, 1-carbamoyl-2-(β-indolyl)-eth-1-yl, 1-carbamoyl-2-imidazol-4-yl-eth-1-yl, 1-carbamoyl-2-indol-3-yl-eth-1-yl, 3-aminomethyl-oxetan-3-yl-methyl and 1-(acetoxy-imino)-1-(4-amino-2-oxa-1,3-diazol-5-yl)-methyl.

A carbocylic radical $R_4$ or $R_5$ having not more than 29 C atoms is such an unsubstituted or substituted hydrocarbon radical, i.e. such a cycloaliphatic or aromatic radical. A carbocyclic hydrocarbon radical is, in particular, a mono-, bi- or polycyclic cycloalkyl, cycloalkenyl or cycloalkadienyl radical, or a corresponding aryl radical. Radicals having not more than 14, in particular 12, ring carbon atoms and 3- to 8-, preferably 5- to 7-, in particular 6-membered rings are preferred, it also being possible for them to carry one or more, for example two, acyclic radicals, for example those mentioned above, and in particular the lower alkyl radicals, or further carbocyclic radicals.

Cycloalkyl represented by the radicals $R_4$ or $R_5$ contains, in particular, 3 not more than and including 10 C atoms and is, for example, cyclopropyl, cyclobutyl, cyclopentyl, cyclohexyl, cycloheptyl and cyclooctyl, as well as bicyclo[2.2.2] octyl, 2-bicyclo[2.2.1]heptyl and adamantyl, which can also be substituted by 1, 2 or more, for example lower, alkyl radicals, in particular methyl radicals; cycloalkenyl is, for example, one of the monocyclic cycloalkyl radicals already mentioned which carries a double bond in the 1, 2 or 3 position.

An aryl radical represented by the radicals $R_4$ or $R_5$ is, in particular, a phenyl, furthermore a naphthyl, such as 1- or 2-naphthyl, a biphenylyl, such as, in particular, 4-biphenylyl, and moreover also an anthryl, fluorenyl or azulenyl radical, and their aromatic analogues with one or more saturated rings. Preferred aryl-lower alkyl and -lower alkenyl radicals are, for example, phenyl-lower alkyl or phenyl-lower alkenyl with a terminal phenyl radical, such as, for example, benzyl, phenethyl, 1-, 2- or 3-phenyl-propyl, diphenylmethyl (benzhydryl), trityl and cinnamyl, and furthermore also 1- or 2-naphthylmethyl. Aryl radicals which carry acyclic radicals, such as lower alkyl, are, in particular, o-, m- and p-tolyl and xylyl radicals with methyl radicals in various sites.

Preferred carbocyclic radicals $R_4$ or $R_5$ are, for example, amino-phenyl, such as 2-amino-phenyl, 3-amino-phenyl and 4-amino-phenyl, cyclohexyl, 4-methyl-cyclohexyl, amino-cyclohexyl, such as 2-amino-cyclohex-1-yl, 3-amino-cyclohex-1-yl and 4-amino-cyclohex-1-yl, hydroxy-cyclohexyl, for example 2-hydroxy-cyclohexyl and 4-hydroxy-cyclohexyl, 1-(hydroxymethyl)-cyclopent-1-yl, 2-aminomethyl-3,3,5-trimethyl-cyclopent-1-yl, adamant-1-yl, 3-amino-adamantan-1-yl, 2-carbamoyl-bicyclo[2.2.1]hept-5-en-3-yl, 2-carbamoyl-cyclohex-1-yl and 9-amino-spiro[4,4]non-1-yl.

Heterocyclic radicals $R_4$ or $R_5$ having not more than 20 C atoms and not more than 9 heteroatoms are preferably bonded via one of their ring carbon atoms and are, in particular, monocyclic, but also bi- or polycyclic, aza-, thia-, oxa-, thiaza-, oxaza-, diaza-, triaza- or tetrazacyclic radicals of aromatic character, and corresponding partly or, in particular, completely saturated heterocyclic radicals of this type, it being possible for such radicals, where appropriate, for example like the abovementioned carbocyclic or aryl radicals, to carry further acyclic, carbocyclic or heterocyclic radicals and/or to be mono-, di- or polysubstituted by functional groups. In particular, they are unsubstituted or substituted monocyclic radicals with one nitrogen, oxygen or sulfur atom, such as 2-aziridinyl, and in particular aromatic radicals of this type, such as pyrryl, for example 2-pyrryl or 3-pyrryl, pyridyl, for example 2-, 3- or 4-pyridyl, and furthermore thienyl, for example 2- or 3-thienyl, or furyl, for example 2-furyl; analogous bicyclic radicals with one nitrogen, oxygen or sulfur atom are, for example, indolyl, such as 2- or 3-indolyl, quinolyl, such as 2- or 4-quinolyl, isoquinolyl, such as 3- or 5-isoquinolyl, benzofuranyl, such as 2-benzofuranyl, chromenyl, such as 3-chromenyl, or benzothienyl, such as 2- or 3-benzothienyl; preferred monocyclic and bicyclic radicals with more than one heteroatom are, for example, imidazolyl, such as 2-imidazolyl, pyrimidinyl, such as 2- or 4-pyrimidinyl, oxazolyl, such as 2-oxazolyl, isoxazolyl, such as 3-isoxazolyl, or thiazolyl, such as 2-thiazolyl, or benzimidazolyl, such as 2-benzimidazolyl, benzoxazolyl, such as 2-benzoxazolyl, or quinazolyl, such as 2-quinazolinyl. Also suitable are corresponding partly or, in particular, completely saturated analogous radicals, such as 2-tetrahydrofuryl, 4-tetrahydrofuryl, 2- or 3-pyrrolidyl, 2-, 3-, or 4-piperidyl, and also 2- or 3-morpholinyl, 2- or 3-thiomorpholinyl, 2-piperazinyl and N,N'-bis-lower alkyl-2-piperazinyl radicals. These radicals can also carry one or more acyclic, carbocyclic or heterocyclic radicals, in particular those mentioned above.

A heterocyclic radical $R_4$ or $R_5$ can be substituted by one, two or more identical or different substituents (functional groups); the following substituents are particularly suitable: free, etherified and esterified hydroxyl groups; mercapto and lower alkylthio and substituted and unsubstituted phenylthio groups; halogen atoms, such as chlorine and fluorine, but also bromine and iodine; oxo groups, which are in the form of formyl (i.e. aldehydo) and keto groups, and also corresponding acetals or ketals; azido and nitro groups; primary, secondary and, preferably, tertiary amino groups, primary or secondary amino groups, acylamino groups and diacylamino groups protected by conventional protective groups, and unmodified or functionally modified sulfo groups, such as sulfamoyl groups or sulfo groups present in salt form. All these functional groups should not be on the C atom from which the free valency comes, and they are preferably separated from it by 2 or even more C atoms. The heterocyclic radical can also carry free and functionally modified carboxyl groups, such as carboxyl groups present in salt form or esterified carboxyl groups, carbamoyl, ureido or guanidino groups, which may or may not carry one or two hydrocarbon radicals, and cyano groups.

Preferred heterocyclic radicals $R_4$ or $R_5$ are, for example, 5-amino-2-oxa-1,3-diazol-4-yl, 4-amino-thien-3-yl, 3-carbamoyl-5-(3-[2,4-dichloro-phenyl]-1-oxo-prop-2-en-1-yl)-1,2-thiazol-4-yl, 3-carbamoyl-5-(3-[4-trifluoro-phenyl]-1-oxo-prop-2-en-1-yl)-1,2-thiazol-4-yl, 4-amino-2-(4-carboxy-butyl)-tetrahydrothiophen-3-yl, 3-amino-2-(4-carboxy-butyl)-tetrahydrothiophen-4-yl, [1,2,5]oxadiazolo[3,4-b](6-amino-pyrazin-5-yl), 2,5'-diacetyl-3-amino-thieno[2,3-b]thiophen-4'-yl and 3-amino-2,5'-dipivaloyl-thieno[2,3-b]thiophen-4'-yl.

A substituted or unsubstituted alkylene or alkenylene radical having in each case not more than 15 C atoms, in which 1–3 C atoms can be replaced by oxygen, sulfur or nitrogen, which is represented by $R_4$ and $R_5$ together, is branched or unbranched and preferably has not more than 10 C atoms, not including the C atoms present in any substituents. Substituents are, for example, those mentioned above for substituted aliphatic hydrocarbon radicals $R_5$. The substituents can be either on a C atom or on oxygen, sulfur or, in particular, nitrogen.

Preferred radicals are, for example, 1,2-ethylene, propane-1,3-diyl, butane-1,4-diyl, pentane-1,5-diyl, 3-(3-amino-propionyl)-3-aza-pentane-1,5-diyl, 2-amino-butane-1,4-diyl, 1-aminomethyl-butane-1,4-diyl, 1-hydroxymethyl-butane-1,4-diyl, 3-hydroxy-pentane-1,5-diyl, 1-hydroxy-hexane-1,5-diyl, 3-(2-amino-ethyl)-pentane-1,5-diyl, 3-aza-pentane-1,5-diyl(—CH$_2$—CH$_2$—NH—CH$_2$—CH$_2$—), 3-aza-2,4-dimethyl-pentane-1,5-diyl (—CH$_2$—CH[CH$_3$]—NH—CH[CH$_3$]—CH$_2$—), 3-amino-3-aza-pentane-1,5-diyl(—CH$_2$—CH$_2$—N[NH$_2$]—CH$_2$—CH$_2$—), 1-aza-pentane-1,5-diyl, 1-aza-1-toluylaminocarbonyl-pentane-1,5-diyl, 1-aza-1-(methylamino-thiocarbonyl)-pentane-carbonyl)-pentane-1,5-diyl, 1-aza-1-(tert-butylaminocarbonyl)-pentane-1,5-diyl, 1-aza-1-(cyclohexylaminocarbonyl)-pentane-1,5-diyl, 3-aza-1-hydroxy-heptane-3,7-diyl, 3-aza-1-cyano-heptane-3,7-diyl, 1-amino-3-aza-heptane-3,7-diyl, 3-(2-amino-ethyl)-3-aza-pentane-1,5-diyl (—CH$_2$—CH$_2$—N[—CH$_2$—CH$_2$—NH$_2$]—CH$_2$—CH$_2$—), 1-carbamoyl-butane-1,4-diyl, 2-formylamino-pentane-1,4-diyl, 2-aza-butadiene-1,4-diyl (—CH=CH—N=CH—), 2-aza-3-hydroxymethyl-butadiene-1,4-diyl (—C H=C [CH₂OH]—N=CH—), 2-Aza-1-hydroxy-1-(4-methoxy-phenyl-amino)-heptane-2,7-diyl {—(CH₂)₄—N[—CH (OH)—NH—C₆H₄—OCH₃]—} or a radical of the formula

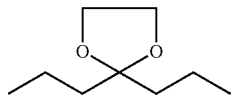

in which the two terminal bonds of the alkylene chain are free valencies.

Salts of compounds of formula I are, in particular, acid addition salts with organic or inorganic acids, in particular the pharmaceutically acceptable, non-toxic salts. Suitable inorganic acids are, for example, carbonic acid (preferably in the form of carbonates or bicarbonates); hydrohalic acids, such as hydrochloric acid; sulfuric acid; or phosphoric acid. Suitable organic acids are, for example, carboxylic, phosphonic, sulfonic or sulfonamic acids, for example acetic acid, propionic acid, octanoic acid, decanoic acid, dodecanoic acid, glycolic acid, lactic acid, 2-hydroxybutyric acid, gluconic acid, glucose monocarboxylic acid, fumaric acid, succinic acid, adipic acid, pimelic acid, suberic acid, azelaic acid, malic acid, tartaric acid, citric acid, glucaric acid, galactaric acid; amino acids, such as glutamic acid, aspartic acid, N-methylglycine, acetylaminoacetic acid, N-acetylasparagine or N-acetyl-cysteine, pyruvic acid, acetoacetic acid, phosphoserine, 2- or 3-glycerophosphoric acid, glucose-6-phosphoric acid, glucose-1-phosphoric acid, fructose-1,6-bisphosphoric acid, maleic acid, hydroxymaleic acid, methylmaleic acid, cyclohexanecarboxylic acid, adamantanecarboxylic acid, benzoic acid, salicylic acid, 1- or 3-hydroxynaphthyl-2-carboxylic acid, 3,4,5-trimethoxybenzoic acid, 2-phenoxybenzoic acid, 2-acetoxybenzoic acid, 4-aminosalicylic acid, phthalic acid, phenylacetic acid, mandelic acid, cinnamic acid, nicotinic acid, isonicotinic acid, glucuronic acid, galacturonic acid, methane- or ethanesulfonic acid, 2-hydroxyethanesulfonic acid, ethane-1,2-disulfonic acid, benzenesulfonic acid, 2-naphthalenesulfonic acid, 1,5-naphthalenedisulfonic acid, 2-, 3- or 4-methylbenzene-sulfonic acid, methylsulfuric acid, ethylsulfuric acid, dodecylsulfuric acid, N-cyclohexyl-sulfamic acid, N-methyl-, N-ethyl- or N-propylsulfamic acid, or other organic protonic acids, such as ascorbic acid.

Compounds of the formula I which carry at least one free carboxyl group can form inner salts or metal or ammonium salts, such as alkali metal or alkaline earth metal salts, for example sodium, potassium, magnesium or calcium salts or ammonium salts with ammonia or suitable organic amines, such as tertiary monoamines, for example triethylamine or tri(2-hydroxy-ethyl)-amine, or heterocyclic bases, for example N-ethyl-piperidine or N,N'-dimethyl-piperazine.

Pharmaceutically unsuitable salts, for example picrates or perchlorates, can also be used for isolation or purification. Only the non-toxic salts which are pharmaceutically acceptable (at the appropriate doses) are used therapeutically, and are therefore preferred.

As a result of the close relationship between the novel compounds in free form and in the form of their salts, including also those salts which can be used as intermediates, for example during purification of the novel compounds or for their identification, where appropriate the free compounds above and below are to be understood appropriately and expediently as also meaning the corresponding salts.

The compounds of the formula I have valuable pharmacologically useful properties. In particular, they display specific inhibiting actions which are of pharmacological interest.

The compounds of the formula I and their pharmaceutically acceptable salts inhibit the enzyme p34$^{cdc2}$/cyclin B$^{cdc13}$ kinase. In addition to other cdc2-related kinases, this kinase controls certain phases during cell division, in particular the transition from the G$_1$ phase into the S phase, and in particular the transition from the G$_2$ phase into the M phase.

The cycle of a eukaryotic cell comprises, in chronological sequence, the interphase and the M phase. The interphase is accompanied by an enlargement of the cell. It in turn comprises, in chronological sequence, the G$_1$ phase, the S phase and the G$_2$ phase. In the G$_1$ phase (G="gap", i.e. interspace), biosynthetic processes proceed in the cell. In the S phase (synthesis phase), the DNA replicates. The cell then enters the G$_2$ phase, which ends with the start of mitosis.

The M phase in turn comprises, in chronological sequence, division of the cell nucleus (mitosis) and division of the cytoplasm (cytokinesis).

The abovementioned inhibition of the enzyme p34$^{cdc2}$/cyclin B$^{cdc13}$ kinase can be demonstrated by the following experiment:

Starfish oocytes are induced into the M phase with 10 μM 1-methyl-adenine, frozen in liquid nitrogen and stored at −80° C. The ooctyes are homogenized and centrifuged, as described in D. Arion et al., Cell 55, 371–378 (1988) and V. Rialet und L. Meijer, Anticancer Res. 11, 1581–1590 (1991), as required. For purification of the p34$^{cdc2}$/cyclin B$^{cdc13}$ kinase, the supernatant of the oocytes is introduced onto p9$^{CKShs}$ Sepharose grains produced from recombinant human protein p9$^{CKShs}$, as described in L. Azzi et al., Eur. J. Biochem. 203, 353–360 (1992). After 30 minutes at 4° C. under constant rotation, the grains are washed thoroughly and the active p34$^{cdc2}$/cyclin B$^{cdc13}$ kinase is eluted with free protein p9$^{CKShs}$ (3 mg/ml). The kinase eluted is tested as described in L. Meijer et al., EMBO J. 8, 2275–2282 (1989) and EMBO J. 10, 1545–1554 (1991), using histone H1 as the substrate. In this test, the compounds of the formula I and their pharmaceutically acceptable salts have an inhibiting concentration IC$_{50}$[μmol/litre] of 0.0005 to 4, usually of 0.001 to 3.

On the basis of this finding, it can be expected that the compounds of the formula I and their pharmaceutically acceptable salts can be used for treatment of hyperproliferative diseases, such as tumours and psoriasis.

As can already be expected on the basis of the inhibiting action on the enzyme p34$^{cdc2}$/cyclin B$^{cdc13}$ kinase described above, the compounds of the formula I and their pharmaceutically acceptable salts have antiproliferative properties which can be demonstrated directly in another test as follows: here, the inhibiting action of the compounds of the formula I on the growth of human T24 bladder carcinoma cells is determined. These cells are incubated in "Eagle's minimal essential medium", to which 5% (v/v) of foetal calf serum is added, in a humidified incubator at 37° C. and 5 percent by volume CO$_2$ in air. The carcinoma cells (1000–1500) are seeded into 96-well microtitre plates and incubated overnight under the abovementioned conditions. The test substance is added in serial dilutions on day 1. The plates are incubated under the abovementioned conditions for 5 days. During this period of time, the control cultures pass through at least 4 cell divisions. After the incubation, the cells are fixed with 3.3% (W/V) aqueous glutaraldehyde solution, washed with water and stained with 0.05% (weight/volume) aqueous methylene blue solution. After washing, the dye is eluted with 3% (W/V) aqueous hydrochloric acid. Thereafter, the optical density (OD) per well, which is directly proportional to the cell count, is measured with a photometer (Titertek multiskan) at 665 nm. The $IC_{50}$ values are calculated with a computer system using the formula $$\frac{OD_{665}(\text{Test}) \text{ minus } OD_{665}(\text{Initial})}{OD_{665}(\text{Control}) \text{ minus } OD_{665}(\text{Initial})} \times 100.$$

The $IC_{50}$ values are defined as that concentration of active compound at which the number of cells per well at the end of the incubation period is only 50% of the cell count in the control cultures. The $IC_{50}$ values determined in this way are about 0.1 to 30 µmol/litre for the compounds of the formula I and their pharmaceutically acceptable salts.

The antitumoural action of the compounds of the formula I can also be demonstrated in vivo:

to determine the antitumoural action, female Balb/c naked mice with subcutaneously transplanted human bladder tumours T24 are used. On day 0, about 25 mg of a solid tumour is pushed under the skin on the left flank of the animals under peroral Forene anaesthesia and the small incision wound is closed by means of wound clamps. On day 6 after the transplant, the mice are divided randomly into groups of 6 animals and treatment is started. The treatment is carried out for 15 days with a single daily peroral or intraperitoneal administration of a compound of the formula I in dimethyl sulfoxide/Tween 80/sodium chloride solution in the various doses. Twice a week, the tumours are measured with a slide gauge and the tumour volume is calculated. In this test, peroral or intraperitoneal administration of a compound of the formula I or of a pharmaceutically acceptable salt thereof causes a significant reduction in the average tumour volume compared with the untreated control animals.

Preferred compounds of the formula I are those in which q is 1–5, $R_1$ is halogen, lower alkyl, hydroxyl or lower alkanoyloxy; lower alkoxy which is unsubstituted or substituted by hydroxyl, lower alkoxy or carboxyl; a radical of the formula —O(—CH$_2$—CH$_2$—O)$_t$—R$_6$, in which t is 2–5 and $R_6$ is hydrogen or lower alkyl; carboxyl, lower alkoxycarbonyl, piperazin-1-yl-carbonyl or carbamoyl; N-lower alkyl-carbamoyl, which is unsubstituted or substituted by hydroxyl or amino in the lower alkyl moiety; N,N-di-lower alkyl-carbamoyl, cyano, nitro, amino, lower alkanoylamino, lower alkylamino, N,N-di-lower alkylamino, aminosulfonyl or trifluoromethyl, where, if more than one radical R is present in the molecule, these can be identical to or different from one another, $R_2$ is hydrogen, carbamoyl or N-lower alkyl-carbamoyl, m and n are each 0 or 1, where m is 0 if n is 1 and m is 1 it n is 0, $R_3$ is lower alkyl or phenyl which are unsubstituted or in each case substituted by hydroxyl, lower alkoxy, amino, lower alkylamino or N,N-di-lower alkyl amino, and a) $R_4$ is hydrogen, amino, phenylamino, lower alkylamino, hydroxyl, phenoxy, lower alkoxy; an acyl radical of the part formula Z—C(=W)—, in which W is oxygen, sulfur or imino and Z is hydrogen, hydrocarbyl $R^0$, hydrocarbyloxy $R^0$—O— or an amino group of the formula $R_7(R_8)N$—, in which $R^0$ in each case is $C_1$–$C_4$alkyl, hydroxy-$C_2$–$C_{14}$alkyl, cyano-$C_1$–$C_4$alkyl, carboxy-$C_1$–$C_4$ alkyl, $C_1$–$C_4$alkoxycarbonyl-$C_1$–$C_4$alkyl, $C_3$–$C_7$alkenyl or phenyl and $R_7$ and $R_8$ independently of one another are each hydrogen, lower alkyl, ω-amino-lower alkyl, lower alkylsulfonyl or phenyl;

an aliphatic hydrocarbon radical having not more than 29 C atoms, which is substituted by halogen, amino, lower alkylamino, ω-amino-lower alkylamino, lower alkanoylamino, benzoylamino, hydroxylamino, hydroxylimino, lower alkoxy-amino, phenyloxyamino, amino-cyclohexyl-amino-, amino-phenyl-amino-, carbamoyl-amino, (N-lower alkyl-carbamoyl)-amino, (N-[ω-amino-lower alkyl]-carbamoyl)-amino, (N-phenyl-carbamoyl)-amino, thio, lower alkylthio, thiocarbamoyl, thioureido, N-lower alkyl-thioureido, N-phenyl-thioureido, guanidino, N-lower alkyl-guanidino, carboxyl, lower alkoxycarbonyl, phenyloxycarbonyl, benzyloxycarbonyl, hydroxylaminocarbonyl, carbamoyl, amidino, cyano, hydroxyl, lower alkoxy, phenyloxy, aminocarbonyl-oxy, oxo, aminosulfonyl, lower alkylsulfonyl-amino, glycylamino, alanylamino, phenylalanylamino, prolylamino, valylamino, leucylamino, isoleucylamino, serylamino, threonylamino, cysteinylamino, methionylamino, tyrosylamino, tryptophanylamino, arginylamino, histidylamino, lysylamino, glutamylamino, glutaminylamino, asparagylamino, asparaginylamino or phenylglycylamino;

benzyl, 2-phenyl-ethyl, 3-aminomethyl-benzyl, (1-hydroxycyclohex-1-yl)-methyl, (2-amino-3,5,5-trimethyl-cyclopentyl)-methyl, 1-[N-(1-carboxy-2-phenyl-ethyl)-carbamoyl]-2-carbamoyl-eth-1-yl, 1-carbamoyl-1-phenyl-methyl, 1-carbamoyl-2-(4-hydroxy-phenyl)-eth-1-yl, 1-carbamoyl-2-phenyl-eth-1-yl, 2-amino-1,2-diphenyl-eth-1-yl, 2-benzyloxycarbonyl-1-carbamoyl-eth-1-yl, 3-benzyloxycarbonyl-1-carbamoyl-prop-1-yl, 1-adamantyl-2-amino-prop-1-yl, 1-adamantyl-1-amino-prop-2-yl, (2-furyl)-methyl, (2-tetrahydrofuryl)-methyl, 2-pyrid-2-yl-ethyl, 2-piperidino-ethyl, 2-(morpholin-4-yl)-ethyl, 2-(3-indolyl)-ethyl, 2-(4-imidazolyl)-ethyl, 1-carbamoyl-2-(β-indolyl)-eth-1-yl, 1-carbamoyl-2-imidazol-4-yl-eth-1-yl, 1-carbamoyl-2-indol-3-yl-eth-1-yl, 3-aminomethyl-oxetan-3-yl-methyl, 1-(acetoxy-imino)-1-(4-amino-2-oxa-1,3-diazol-5-yl)-methyl, 2-amino-cyclohex-1-yl, 3-amino-cyclohex-1-yl, 2-aminomethyl-3,3,5-trimethyl-cyclopent-1-yl, 3-amino-adamantan-1-yl, 2-carbamoyl-bicyclo[2.2.1]hept-5-en-3-yl, 2-carbamoyl-cyclohex-1-yl, 9-amino-spiro[4.4]non-1-yl, 5-amino-2-oxa-1,3-diazol-4-yl, 4-amino-thien-3-yl, 3-carbamoyl-5-(3-[2,4-dichloro-phenyl]-1-oxo-prop-2-en-1-yl)-1,2-thiazol-4-yl, 3-carbamoyl-5-(3-[4-trifluoro-phenyl]-1-oxo-prop-2-en-1-yl)-1,2-thiazol-4-yl, 4-amino-2-(4-carboxy-butyl)-tetrahydrothiophen-3-yl, 3-amino-2-(4-carboxy-butyl)-tetrahydrothiophen-4-yl, [1,2,5]oxadiazolo[3,4-b](6-amino-pyrazin-5-yl), 2,5'-diacetyl-3-amino-thieno[2,3-b]thiophen-4'-yl or 3-amino-2,5'-dipivaloyl-thieno[2,3-b]-thiophen-4'-yl, and $R_5$ independently of $R_4$ is as defined above for $R_4$, with the exception of hydrogen, or b) $R_4$ and $R_5$ together are 1,2-ethylene, propane-1,3-diyl, butane-1,4-diyl, pentane-1,5-diyl, 3-(3-amino-propionyl)-3-aza-pentane-1,5-diyl, 1-aminomethyl-butane-1,4-diyl, 1-hydroxymethyl-butane-1,4-diyl, 3-(2-amino-ethyl)-pentane-1,5-diyl, 3-aza-pentane-1,5-diyl or 3-(2-amino-ethyl)-3-aza-pentane-1,5-diyl, and their salts.

Compounds of the formula I which are also preferred are those in which q is 1–3 and $R_4$ is hydrogen, and their salts.

Compounds of the formula I which are also preferred are those in which q is 1, $R_1$ is chlorine which is in the 3 position, $R_2$ is hydrogen, m is 0 and n is 1, $R_3$ is ethyl and a) $R_4$ is hydrogen and $R_5$ is amino, phenylamino, lower alkylamino, hydroxyl, phenoxy or lower alkoxy; an acyl radical of the part formula Z—C(=W)—, in which W is oxygen, sulfur or imino and Z is hydrogen, hydrocarbyl $R^0$, hydrocarbyloxy $R^0$—O— or an amino group of the formula $R_7(R_8)N$—, in which $R^0$ in each case is $C_1$–$C_4$alkyl, hydroxy-$C_2$–$C_{14}$alkyl, cyano-$C_1$–$C_4$alkyl, carboxy-$C_1$–$C_4$alkyl, $C_1$–$C_4$alkoxycarbonyl-$C_1$–$C_4$alkyl, $C_3$–$C_7$alkenyl or phenyl and $R_7$ and $R_8$ independently of one another are each hydrogen, lower alkyl, ωamino-lower alkyl, lower alkylsulfonyl or phenyl;

2-carbamoyl-1-carboxy-eth-1-yl, 3-amino-2-hydroxy-prop-1-yl, 3-amino-prop-1-yl, 3-amino-2,2-dimethyl-prop-1-yl, 3-amino-2-oxo-prop-1-yl, 3-amino-1-carboxy-prop-1-yl, 3-amino-3-carboxy-prop-1-yl, 1,1-dicarbamoyl-methyl, 2-carbamoyl-eth-1-yl, 3-amino-1,3-dihydroxylimino-prop-1-yl, 2-carbamoyl-1-hydroxylimino-eth-1-yl, 1-hydroxylimino-2-thiocarbamoyl-eth-1-yl, 3-amino-3-hydroxylimino-1-thio-prop-1-yl, 3-amino-pent-1-yl, 1-amino-pent-3-yl, 1-amidino-1-carbamoyl-methyl, 4-amino-1,1,1,3,5,5,5-heptafluoro-pent-2-yl, 3-amino-1,3-dicarboxy-prop-1-yl, 2-carbamoyl-1-ethoxycarbonyl-eth-1-yl, 2-amino-1,2-dithio-eth-1-yl, 2-amino-1,2-dioxo-eth-1-yl, 2-amino-2-methyl-prop-1-yl, 1-amino-2-methyl-prop-2-yl, 2-amino-prop-1-yl, 1-amino-prop-2-yl, 2-amino-eth-1-yl, 2-amino-2-carboxy-eth-1-yl, 2-amino-1-carboxy-eth-1-yl, carbamoyl-methyl, 1-carbamoyl-3-methyl-but-1-yl, 2-amino-1,2-dicarboxy-eth-1-yl, 1-carbamoyl-3-methylthio-prop-1-yl, 1-carbamoyl-2-methyl-prop-1-yl, 1-carbamoyl-eth-1-yl, 1-carbamoyl-1-cyano-methyl, 1-carbamoyl-3-carboxy-3-fluoro-prop-1-yl, 1-carbamoyl-2-carboxy-eth-1-yl, 2-amino-4-carboxy-but-1-yl, 1-amino-4-carboxy-but-2-yl, 1-carbamoyl-4-guanidino-but-1-yl, 1-carbamoyl-5-amino-pent-1-yl, 1-carbamoyl-2-hydroxy-prop-1-yl, 1-carbamoyl-2-methyl-but-1-yl, 1-carbamoyl-2-hydroxy-ethyl-yl, 1,3-dicarbamoyl-prop-1-yl, 2-amino-but-1-yl, 1-amino-but-2-yl, 1-carbamoyl-pent-1-yl, 1-carbamoyl-but-1-yl; benzyl, 2-phenyl-ethyl, 3-aminomethyl-benzyl, (1-hydroxy-cyclohex-1-yl)-methyl, (2-amino-3,5,5-trimethyl-cyclopentyl)-methyl, 1-[N-(1-carboxy-2-phenyl-ethyl)-carbamoyl]-2-carbamoyl-eth-1-yl, 1-carbamoyl-1-phenyl-methyl, 1-carbamoyl-2-(4-hydroxy-phenyl)-eth-1-yl, 1-carbamoyl-2-phenyl-eth-1-yl, 2-amino-1,2-diphenyl-eth-1-yl, 2-benzyloxycarbonyl-1-carbamoyl-eth-1-yl, 3-benzyloxycarbonyl-1-carbamoyl-prop-1-yl, 1-adamantyl-2-amino-prop-1-yl, 1-adamantyl-1-amino-prop-2-yl, (2-furyl)-methyl, (2-tetrahydrofuryl)-methyl, 2-pyrid-2-yl-ethyl, 2-piperidino-ethyl, 2-(morpholin-4-yl)-ethyl, 2-(3-indolyl)-ethyl, 2-(4-imidazolyl)-ethyl, 1-carbamoyl-2-(β-indolyl)-eth-1-yl, 1-carbamoyl-2-imidazol-4-yl-eth-1-yl, 1-carbamoyl-2-indol-3-yl-eth-1-yl, 3-aminomethyl-oxetan-3-yl-methyl, 1-(acetoxy-imino)-1-(4-amino-2-oxa-1,3-diazol-5-yl)-methyl, 2-amino-cyclohex-1-yl, 3-amino-cyclohex-1-yl, 2-aminomethyl-3,3,5-trimethyl-cyclopent-1-yl, 3-amino-adamantan-1-yl, 2-carbamoyl-bicyclo[2.2.1]hept-5-en-3-yl, 2-carbamoyl-cyclohex-1-yl, 9-amino-spiro[4.4]non-1-yl, 5-amino-2-oxa-1,3-diazol-4-yl, 4-amino-thien-3-yl, 3-carbamoyl-5-(3-[2,4-dichloro-phenyl]-1-oxo-prop-2-en-1-yl)-1,2-thiazol-4-yl, 3-carbamoyl-5-(3-[4-trifluoro-phenyl]-1-oxo-prop-2-en-1-yl)-1,2-thiazol-4-yl, 4-amino-2-(4-carboxy-butyl)-tetrahydrothiophen-3-yl, 3-amino-2-(4-carboxy-butyl)-tetrahydrothiophen-4-yl, [1,2,5]oxadiazolo[3,4-b](6-amino-pyrazin-5-yl), 2,5'-diacetyl-3-amino-thieno[2,3-b]thiophen-4'-yl or 3-amino-2,5'-dipivaloyl-thieno[2,3-b]thiophen-4'-yl, or b) $R_4$ and $R_5$ together are 1,2-ethylen, propane-1,3-diyl, butane-1,4-diyl, pentane-1,5-diyl, 3-(3-amino-propionyl)-3-aza-pentane-1,5-diyl, 1-aminomethyl-butane-1,4-diyl, 1-hydroxy-methyl-butane-1,4-diyl, 3-(2-amino-ethyl)-pentane-1,5-diyl, 3-aza-pentane-1,5-diyl or 3-(2-amino-ethyl)-3-aza-pentane-1,5-diyl, and their salts.

Particularly preferred compounds of the formula I are those in which q is 1–3, $R_1$ is halogen, lower alkyl, lower alkoxy, cyano, nitro, amino, trifluoroacetyl-amino or benzyl-oxycarbonylamino; benzoylamino which is unsubstituted or substituted by chlorine in the phenyl moiety; N-lower alkyl-carbamoyl which is unsubstituted in the lower alkyl moiety or substituted by hydroxyl; or trifluoromethyl, where, if more than one radical R is present in the molecule, these can be identical to or different from one another, $R_2$ is hydrogen, m and n are each 0 or 1, where m is 0 if n is 1 and m is 1 if n is 0, $R_3$ is lower alkyl which is unsubstituted or substituted by hydroxyl and a) $R_4$ is hydrogen, lower alkyl or hydroxy-lower alkyl and $R_5$ is cyclohexyl, lower alkyl-cyclohexyl, hydroxy-cyclohexyl, amino-cyclohexyl, amino-phenyl, hydroxymethyl-cyclopentyl, adamantyl or amino; or lower alkyl which is substituted by amino, lower alkanoylamino, lower alkylamino, ω-amino-lower alkylamino, hydroxyl, lower alkoxy, phenyl, amino-phenyl, aminomethyl-phenyl, 2-furyl, 2-tetrahydrofuryl, 2-pyridyl, piperidino, morpholin-4-yl, 3-indolyl, mercapto, 1-hydroxy-cyclohex-1-yl, cyano, carbamoyl or by 4-imidazolyl; or b) $R_4$ and $R_5$ together are an alkylene or alkenylene radical which has not more than 10 C atoms in the alkylene or alkenylene moiety and is unsubstituted or substituted by cyano, hydroxyl, cyclohexylaminocarbonyl, tolylaminocarbonyl, 1-hydroxy-1-(methoxyphenylamino)-methyl, lower alkylamino-carbonyl, lower alkylamino-thiocarbonyl, car bamoyl, lower alkanoylamino or amino, and in which 1 C atom can be replaced by nitrogen, or a radical of the formula

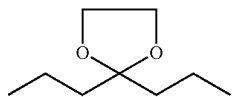

in which the two terminal bonds of the alkylene chain are free valencies, and their salts.

Especially preferred compounds of the formula I are those in which q is 1–3,

R₁ is halogen, lower alkyl or lower alkoxy; N-lower alkyl-carbamoyl, which is substituted in the lower alkyl moiety by hydroxyl; or trifluoromethyl, where, if more than one radical R is present in the molecule, these can be identical or different from one another, R₂ is hydrogen, m and n are each 0 or 1, where m is 0 if n is 1 and m is 1 if n is 0, R₃ is lower alkyl which is unsubstituted or substituted by hydroxyl and a) R₄ is hydrogen or hydroxy-lower alkyl and R₅ is 2-amino-cyclohexyl; or lower alkyl which is substituted by amino, lower alkylamino, ω-amino-lower alkylamino, hydroxyl, lower alkoxy, phenyl, 3-aminomethylphenyl, 2-furyl, 2-tetrahydrofuryl, 2-pyridyl, piperidino, morpholin-4-yl, 3-indolyl, mercapto, 1-hydroxy-cyclohex-1-yl or by 4-imidazolyl; or b) R₄ and R₅ together are an alkylene radical having not more than 10 C atoms, which is unsubstituted or substituted by hydroxyl or amino and in which 1 C atom can be replaced by nitrogen, and their salts.

The compounds of the formula I mentioned in the Examples and their pharmaceutically acceptable salts are most preferred.

The compounds of the formula I and their pharmaceutically acceptable salts are prepared by processes known per se, for example by a) reacting a compound of the formula II

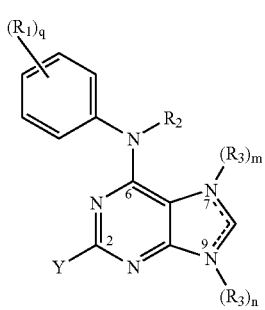

in which Y is a suitable leaving group and the other substituents and symbols are as defined above for compounds of the formula I, free functional groups present in this compound, if necessary, being protected by easily detachable protective groups, with an amine of the formula III

in which the substituents are as defined above for compounds of the formula I, free functional groups present in this compound, if necessary, being protected by easily detachable protective groups or, in accordance with the principle of latent functionality, being in a form which can be converted into the functional groups, and detaching the protective groups present and, if necessary, converting functional groups into the final form according to formula I, or b) reacting a compound of the formula V

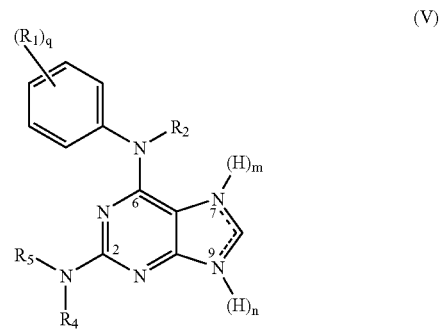

in which the substituents and symbols are as defined above for compounds of the formula I, free functional groups present in this compound, if necessary, being protected by easily detachable protective groups, with a compound of the formula VI,

in which Y is a suitable leaving group and

R₃ is as defined above for compounds of the formula I, free functional groups present in R₃, if necessary, being protected by easily detachable protective groups, and detaching the protective groups present, and, after carrying out process a) or b), if necessary for the preparation of a salt, converting a resulting free compound of the formula I into a salt or, if necessary for preparation of a free compound, converting a resulting salt of a compound of the formula I into the free compound.

The above processes are described in more detail below:

Process a)

A suitable leaving group Y in a starting material of the formula II is preferably halogen, such as bromine, iodine or, in particular, chlorine.

The end substances of the formula I can contain substituents which can also be used as protective groups in starting substances for the preparation of other end substances of the formula I. Unless otherwise evident from the context, "protective groups" in this text, are therefore only those easily detachable groups which are not a constituent of the particular desire end substance of the formula I.

Protective groups, their introduction and their detachment are described, for example, in "Protective Groups in Organic Chemistry", Plenum Press, London, N.Y. 1973, and in "Methoden der organischen Chemie" [Methods of Organic Chemistry], Houben-Weyl, 4th Edition, Volume 15/1, Georg-Thieme-Verlag, Stuttgart 1974 and in T. W. Greene, "Protective Groups in Organic Synthesis", John Wiley & Sons, New York 1981. It is characteristic of protective groups that they can be detached easily, i.e. without undesirable side reactions taking place, for example by solvolysis, reduction, photolysis or also under physiological conditions.

Protection of free functional groups in the starting material of the formula II is as a rule not necessary. If desired, free carboxyl or amino groups in the radical $R_1$ or free amino groups in the radical $R_3$ can be protected.

In a starting material of the formula III, if desired, for example, free amino groups, with the exception of the amino group participating in the reaction, or free carboxyl groups, can be present in protective form. Protection of some functional groups, for example a second amino group in the amine of the formula II, for example in the case of ethylenediamine, can be avoided by employing the amine of the formula III in a large excess. Functional groups, such as, in particular, leaving groups, for example halogen or toluenesulfonate, however, can also be present, in accordance with the principle of latent functionality, in a form which can be converted into one of the functional groups according to formula I. Thus, a protected amino group can first be set free by detaching the amino-protective group and the free amino group can then be converted into toluenesulfonate or halogen via an azide in a manner known per se.

A protected amino group can be, for example, in the form of an easily detachable acylamino, arylmethylamino, etherified mercaptoamino or 2-acyl-lower alk-1-en-yl-amino group.

In a corresponding acylamino group, acyl is, for example, the acyl radical of an organic carboxylic acid having, for example, not more than 18 carbon atoms, in particular an alkanecarboxylic acid which is unsubstituted or substituted, for example by halogen or aryl, or of a benzoic acid which is unsubstituted or substituted, for example by halogen, lower alkoxy or nitro, or of a carbonic acid half-ester. Such acyl groups are, for example, lower alkanoyl, such as formyl, acetyl or propionyl, halo-lower alkanoyl, such as 2-haloacetyl, in particular 2-chloro-, 2-bromo-, 2-iodo-, 2,2,2-trifluoro- or 2,2,2-trichloroacetyl, benzoyl which is unsubstituted or substituted, for example by halogen, lower alkoxy or nitro, for example benzoyl, 4-chlorobenzoyl, 4-methoxybenzoyl or 4-nitrobenzoyl, or lower alkoxycarbonyl which is branched in the 1 position of the lower alkyl radical or suitably substituted in the 1 or 2 position, in particular tert-lower alkoxycarbonyl, for example tert-butyloxycarbonyl, arylmethoxycarbonyl with one or two aryl radicals, which are preferably phenyl which is unsubstituted or mono- or polysubstituted, for example by lower alkyl, in particular tert-lower alkyl, such as tert-butyl, lower alkoxy, such as methoxy, hydroxyl, halogen, for example chlorine, and/or nitro, such as unsubstituted or substituted benzyloxycarbonyl, for example 4-nitro-benzyloxycarbonyl, or unsubstituted or substituted diphenylmethoxycarbonyl, for example benzhydryloxycarbonyl or di-(4-methoxyphenyl)-methoxycarbonyl, aroylmethoxycarbonyl, in which the aroyl group is preferably benzoyl which is unsubstituted or substituted, for example by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, or 2-(trisubstituted silyl)-ethoxycarbonyl, in which the substituents independently of one another are each an aliphatic, araliphatic, cycloaliphatic or aromatic hydrocarbon radical which has not more than 15 C atoms and is unsubstituted or substituted, for example substituted by lower alkyl, lower alkoxy, aryl, halogen or nitro, such as corresponding unsubstituted or substituted lower alkyl, phenyl-lower alkyl, cycloalkyl or phenyl, for example 2-tri-lower alkylsilylethoxycarbonyl, such as 2-trimethylsilyl-ethoxycarbonyl or 2-(di-n-butyl-methyl-silyl)-ethoxycarbonyl, or 2-triarylsilyl-ethoxycarbonyl, such as 2-triphenylsilylethoxycarbonyl.

In an arylmethylamino group which is a mono-, di- or, in particular, triarylmethylamino group, the aryl radicals are, in particular, substituted or unsubstituted phenyl radicals. Such groups are, for example, benzyl-, diphenylmethyl- and, in particular, tritylamino.

An etherified mercapto group in an amino group protected with such a radical is, in particular, arylthio or aryl-lower alkylthio, in which aryl is, in particular, phenyl which is unsubstituted or substituted, for example by lower alkyl, such as methyl or tert-butyl, lower alkoxy; such as methoxy, halogen, such as chlorine, and/or nitro. A corresponding amino-protective group is, for example, 4-nitrophenylthio.

In a 2-acyl-lower alk-1-en-1-yl radical which can be used as an amino-protective group, acyl is, for example, the corresponding radical of a lower alkanecarboxylic acid, of a benzoic acid which is unsubstituted or substituted, for example by lower alkyl, such as methyl or tert-butyl, lower alkoxy, such as methoxy, halogen, such as chlorine, and/or nitro, or, in particular, of a carbonic acid half-ester, such as a carbonic acid lower alkyl half-ester. Corresponding protective groups are, in particular, 1-lower alkanoyl-prop-1-en-2-yl, for example 1-acetyl-prop-1-en-2-yl, or 1-lower alkoxycarbonyl-prop-1-en-2-yl, for example 1-ethoxycarbonyl-prop-1-en-2-yl.

Preferred amino-protective groups are acyl radicals of carbonic acid half-esters, in particular tert-butyloxycarbonyl, benzyloxycarbonyl which is unsubstituted or substituted, for example as defined, for example 4-nitro-benzyloxycarbonyl, or diphenylmethoxycarbonyl, or 2-halo-lower alkoxycarbonyl, such as 2,2,2-trichlorethoxycarbonyl, and furthermore trityl or formyl.

Preferred protected carboxyl groups are, for example, tert-butoxycarbonyl, benzyloxycarbonyl or diphenylmethoxycarbonyl which are unsubstituted or substituted, or 2-trimethylsilyl-ethoxycarbonyl.

The reaction between the derivative of the formula II and the amine derivative of the formula III can be carried out in suitable inert solvents. If possible, on the basis of the physical nature of the amine of the formula III, however, the reaction is preferably carried out without a foreign solvent, and the amine of the formula III is employed in a large excess, for example a hundred times the equivalent amount, both as the reagent and as the solvent.

Depending on the nature of the specific reactants, such as, in particular, the precise nature of the leaving group Y and the reactivity of the specific amine of the formula III, the reaction is carried out at between 20° C. and 200° C., preferably between +50° C. and +180° C., for example under reflux. If Y is chlorine and the amine of the formula III is an aliphatic amine, such as ethylenediamine, the reaction is preferably carried out at between +80° C. and +150° C., for example at a bath temperature of +150° C.

The protective groups which are not a constituent of the desired end product of the formula I are detached in a manner known per se, for example by means of solvolysis, in particular hydrolysis, alcoholysis or acidolysis, or by means of reduction, in particular hydrogenolysis or chemical reduction, if necessary in stages or simultaneously.

A protected amino group is set free in a manner known per se and, depending on the nature of the protective groups, in diverse manners, preferably by means of solvolysis or reduction. 2-Halo-lower alkoxycarbonylamino (if appropriate after conversion of a 2-bromo-lower alkoxycarbonylamino group into a 2-iodo-lower alkoxycarbonylamino group), aroylmethoxycarbonylamino or 4-nitrobenzyloxycarbonylamino can be split, for example, by treatment with a suitable chemical reducing agent, such as zinc in the presence of a suitable carboxylic acid, such as aqueous acetic acid. Aroylmethoxycarbonylamino can also be split by treatment with a nucleophilic, preferably salt-forming reagent, such as sodium thiophenolate, and 4-nitro-benzyloxycarbonylamino can also be split by treatment with an alkali metal dithionite, for example sodium dithionite. Substituted or unsubstituted diphenylmethoxycarbonylamino, tert-lower alkoxycarbonylamino or 2-trisubstituted silylethoxycarbonylamino can be split by treatment with a suitable acid, for example formic or trifluoroacetic acid, substituted or unsubstituted benzyloxycarbonylamino can be split, for example, by means of hydrogenolysis, i.e. by treatment with hydrogen in the presence of a suitable hydrogenation catalyst, such as a palladium catalyst, and triarylmethylamino or formylamino can be split, for example, by treatment with an acid, such as a mineral acid, for example hydrochloric acid, or an organic acid, for example formic, acetic or trifluoroacetic acid, if appropriate in the presence of water, and an amino group protected by an organic silyl group can be set free, for example, by means of hydrolysis or alcoholysis. An amino group protected by 2-haloacetyl, for example 2-chloroacetyl, can be set free by treatment with thiourea in the presence of a base or with a thiolate salt, such as an alkali metal thiolate, of urea and subsequent solvolysis, such as alcoholysis or hydrolysis, of the condensation product formed. An amino group protected by 2-substituted silylethoxycarbonyl can also be converted into the free amino group by treatment with a hydrofluoric acid salt which supplies fluoride anions.

The starting material of the formula II in which Y is chlorine is obtained in two stages as follows:

In the first stage, 2,6-dichloro-purine, which is commercially obtainable (for example from Lancaster, Aldrich or Fluka) and is in the form of a mixture of the tautomeric forms 2,6-dichloro-9H-purine and 2,6-dichloro-7H-purine, is reacted with an amine of the formula IV

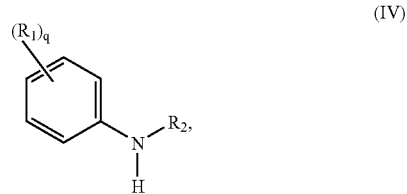

(IV)

in which q, $R_1$ and $R_2$ are as defined above, to give a compound of the formula VII

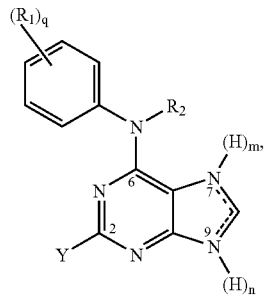

(VII)

in which Y is chlorine and the other substituents and symbols are as defined for formula I. This reaction is carried out in an inert organic solvent, such as, in particular, an alkanol, for example pentanol, preferably at a temperature between room temperature and +150° C., for example at a bath temperature of 100° C., an excess, for example 3–4 times the equivalent amount, of the amine of the formula IV preferably being employed.

In the second stage, the compound of the formula VII is reacted with a compound of the formula VI analogously to process b) to give a compound of the formula II in which Y is chlorine.

The starting material of the formula II in which Y is another leaving group, i.e. different from chlorine, is obtained in an analogous manner.

Process b)

In a starting material of the formulae V or VI, if desired, for example, free amino groups can be present in protected form.

A suitable leaving group Y in a starting material of the formula VI is preferably halogen, such as chlorine, bromine or, in particular, iodine.

The reaction between the derivatives of the formulae V and VI is carried out in a suitable inert solvent, such as, preferably, dimethylformamide or a mixture of dimethylformamide and water, preferably in a volume ratio of 9:1, and preferably in the presence of potassium carbonate or caesium carbonate, for example twice the molar amount of caesium carbonate, compared with the amount of the compound of the formua V, preferably at a reaction temperature of between 0° C. and 150° C., for example at room temperature. The derivative of the formula VI is preferably employed in an excess here, for example five times the molar amount.

The starting material of the formula V is obtained from a compound of the formula VIII with an amine of the formula III analogously to process a).

General Process Conditions:

Free compounds of the formula I which are obtainable by the process and have salt-forming properties can be converted into their salts in a manner known per se, for example by treatment with acids or suitable derivatives thereof, for example by addition of the acid in question to the compound of the formula I dissolved in a suitable solvent, for example an ether, such as a cyclic ether, in particular dioxane, and especially tetrahydrofuran. Compounds of the formula I with acid groups, for example free carboxyl groups, are treated, for example, with a suitable base, for example a hydroxide, carbonate or bicarbonate, for salt formation.

Isomer mixtures obtained according to the invention can be separated into the individual isomers in a manner known per se, for example racemates can be separated by formation of salts with optically pure salt-forming reagents and preparation of the diastereomer mixture thus obtained, for example by means of fractional crystallization.

The abovementioned reactions can be carried out under reaction conditions known per se, in the absence or, usually, presence of solvents or diluents, preferably those which are inert towards the reagents used and dissolve these, in the absence or presence of catalysts, condensation agents (for example phosphorus pentoxide) or neutralizing agents, for example bases, in particular nitrogen bases, such as triethylamine hydrochloride, depending on the nature of the reaction and/or of the reaction participants, at a reduced, normal or elevated temperature, for example in the temperature range from about −80° C. to about 200° C., preferably from about −20° C. to about 150° C., for example at the boiling point of the solvent used, under atmospheric pressure or in a closed vessel, if appropriate under pressure, and/or in an inert atmosphere, for example under a nitrogen atmosphere.

The reaction conditions stated specifically in each case are preferred.

Solvents and diluents are, for example, water, alcohols, for example lower alkylhydroxides, such as methanol, ethanol, propanol or, in particular, butanol, diols, such as ethylene glycol, triols, such as glycerol, or aryl alcohols, such as phenol, acid amides, for example carboxylic acid amides, such as dimethylformamide, dimethylacetamide or 1,3-dimethyl-3,4,5,6-tetrahydro-2(1H)-pyrimidinone (DMPU), carboxylic acids, in particular formic acid or acetic acid, amides of inorganic acids, such as hexamethylphosphoric acid triamide, ethers, for example cyclicethers, such as tetrahydrofuran or dioxane, or acyclic ethers, such as diethyl ether or ethylene glycol dimethyl ether, halogenated hydrocarbons, such as halo-lower alkanes, for example methylene chloride or chloroform, ketones, such as acetone, nitrites, such as acetonitrile, acid anhydrides, such as acetic anhydride, esters, such as ethyl acetate, bisalkanesulfines, such as dimethyl sulfoxide, nitrogen-containing heterocyclic compounds, such as pyridine, hydrocarbons, for example lower alkanes, such as heptane, or aromatics, such as benzene, toluene or xylene(s), or mixtures of these solvents, it being possible for the suitable solvents to be chosen in each case for the abovementioned reactions.

The customary processes are used for working up the compounds of the formula I which can be obtained or their salts, for example solvolysis of excess reagents; recrystallization; chromatography, for example partition, ion or gel chromatography; partition between an inorganic and organic solvent phase; one or several extractions, in particular after acidification or increasing the basicity or the salt content; drying over hygroscopic salts; digestion; filtration; washing; dissolving; evaporation (if necessary in vacuo or under a high vacuum); distillation; crystallization, for example of the resulting compounds in the form of an oil or from the mother liquor, it also being possible for the product to be seeded with a crystal of the end product; or a combination of two or more of the working up steps mentioned, which can also be employed repeatedly.

Starting materials and intermediates can be used in the pure form for example after working up, as mentioned last, in partly purified form or else, for example, directly as a crude product.

As a result of the close relationship between the compounds of the formula I in the free form and in the form of salts, the free compounds and their salts above and below are to be understood appropriately and expediently, where appropriate, as also meaning the corresponding salts or free compounds if the compounds contain salt-forming groups.

The compounds, including their salts, can also be obtained in the form of hydrates, or their crystals can include, for example, the solvent used for the crystallization.

Those starting substances which lead to the novel compounds of the formula I described above as particularly valuable are preferably employed in the process of the present invention.

The invention also relates to those embodiment forms of the process in which a compound obtainable as an intermediate at any process stage is used as the starting substance and the missing process steps are carried out, or in which a starting substance is formed under the reaction conditions or is used in the form of a derivative, for example a salt thereof.

The invention also relates to the compounds of the formula II

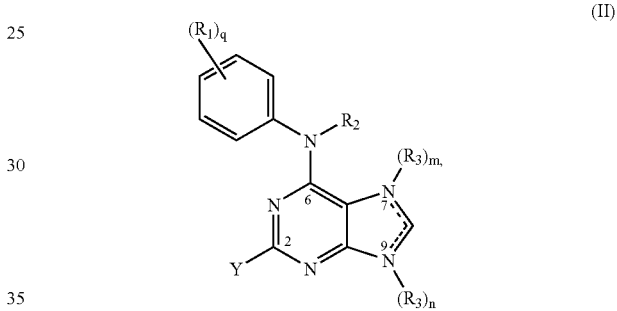

in which Y is a suitable leaving group and the other substituents and symbols are as defined above for compounds of the formula I, free functional groups therein being protected, if necessary, by easily detachable protective groups, which can be used as starting material for the preparation of the compounds of the formula I.

The invention also relates to the compounds of the formula V

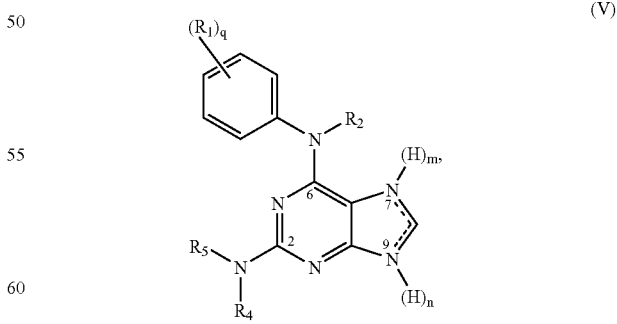

in which the substituents and symbols are as defined above for compounds of the formula I, free functional groups present therein being protected, if necessary, by easily detachable protective groups, as starting material for the preparation of the compounds of the formula I.

The present invention also relates to pharmaceutical compositions which comprise one of the compounds of the formula I as active ingredient and can be used, in particular, for treatment of the abovementioned diseases. Particularly preferred compositions are those for enteral, such as nasal, buccal, rectal or, in particular, oral, as well as for parenteral, such as intravenous, intramuscular or subcutaneous, administration to warm-blooded animals, in particular humans. The compositions comprise the active ingredient by itself or, preferably, together with a pharmaceutically acceptable carrier. The dosage of the active ingredient depends on the disease to be treated and on the species, age, weight and individual state thereof, individual pharmacokinetic circumstances of the disease to be treated and the mode of administration.

The invention also relates to pharmaceutical compositions for use in a method for therapeutic treatment of the human or animal body, a process for the preparation thereof (in particular as compositions for tumour treatment) and a method for treatment of tumour diseases, in particular those mentioned above.

A pharmaceutical composition which is suitable for administration to a warm-blooded animal, in particular humans, suffering from a disease which responds to inhibition of a protein kinase, for example psoriasis or a tumour, and comprises a compound of the formula I or a salt thereof, if salt-forming groups are present, in an amount effective for inhibition of the protein kinase, together with at least one pharmaceutically acceptable carrier.

The pharmaceutical compositions comprise about 1% to about 95% of the active ingredient, single-dose forms of administration preferably comprising about 20% to about 90% of the active ingredient and administration forms which are not single-dose preferably comprising about 5% to about 20% of the active ingredient. Unit dose forms are, for example, coated tablets, tablets, ampoules, vials, suppositories or capsules. Other forms of administration are, for example, ointments, creams, pastes, foams, tinctures, lipsticks, drops, sprays, dispersions and the like.

Examples are capsules containing from about 0.05 g to about 1.0 g of the active ingredient.

The pharmaceutical compositions of the present invention are prepared in a manner known per se, for example by means of conventional mixing, granulating, coating, dissolving or lyophilizing processes.

Preferably, solutions of the active ingredient, and in addition also suspensions or dispersions, especially isotonic aqueous solutions, dispersions or suspensions, are used, it being possible for these to be prepared before use, for example in the case of lyophilized compositions which comprise the active substance by itself or together with a carrier, for example mannitol. The pharmaceutical compositions can be sterilized and/or comprise excipients, for example preservatives, stabilizers, wetting agents and/or emulsifiers, solubilizing agents, salts for regulating the osmotic pressure and/or buffers, and they are prepared in a manner known per se, for example by means of conventional dissolving or lyophilizing processes. The solutions or suspensions mentioned can comprise viscosity-increasing substances, such as sodium carboxymethylcellulose, carboxymethylcellulose, dextran, polyvinylpyrrolidone or gelatin.

Suspensions in oil comprise, as the oily component, the vegetable, synthetic or semisynthetic oils customary for injection purposes. Oils which may be mentioned are, in particular, liquid fatty acid esters which contain, as the acid component, a long-chain fatty acid having 8–22, in particular 12–22, carbon atoms, for example lauric acid, tridecylic acid, myristic acid, pentadecylic acid, palmitic acid, margaric acid, stearic acid, arachidinic acid, behenic acid or corresponding unsaturated acids, for example oleic acid, elaidic acid, euric acid, brasidic acid or linoleic acid, if appropriate with the addition of antioxidants, for example vitamin E, β-carotene or 3,5-di-tert-butyl-4-hydroxytoluene. The alcohol component of these fatty acid esters has not more than 6 carbon atoms and is a mono- or polyhydric, for example mono-, di- or trihydric, alcohol, for example methanol, ethanol, propanol, butanol, or pentanol, or isomers thereof, but in particular glycol and glycerol. Fatty acid esters are therefore, for example: ethyl oleate, isopropyl myristate, isopropyl palmitate, "Labrafil M 2375" (polyoxyethylene glycerol trioleate from Gattefossé, Paris), "Labrafil M 1944 CS" (unsaturated polyglycolated glycerides prepared by an alcoholysis of apricot kernel oil and made up of glycerides and polyethylene glycol esters; Gattefossé, France), "Labrasol" (saturated polyglycolated glycerides, prepared by alcoholysis of TCM and made up of glycerides and polyethylene glycol esters; Gattefossé, France) and/or "Miglyol 812" (triglyceride of saturated fatty acids of chain length $C_8$ to $C_{12}$ from Hüls AG, Germany), and in particular vegetable oils, such as cottonseed oil, almond oil, olive oil, castor oil, sesame oil, soybean oil and, in particular, groundnut oil.

The preparation of the injection compositions is carried out in the customary manner under sterile conditions, as are bottling, for example in ampoules or vials, and closing of the containers.

For example, pharmaceutical compositions for oral use can be obtained by combining the active ingredient with one or more solid carriers, if appropriate granulating the resulting mixture, and, if desired, processing the mixture or granules to tablets or coated tablet cores, if appropriate by addition of additional excipients.

Suitable carriers are, in particular, fillers, such as sugars, for example lactose, sucrose, mannitol or sorbitol, cellulose preparations and/or calcium phosphates, for example tricalcium phosphate, or calcium hydrogen phosphate, and furthermore binders, such as starches, for example maize, wheat, rice or potato starch, methylcellulose, hydroxypropylmethylcellulose, sodium carboxymethylcellulose and/or polyvinylpyrrolidone, and/or, if desired, disintegrators, such as the abovementioned starches, and furthermore carboxymethyl-starch, crosslinked polyvinylpyrrolidone, alginic acid or a salt thereof, such as sodium alginate. Additional excipients are, in particular, flow regulators and lubricants, for example silicic acid, talc, stearic acid or salts thereof, such as magnesium stearate or calcium stearate, and/or polyethylene glycol, or derivatives thereof.

Coated tablet cores can be provided with suitable coatings which, if appropriate, are resistant to gastric juice, the coatings used being, inter alia, concentrated sugar solutions, which, if appropriate, comprise gum arabic, talc, polyvinylpyrrolidone, polyethylene glycol and/or titanium dioxide, coating solutions in suitable organic solvents or solvent mixtures or, for the preparation of coatings which are resistant to gastric juice, solutions of suitable cellulose preparations, such as acetylcellulose phthalate or hydroxypropylmethylcellulose phthalate. Dyes or pigments can be admixed to the tablets or coated tablet coatings, for example for identification or for characterization of different doses of active ingredient.

Pharmaceutical compositions which can be used orally are also hard capsules of gelatin and soft, closed capsules of gelatin and a plasticizer, such as glycerol or sorbitol. The hard capsules can contain the active ingredient in the form of granules, for example mixed with fillers, such as maize starch, binders and/or lubricants, such as talc or magnesium stearate, and if appropriate stabilizers. In soft capsules, the active ingredient is preferably dissolved or suspended in suitable liquid excipients, such as greasy oils, paraffin oil or liquid polyethylene glycols or fatty acid esters of ethylene glycol or propylene glycol, it likewise being possible to add stabilizers and detergents, for example of the polyoxyethylene sorbitan fatty acid ester type.

Other oral forms of administration are, for example, syrups prepared in the customary manner, which comprise the active ingredient, for example, in suspended form and in a concentration of about 5% to 20%, preferably about 10%, or in a similar concentration which results in a suitable individual dose, for example, when 5 or 10 ml are measured out. Other forms are, for example, also pulverulent or liquid concentrates for preparing of shakes, for example in milk. Such concentrates can also be packed in unit dose quantities.

Pharmaceutical compositions which can be used rectally are, for example, suppositories which comprise a combination of the active ingredient with a suppository base. Suitable suppository bases are, for example, naturally occurring or synthetic triglycerides, paraffin hydrocarbons, polyethylene glycols or higher alkanols.

Compositions which are suitable for parenteral administration are, in particular, aqueous solutions of an active ingredient in water-soluble form, for example of a water-soluble salt, or aqueous injection suspensions, which comprise viscosity-increasing substances, for example sodium carboxymethylcellulose, sorbitol and/or dextran, and if appropriate stabilizers. The active ingredient can also be present here in the form of a lyophilizate, if appropriate together with excipients, and be dissolved before parenteral administration by addition of suitable solvents.

Solutions such as are used, for example, for parenteral administration can also be used as infusion solutions.

Preferred preservatives are, for example, antioxidants, such as ascorbic acid, or microbicides, such as sorbic acid or benzoic acid.

Ointments are oil-in-water emulsions which comprise not more than 70%, but preferably 20–50%, of water or aqueous phase. The fatty phase is, in particular, hydrocarbons, for example vaseline, paraffin oil or hard paraffins, which preferably comprise suitable hydroxy compounds, such as fatty alcohols or esters thereof, for example cetyl alcohol or wool wax alcohols, such as wool wax, to improve the water-binding capacity. Emulsifiers are corresponding lipophilic substances, such as sorbitan fatty acid esters (Spans), for example sorbitan oleate and/or sorbitan isostearate. Additives to the aqueous phase are, for example, humectants, such as polyalcohols, for example glycerol, propylene glycol, sorbitol and/or polyethylene glycol, or such as preservatives and odoriferous substances.

Fatty ointments are anhydrous and comprise, as the base, in particular, hydrocarbons, for example paraffin, vaseline or paraffin oil, and furthermore naturally occurring or semi-synthetic fats, for example coconut-fatty acid triglycerides, or, preferably, hydrogenated oils, for example hydrogenated groundnut or castor oil, and furthermore fatty acid partial esters of glycerol, for example glycerol mono- and/or distearate, and, for example, the fatty alcohols, emulsifiers and/or additives mentioned in connection with the ointments which increase uptake of water.

Creams are oil-in-water emulsions which comprise more than 50% of water. Oily bases used are, in particular, fatty alcohols, for example lauryl, cetyl or stearyl alcohol, fatty acids, for example palmitic or stearic acid, liquid to solid waxes, for example isopropyl myristate, wool wax or beeswax, and/or hydrocarbons, for example vaseline (petrolatum) or paraffin oil. Emulsifiers are surface-active substances with predominantly hydrophilic properties, such as corresponding nonionic emulsifiers, for example fatty acid esters of polyalcohols or ethyleneoxy adducts thereof, such as polyglyceric acid fatty acid esters or polyethylene sorbitan fatty acid esters (Tweens), and furthermore polyoxyethylene fatty alcohol ethers or polyoxyethylene fatty acid esters, or corresponding ionic emulsifiers, such as alkali metal salts of fatty alcohol sulfates, for example sodium lauryl sulfate, sodium cetyl sulfate or sodium stearyl sulfate, which are usually used in the presence of fatty alcohols, for example cetyl alcohol or stearyl alcohol. Additions to the aqueous phase are, inter alia, agents which prevent the creams from drying out, for example polyalcohols, such as glycerol, sorbitol, propylene glycol and/or polyethylene glycols, and furthermore preservatives and odoriferous substances.

Pastes are creams and ointments having secretion-absorbing powder constituents, such as metal oxides, for example titanium oxide or zinc oxide, and furthermore talc and/or aluminium silicates, which have the task of binding the moisture or secretions present.

Foams are administered from pressurized containers and are liquid oil-in-water emulsions present in aerosol form, halogenated hydrocarbons, such as chlorofluoro-lower alkanes, for example dichlorodifluoromethane and dichlorotetrafluoroethane, or, preferably, non-halogenated gaseous hydrocarbons, air, $N_2O$ or carbon dioxide being used as the propellant gases. The oily phases used are, inter alia, those mentioned above for ointments and creams, and the additives mentioned there are likewise used.

Tinctures and solutions usually comprise an aqueous-ethanolic base to which, inter alia, polyalcohols, for example glycerol, glycols and/or polyethylene glycol, as humectants for reducing evaporation, and re-oiling substances, such as fatty acid esters with lower polyethylene glycols, i.e. lipophilic substances which are soluble in the aqueous mixture as a substitute for the fatty substances removed from the skin with the ethanol, and, if necessary, other excipients and additives, are admixed.

The invention also relates to a process or method for treatment of the disease states mentioned above, in particular those which respond to inhibition of $p34^{cdc2}$/cyclin $B^{cdc13}$ kinase. The compounds of the formula I can be administered prophylactically or therapeutically as such or in the form of pharmaceutical compositions, preferably in an amount which is effective against the diseases mentioned, to a warm-blooded animal, for example a human, requiring such treatment, the compounds being used, in particular, in the form a pharmaceutical compositions. A daily dose of about 0.1 to about 5 g, preferably about 0.5 g to about 2 g, of a compound of the present invention is administered here for a body weight of about 70 kg.

The following Examples serve to illustrate the invention without limiting the scope thereof.

The short names and abbreviations used have the following meanings:

| Abbreviations: | |
|---|---|
| abs. | absolute (anhydrous) |
| APCI-MS: | "atmospheric pressure chemical ionization" mass spectrum |
| TLC-$R_f$ | $R_f$ value according to thin layer chromatography |
| DMF | dimethylformamide |
| DMPU | 1,3-dimethyl-3,4,5,6-tetrahydro-2(1H)-pyrimidinone |
| DMSO | dimethyl sulfoxide |
| EI-MS | electron impact ionization mass spectroscopy |
| sat. | saturated |
| h | hour(s) |
| HPLC | high pressure liquid chromatography |
| HV | high vacuum |
| min | minute(s) |
| FAB-MS | "Fast Atom Bombardment" mass spectroscopy |
| MPLC | column chromatography |
| MS | mass spectroscopy |
| RT | room temperature |
| RE | rotary evaporator |
| m.p. | melting point |
| Brine | saturated sodium chloride solution |
| TFA | trifluoroacetic acid |
| THF | tetrahydrofuran |

| Abbreviations for the NMR spectra data | |
|---|---|
| b | broad |
| d | doublet |
| J | coupling constant |
| m | multiplet |
| q | quartet |
| s | singlet |
| t | triplet |

Mobile Phases (Gradients):

HPLC Gradients:

$Grad_{20/1}$ 20%→100% a) in b) over a period of 11 minutes, then 5 minutes in 100% b).

$Grad_{20/2}$ 20%→100% a) in b) over a period of 20 minutes, then 8 minutes in 100% b).

$Grad_{20/3}$ 20%→100% a) in b) over a period of 13 minutes, then 5 minutes in 100% b).

Mobile phase a): acetonitrile+0.1% TFA; mobile phase b): Water. Column (250×4.6 mm) filled with "reversed phase" material $C_{18}$-Nucleosil® (5 µm average particle size, silica gel derivatized covalently with octadecylsilanes, Macherey & Nagel, Düren, Germany). Detection by UV absorption at 254 nm. The retention times ($t_{ret}$) are stated in minutes. Flow rate 1 ml/minute.

EXAMPLE 1

250 mg (0.81 mmol) of 2-chloro-6-(3-chloro-phenyl-amino)-9-ethyl-9H-purine are dissolved in 5.8 ml (97 mmol) of ethylenediamine and the solution is heated under reflux for 3 hours (oil bath temperature of 150° C.). After cooling to room temperature, the reaction mixture is taken up in ethyl acetate (250 ml) and extracted with water (150 ml). The aqueous phase is extracted twice with ethyl acetate and the combined organic extracts are washed successively with saturated sodium bicarbonate solution, water and saturated sodium chloride solution and dried over magnesium sulfate. After filtration, the filtrate is concentrated under reduced pressure at 35° C. and the residue is dried under an HV. The crude product is recrystallized from diethyl ether. 2-(2-Amino-ethyl-amino)-6-(3-chloro-phenylamino)-9-ethyl-9H-purine is obtained; $R_f$=0.22 (methylene chloride:methanol:concentrated aqueous ammonium hydroxide solution=900:100:1); FAB-MS: $(M+H)^+$=322; m.p. 79–80° C.

The starting material is obtained as follows:

Stage 1.1: 1.4 ml (13 mmol) of 3-chloro-aniline are added to a suspension of 650 mg (3.44 mmol) of 2,6-dichloro-purine in 5 ml of 1-pentanol. The reaction mixture is stirred at 100° C. (oil bath temperature) for 3 hours. After cooling to room temperature, the mixture is diluted with isopropanol and stirred at 10° C. for 90 minutes. The precipitate is filtered off and rinsed with isopropanol and diethyl ether. The crystals are partitioned between 50 ml of 2 N (two normal) sodium hydroxide solution, 100 ml of water and 700 ml of ethyl acetate. The aqueous phase is subsequently extracted twice with ethyl acetate. The combined organic extracts are washed twice with water and once with saturated sodium chloride solution and dried over sodium sulfate. After filtration, the filtrate is concentrated under reduced pressure. The crude product is stirred with diethyl ether and the crystals are dried at 50° C. under an HV. 2-Chloro-6-(3-chloro-phenyl-amino)-purine is obtained; $R_f$=0.47 (ethyl acetate:hexane=3:1); APCI-MS: $(M+H)^+$=280; HPLC: $t_{ret}$(grad 20/1)=10.26 minutes.

Stage 1.2: 676 mg (2.413 mmol) of 2-chloro-6-(3-chloro-phenyl-amino)-purine are dissolved in 10 ml of abs. DMF by means of gentle heating. 375 mg (2.713 mmol) of potassium carbonate, followed by 0.97 ml (12.01 mmol) of ethyl iodide are added at room temperature. The reaction mixture is stirred at room temperature for 2 hours. When the reaction is complete, the reaction mixture is poured onto ice/water (60 ml) and stirred for 10 minutes. The inhomogeneous mixture is extracted three times with ethyl acetate. The combined organic extracts are washed twice with water and once with saturated sodium chloride solution and dried over magnesium sulfate. After filtration, the filtrate is concentrated under reduced pressure at 35° C. and dried under an HV. The resulting crude product (crystalline oil) is purified by crystallization from diethyl ether/hexane. 2-Chloro-6-(3-chloro-phenyl-amino)-9-ethyl-9H-purine is obtained; $R_f$=0.55 (ethyl acetate:hexane=3:1); APCI-MS: $(M+H)^+$=308; HPLC: $t_{ret}$(grad 20/1)=12.40 minutes; m.p. 127–128° C.

EXAMPLE 2

Analogously to Example 1, 6-(3-chloro-phenylamino)-2-(di-[2-hydroxy-ethyl]-amino)-9-ethyl-9H-purine is obtained from 250 mg (0.81 mmol of 2-chloro-6-(3-chloro-phenyl-amino)-9-ethyl-9H-purine [described in Stage 1.1] and 10 g (95 mmol) of diethanolamine; $R_f$=0.29 (methylene chloride:methanol:concentrated aqueous ammonium hydroxide solution=900:100:1); FAB-MS: $(M+H)^+$=377; m.p. 148–149° C.

EXAMPLE 3

Analogously to Example 1, 2-(cis-2-amino-cyclohexyl-amino)-6-(3-chloro-phenyl-amino)-9-ethyl-9H-purine is obtained from 250 mg (0.81 mmol) of 2-chloro-6-(3-chloro-phenyl-amino)-9-ethyl-9H-purine [described in Stage 1.1] and 5 ml (43 mmol) of (d,l)-cis-1,2-diamino-cyclohexane; $R_f$=0.31 (methylene chloride:methanol:concentrated aqueous ammonium hydroxide solution=900:100:1); FAB-MS: (M+H)⁺=386; m.p. 111–112° C.

EXAMPLE 4

200 mg (0.58 mmol) of 2-chloro-6-(3-chloro-phenyl-amino)-9-isopropyl-9H-purine are dissolved in 6 ml (90 mmol) of ethylenediamine and the mixture is heated under reflux for 3 hours (oil bath temperature of 150° C.). After cooling to room temperature, the reaction mixture is taken up in 250 ml of ethyl acetate and extracted with 150 ml of water. The aqueous phase is extracted twice with ethyl acetate and the combined organic extracts are washed with saturated sodium bicarbonate solution, water and saturated sodium chloride solution and dried over magnesium sulfate. After filtration, the filtrate is concentrated under reduced pressure at 35° C. and dried under an HV. 2-(2-Amino-ethylamino)-6-(3-chloro-phenyl-amino)-9-isopropyl-9H-purine is obtained; $R_f$=0.27 (methylene chloride:methanol:concentrated ammonium hydroxide solution=900:100:1); EI-MS: (M+H)⁺=346; m.p. 55–56° C.

The starting material is obtained as follows:

Stage 4.1: 500 mg (1.78 mmol) of 2-chloro-6-(3-chloro-phenyl-amino)-purine is dissolved in a mixture of 29.5 ml of DMF/water (85/15) and 5 ml of dioxane by means of gentle heating. 870 mg (2.67 mmol) of caesium carbonate, followed by 1.78 ml (17.8 mmol) of isopropyl iodide are added at room temperature. The reaction mixture is stirred at room temperature for 18 hours. To bring the reaction to completion, the reaction mixture is stirred at 45° C. for a further 24 hours. When the reaction has ended, the reaction mixture is diluted with ethyl acetate, washed with water (2 times) and saturated sodium chloride solution and dried over magnesium sulfate. After filtration, the filtrate is concentrated under reduced pressure at 35° C. and the residue is dried under an HV. The resulting crude product is purified by crystallization from diethyl ether/hexane. 2-Chloro-6-(3-chloro-phenyl-amino)-9-isopropyl-9H-purine is obtained; $R_f$=0.46 (ethyl acetate); m.p. 128–129° C.

EXAMPLE 5

Analogously to Example 1, 6-(3-chloro-phenyl-amino)-9-ethyl-2-[(R)-2-hydroxymethylpyrrolidin-1-yl]-9H-purine is obtained from 250 mg (0.81 mmol) of 2-chloro-6-(3-chloro-phenyl-amino)-9-ethyl-9H-purine [described in Stage 1.2] and 5 ml (51 mmol) of D-prolinol [i.e. R(−)-prolinol]. The product is purified by digestion with diisopropyl ether; $R_f$=0.52 (methylene chloride:methanol=9:1); m.p. 164–165° C.

EXAMPLE 6

Analogously to Example 1, 2-(3-amino-propyl-amino)-6-(3-chloro-phenyl-amino)-9-ethyl-9H-purine is obtained from 308 mg (1 mmol) of 2-chloro-6-(3-chloro-phenyl-amino)-9-ethyl-9H-purine [described in Example 1, Stage 1.2] and 10.04 ml (120 mmol) of 1,3-diamino-propane. The product is purified by digestion with diisopropyl ether; $R_f$=0.52 (methylene chloride:methanol:concenrated aqueous ammonium hydroxide solution=900:100:1); FAB-MS: (M+H)⁺=346; HPLC: $t_{ret}$(grad 20/2)=8.07 minutes.

EXAMPLE 7

Analogously to Example 1, 2-(trans-2-amino-cyclohexyl-amino)-6-(3-chloro-phenyl-amino)-9-ethyl-9H-purine is obtained from 308 mg (1 mmol) of 2-chloro-6-(3-chloro-phenyl-amino)-9-ethyl-9H-purine [described in Stage 1.2] and 6.0 ml (50 mmol) of (+/−)-trans-1,2-diamino-cyclohexane. The product is purified by digestion with diisopropyl ether; $R_f$=0.19 (ethyl acetate:methanol:concentrated aqueous ammonium hydroxide solution=900:100:1); m.p. 99.4–100.5° C.

EXAMPLE 8

Analogously to Example 1, 2-(2-hydroxy-ethyl-amino)-6-(3-chloro-phenyl-amino)-9-ethyl-9H-purine is obtained from 35 mg (0.01 mmol) of 2-chloro-6-(3-chloro-phenyl-amino)-9-ethyl-9H-purine and 1.0 ml of ethanolamine after 8 hours at 150° C.; m.p. 99–102° C.; $R_f$=0.3 (methylene chloride:methanol=9:1).

EXAMPLE 9

Analogously to Example 1, 2-(2-hydroxy-ethyl-amino)-6-(4-chloro-phenyl-amino)-7-ethyl-7H-purine is obtained from 172 mg (0.5 mmol) of 2-chloro-6-(4-chloro-phenyl-amino)-7-ethyl-7H-purine [also additionally contains 2-chloro-6-(4-chloro-phenyl-amino)-9-ethyl-9H-purine] and 1.0 ml of ethanolamine after 12 hours at 110° C.; m.p. 99–102°; $R_f$=0.2 (hexane:ethyl acetate=1:1).

The starting material is obtained as follows:

Stage 9.1: 1.0 g (5.29 mmol) of 2,6-dichloro-purine is dissolved in DMF (20 ml) and treated with 152 mg (80%, 5.3 mmol) of sodium hydride and the mixture is stirred at RT for 0.5 hours. After addition of 0.42 ml (5.3 mmol) of ethyl iodide, the mixture is stirred at 70° C. for 3 hours, diluted with ethyl acetate (100 ml) and extracted with concentrated brine. The organic phase is dried (sodium sulfate) and concentrated and the residue is chromatographed (silica gel, methylene chloride:methanol=19:1). An oily mixture comprising 2,6-dichloro-7-ethyl-7H-purine and 2,6-dichloro-9-ethyl-9H-purine is obtained.

Stage 9.2: 465 mg (2.1 mmol) of the mixture of 2,6-dichloro-7-ethyl-7H-purine and 2,6-dichloro-9-ethyl-9H-purine are stirred in butanol (5 ml) with 1.05 g (13 mmol) of 4-chloro-aniline at 100° C. for 8 hours. After crystallization from methylene chloride and diethyl ether, 2-chloro-6-(4-chloro-phenyl-amino)-7-ethyl-7H-purine and 2-chloro-6-(4-chloro-phenyl-amino)-9-ethyl-9H-purine are obtained as white crystals.

EXAMPLE 10

Analogously to Example 1, 2-benzylamino-6-(3-chloro-phenyl-amino)-9-ethyl-9H-purine is obtained from 154 mg (0.5 mmol) of 2-chloro-6-(3-chloro-phenyl-amino)-9-ethyl-9H-purine and 1.09 ml of benzylamine after 3.5 hours at 140° C.; m.p. 88–90° C., FAB-MS: (M+H)⁺=379.

EXAMPLE 11

Analogously to Example 1, 2-(2-phenyl-ethyl-amino)-6-(3-chloro-phenyl-amino)-9-ethyl-9H-purine is obtained from 189 mg (0.613 mmol) 2-chloro-6-(3-chloro-phenyl-amino)-9-ethyl-9H-purine and 1.2 ml 2-phenyl-ethylamine after 16 hours at 130° C.; m.p. 151–152° C.; FAB-MS: (M+H)⁺=393.

EXAMPLE 12

Analogously to Example 1, 2-(3-methoxy-propyl-amino)-6-(3-chloro-phenyl-amino)-9-ethyl-9H-purine is obtained from 182 mg (0.591 mmol) of 2-chloro-6-(3-chloro-phenyl-amino)-9-ethyl-9H-purine and 1.2 ml of 3-methoxy-propylamine after 3 hours at 120° C.; m.p. 93–94° C., FAB-MS: $(M+H)^+=361$.

EXAMPLE 13

Analogously to Example 1, 6-(3-chloro-phenyl-amino)-9-ethyl-2-(2-furfuryl-amino)-9H-purine is obtained from 200 mg (0.65 mmol) of 2-chloro-6-(3-chloro-phenyl-amino)-9-ethyl-9H-purine and 1.2 ml of 2-furfurylamine (freshly distilled) after 5.5 hours at 125° C.; m.p. 82–84° C.; FAB-MS: $(M+H)^+=369$.

EXAMPLE 14

Analogously to Example 1, 2-(2-piperidino-ethyl-amino)-6-(3-chloro-phenyl-amino)-9-ethyl-9H-purine is obtained from 200 mg (0.65 mmol) of 2-chloro-6-(3-chloro-phenyl-amino)-9-ethyl-9H-purine and 1.2 ml 2-piperidino-ethylamine after 2 hours at 125°; FAB-MS: $(M+H)^+=400$; $R_f=0.32$ (methylene chloride:methanol=9:1).

EXAMPLE 15

Analogously to Example 1, 2-(tetrahydrofurfuryl-amino)-6-(3-chloro-phenyl-amino)-9-ethyl-9H-purine is obtained from 200 mg (0.65 mmol) of 2-chloro-6-(3-chloro-phenyl-amino)-9-ethyl-9H-purine and 1.5 g of tetrahydrofurfurylamine after 12 hours at 100° C.; m.p. 84–86° C., FAB-MS: $(M+H)^+=373$.

EXAMPLE 16

Analogously to Example 1, 2-[2-(2-pyridyl)-ethyl-amino]-6-(3-chloro-phenyl-amino)-9-ethyl-9H-purine is obtained from 200 mg (0.65 mmol) of 2-chloro-6-(3-chloro-phenyl-amino)-9-ethyl-9H-purine and 1.2 ml of 2-(2-aminoethyl)-pyridine after 1.5 hours at 125° C.; m.p. 152–153° C., FAB-MS: $(M+H)^+=394$.

EXAMPLE 17

Analogously to Example 1, 6-(3-chloro-phenyl-amino)-2-[2-(4-morpholinyl)-ethyl-amino]-9-ethyl-9H-purine is obtained from 200 mg (0.65 mmol of 2-chloro-6-(3-chloro-phenyl-amino)-9-ethyl-9H-purine and 1.5 ml of 4-(2-aminoethyl)-morpholine after 14 hours at 100° C.; FAB-MS: $(M+H)^+=402$; $R_f=0.63$ (methylene chloride:methanol=9:1).

EXAMPLE 18

Analogously to Example 1, 2-[4-(2-amino-ethyl)-piperidin-1-yl]-6-(3-chloro-phenyl-amino)-9-ethyl-9H-purine is obtained from 200 mg (0.65 mmol) of 2-chloro-6-(3-chloro-phenyl-amino)-9-ethyl-9H-purine and 1.5 g of 4-(2-aminoethyl)-piperidine after 1.5 hours at 100° C.; m.p. 182–184° C.; FAB-MS: $(M+H)^+=400$.

EXAMPLE 19

Analogously to Example 1, 2-[4-(2-amino-ethyl)-piperazin-1-yl]-6-(3-chloro-phenyl-amino)-9-ethyl-9H-purine is obtained from 200 mg (0,65 mmol) 2-chloro-6-(3-chloro-phenyl-amino)-9-ethyl-9H-purine and 1.5 g of 1-(2-aminoethyl)-piperazine after 20 hours at 40° C.; FAB-MS: $(M+H)^+=401$; $R_f=0.48$ (methylene chloride:methanol:concentrated aqueous ammonia solution=90:10:1).

EXAMPLE 20

Analogously to Example 1, 2-[2-(3-indolyl)-ethyl-amino]-6-(3-chloro-phenyl-amino)-9-ethyl-9H-purine is obtained from 200 mg (0.65 mmol) of 2-chloro-6-(3-chloro-phenyl-amino)-9-ethyl-9H-purine and 1.5 g of tryptamine after 1.5 hours at 130° C.; m.p. 106–108° C.; FAB-MS: $(M+H)^+=432$.

EXAMPLE 21

Analogously to Example 1, 2-(2-thio-ethyl-amino)-6-(3-chloro-phenyl-amino)-9-ethyl-9H-purine is obtained from 200 mg (0.65 mmol) of 2-chloro-6-(3-chloro-phenyl-amino)-9-ethyl-9H-purine and 600 mg of cystamine in 3.0 ml of n-amyl alcohol after 20 hours at 140° C.; m.p 124–127° C., FAB-MS: $(M+H)^+=349$.

EXAMPLE 22

Analogously to Example 1, 6-(3-chloro-phenyl-amino)-2-([1-hydroxy-cyclohex-1-yl]-methylamino)-9-ethyl-9H-purine is obtained from 200 mg (0.2 mmol) of 2-chloro-9-ethyl-9H-purine and 1000 mg of 1-(aminomethyl)-cyclohexan-1-ol after 14 hours at 120°; m.p. 143–145° C., FAB-MS: $(M+H)^+401$.

EXAMPLE 23

Analogously to Example 1, 6-(3-chloro-phenylamino)-9-ethyl-2-piperazino-9H-purine is obtained from 308 mg (1 mmol) of 2-chloro-6-(3-chloro-phenyl-amino)-9-ethyl-9H-purine [described in Stage 1.2] and 258 mg (3 mmol) of piperazine in 10 ml of xylene. The product is purified by digestion with diisopropyl ether and hexane; $R_f=0.44$ (ethyl acetate:methanol:concentrated ammonium hydroxide solution=900:100:1); FAB-MS: $(M+H)^+=358$; m.p. 181.5–182.5° C.

EXAMPLE 24

200 mg (0.58 mmol) of 2-chloro-9-ethyl-6-(3-trifluoromethyl-phenyl-amino)-9H-purine and 2 ml of 3-amino-1-propanol are stirred at 140° C. for 2 h and the mixture is allowed to cool and is diluted with 60 ml of ethyl acetate. The organic phase is washed with water and dried over sodium sulfate. After removal of the solvent, the residue is recrystallized from ethyl acetate and diethyl ether. 9-Ethyl-2-(3-hydroxypropyl-amino)-6-(3-trifluoromethyl-phenyl-amino)-9H-purine is obtained; m.p. 136–137° C.; FAB-MS: $(M+H)^+=381$; $R_f=0.7$ (ethyl acetate:methanol=9:1).

The starting material is obtained as follows:

Stage 24.1: 1.9 g (10 mmol) of 2,6-dichloro-purine and 8.05 g (50 mmol) of 3-trifluoromethyl-aniline (Fluka, Buchs, Switzerland) in 60 ml of n-butanol and 3 ml of DMF are stirred at 60° C. for 6 h. 50 ml of ethyl acetate are added to the cooled reaction solution and the precipitate is filtered off and further stirred in 40 ml of isopropanol at 40° C. for 60 min. After filtration with suction and drying, 2-chloro-6-(3-trifluoromethyl-phenyl-amino)-purine is obtained; m.p. 248–250° C.; FAB-MS: $(M+H)^+=314$; $R_f=0.45$ (methylene chloride:methanol=95:5).

Stage 24.2: A mixture comprising 1 g (3.2 mmol) of 2-chloro-6-(3-trifluoromethyl-phenyl-amino)-purine, 1.7 g (5.1 mmol) of caesium carbonate and 2.1 ml (25.6 mmol) of ethyl iodide in 7 ml of dioxane/water/DMF (8:2:2) is stirred at RT for 18 h. It is then diluted with ethyl acetate and the organic phase is washed with water. This phase is separated off and dried over sodium sulfate. After removal of the solvent, the residue is recrystallized from ethyl acetate and diethyl ether. 2-Chloro-9-ethyl-6-(3-trifluoromethyl-phenyl-amino)-9H-purine is obtained; m.p. 129–130° C.; FAB-MS: $(M+H)^+=342$; $R_f=0.6$ (methylene chloride:methanol=9:1).

EXAMPLE 25

Analogously to Example 24, 9-ethyl-2-(3-hydroxy-propyl-amino)-6-[3-[(3-hydroxy-propyl)-aminocarbonyl]-2-methyl-phenyl-amino]-9H-purine is obtained from 140 mg (0.4 mmol) of 2-chloro-6-(3-ethoxycarbonyl-2-methyl-phenyl-amino)-9-ethyl-9H-purine and 1.5 ml of 3-amino-1-propanol after 4 h at 110° C.; m.p. 138–142° C.; FAB-MS: $(M+H)^+=428$; $R_f=0.7$ (methylene chloride:methanol=7:3).

The starting material is obtained as follows:

Stage 25.1: Analogously to Stage 104.1, 2-chloro-6-(3-ethoxycarbonyl-2-methyl-phenyl-amino)-purine is obtained from 1.2 g (6.4 mmol) of 2,6-dichloro-purine and 1.5 g (9.1 mmol) of ethyl 3-amino-2-methyl-benzoate (prepared by the method of Fringuelli et. al., Tetrahedron 1969, 25, 4249) in 25 ml of n-butanol after stirring at 75° C. for 48 h; m.p. 235–236° C.; FAB-MS: 318 $(M+H)^+$; $R_f=0.5$ (methylene chloride: methanol=9:1).

Stage 25.2: Analogously to Stage 24.2, 2-chloro-6-(3-ethoxycarbonyl-2-methyl-phenyl-amino)-9-ethyl-9H-purine is obtained from 500 mg (1.57 mmol) of 2-chloro-6-(3-ethoxy-carbonyl-2-methyl-phenyl-amino)-purine, 1.01 g (3.15 mmol) of caesium carbonate and 1.3 ml (15 mmol) of ethyl iodide in 20 ml of DMF/water (9:1) after 6 h at RT; m.p. 142–144° C.; FAB-MS: $(M+H)^+=346$; $R_f=0.5$ (ethyl acetate:acetone=12:1).

EXAMPLE 25

Analogously to Stage 24.2, 2-(3-hydroxy-propyl-amino)-6-(3-methoxy-phenyl-amino)-9-ethyl-9H-purine is obtained from 100 mg (0.32 mmol) of 2-(3-hydroxy-propyl-amino)-6-(3-methoxy-phenyl-amino)-purine, 208 mg (0.64 mmol) of caesium carbonate and 250 mg (1.6 mmol) of ethyl iodide in 4 ml of DMF/water (9:1) after 48 h at RT; m.p. 130–131° C.; FAB-MS: $(M+H)^+=343$; $R_f=0.55$ (methylene chloride: methanol=9:1).

The starting material is obtained as follows:

Stage 26.1: Analogously to Stage 24.1, 2-chloro-6-(3-methoxy-phenyl-amino)-purine is obtained from 1.9 g (10 mmol of 2,6-dichloro-purine and 1.5 g (12 mmol) of m-anisidine (Fluka, Buchs, Switzerland) in n-butanol/DMF (18:3) after stirring at 50° C. for 4 h; m.p. 245–246° C.; FAB-MS: $(M+H)^+=276$; $R_f=0.75$ (methylene chloride:methanol=8:2).

Stage 26.2: Analogously to Example 24, 2-(3-hydroxy-propyl-amino)-6-(3-methoxy-phenyl-amino)-purine is obtained from 0.96 g (3.5 mmol) of 2-chloro-6-(3-methoxy-phenyl-amino)-purine and 8 ml of 3-amino-1-propanol after stirring at 150° C. for 5 h; m.p. 199–200° C.; FAB-MS: $(M+H)^+=315$; $R_f=0.15$ (methylene chloride: methanol=9:1).

EXAMPLE 27

Analogously to Stage 24.2, 2-(3-hydroxy-propyl-amino)-6-(3-methoxy-phenyl-amino)-9-isopropyl-9H-purine is obtained from 180 mg (0.57 mmol) of 2-(3-hydroxy-propyl-amino)-6-(3-methoxy-phenyl-amino)-purine (cf. Stage 26.2), 372 mg (1.14 mmol) of caesium carbonate and 0.3 ml (0.003 mmol) of isopropyl iodide in 5 ml of DMF/water (9:1) after 16 h at 60° C.; m.p. 128–129° C.; FAB-MS: $(M+H)^+=357$; $R_f=0.5$ ($CH_2Cl_2$:methanol=9:1).

EXAMPLE 28

Analogously to Stage 24.2, 9-(2-hydroxy-ethyl)-2-(3-hydroxy-propyl-amino)-6-(3-methoxy-phenyl-amino)-9H-purine is obtained from 180 mg (0.57 mmol) of 2-(3-hydroxy-propyl-amino)-6-(3-methoxy-phenyl-amino)-purine (cf. Stage 26.2), 372 mg (1.14 mmol) of caesium carbonate and 0.33 ml (3 mmol) of 2-iodo-ethanol in 5 ml of DMF/water (9:1) after 18 h at 60° C.; m.p. 132–133° C.; FAB-MS: $(M+H)^+=359$; $R_f=0.5$ ($CH_2Cl_2$:methanol=9:1).

EXAMPLE 29

Analogously to Example 24, 9-ethyl-2-[2-(4-imidazolyl)-ethyl-amino]-6-(3-methoxy-phenyl-amino)-9H-purine is obtained from 91 mg (0.3 mmol) of 2-chloro-9-ethyl-6-(3-methoxy-phenyl-amino)-9H-purine and 1.1 g (10 mmol) of 2-(4-imidazolyl)-ethylamine (Fluka, Buchs, Switzerland) after 2 h at 120° C.; FAB-MS: $(M+H)^+=379$; $R_f=0.15$ ($CH_2Cl_2$:methanol=9:1).

The starting material is obtained as follows:

Stage 29.1: Analogously to Stage 24.2, 2-chloro-9-ethyl-6-(3-methoxy-phenyl-amino)-9H-purine is obtained from 1.5 g (5.44 mmol) of 2-chloro-6-(3-methoxy-phenyl-amino)-purine (cf. Stage 26.1), 8.5 g (54.4 mmol) of ethyl iodide and 2.6 g (8.1 mmol) of caesium carbonate in 45 ml of dioxane/water/DMF (8:15:85) after 6 h at RT; m.p. 158–159° C.; FAB-MS: $(M+H)^+=303$; $R_f=0.65$ ($CH_2Cl_2$:methanol=9:1).

EXAMPLE 30

Analogously to Example 24, 2-(3-hydroxy-propyl-amino)-6-(3,4,5-trimethoxy-phenyl-amino)-9-methyl-9H-purine is obtained from 70 mg (0.2 mmol) of 2-chloro-9-methyl-6-(3,4,5-trimethoxy-phenyl-amino)-9H-purine and 0.23 ml (1.5 mmol) of 3-amino-1-propanol after 2 h at 150° C.; m.p. 166–167° C.; FAB-MS: $(M+H)^+=389$; $R_f=0.35$ ($CH_2Cl_2$:methanol=9:1).

The starting material is obtained as follows:

Stage 30.1: Analogously to Stage 24.1, 2-chloro-6-(3,4,5-trimethoxy-phenyl-amino)-purine is obtained from 1.5 g (7.9 mmol) of 2,6-dichloro-purine and 1.45 g (7.9 mmol) of 3,4,5-trimethoxy-aniline (Fluka, Buchs, Switzerland); m.p. 265° C.; FAB-MS: $(M+H)^+=336$; $R_f=0.3$ ($CH_2Cl_2$:methanol=9:1).

Stage 30.2: 168 mg (0.5 mmol) of 2-chloro-6-(3,4,5-trimethoxy-phenyl-amino)-purine, 103 mg (0.75 mmol) of potassium carbonate and 0.156 ml (2.5 mmol) of methyl iodide are stirred in 3 ml of dimethylformamide at room temperature for 5 h. 30 ml of ethyl acetate are added to the slightly cloudy reaction solution and the mixture is extracted with water. The organic phase is dried over sodium sulfate. After removal of the solvent, the residue is recrystallized from ethyl acetate and diethyl ether. 2-Chloro-6-(3,4,5-trimethoxy-phenyl-amino)-9-methyl-9H-purine is obtained; FAB-MS: $(M+H)^+=350$; $R_f=0.6$ ($CH_2Cl_2$:methanol=9:1).

EXAMPLE 31

The following compounds of the formula I are obtained analogously to the processes described in this text:
a) 2-[(3-aminomethyl-phenyl)-methyl-amino]-6-(3-chloro-phenylamino)-ethyl-9H-purine,
b) 2-(2-methylamino-ethyl-amino)-6-(3-chloro-phenylamino)-9-ethyl-9H-purine and
c) 2-[2-(2-amino-ethyl-amino)-ethyl-amino]-6-(2-chloro-phenylamino)-9-ethyl-9H-purine.

EXAMPLE 32

Dry Capsules 5000 capsules, each of which contain 0.25 g of one of the compounds of the formula I mentioned in the preceding or following Examples as active ingredient, are prepared as follows:

| Composition | |
| --- | --- |
| Active ingredient | 1250 g |
| Talc | 180 g |
| Wheat starch | 120 g |
| Magnesium stearate | 80 g |
| Lactose | 20 g |

Preparation process: The powdered substances mentioned are pressed through a sieve of mesh width 0.6 mm. Portions of 0.33 g of the mixture are transferred to gelatin capsules with the aid of a capsule-filling machine.

EXAMPLE 33

Soft Capsules 5000 soft gelatin capsules, each of which contain 0.05 g of one of the compounds of the formula I mentioned in the preceding or following Examples as active ingredient are prepared as follows:

Composition

| Active ingredient | 250 g |
| --- | --- |
| Lauroglycol | 2 liters |

Preparation process: The powdered active ingredient is suspended in Lauroglykol® (propylene glycol laurate, Gattefossé S. A., Saint Priest, France) and ground in a wet-pulverizer to a particle size of about 1 to 3 μm. Portions of in each case 0.419 g of the mixture are then transferred to soft gelatin capsules by means of a capsule-filling machine.

EXAMPLE 34

Soft Capsules 5000 soft gelatin capsules, each of which contain 0.05 g of one of the compounds of the formula I mentioned in the preceding or following Examples as active ingredient, are prepared as follows:

| Composition | |
| --- | --- |
| Active ingredient | 250 g |
| PEG 400 | 1 liter |
| Tween 80 | 1 liter |

Preparation process: The powdered active ingredient is suspended in PEG 400 (polyethylene glycol of $M_r$ between about 380 and about 420, Fluka, Switzerland) and Tween® 80 (polyoxyethylene sorbitan monolaurate, Atlas Chem. Ind., Inc., USA, supplied by Fluka, Switzerland) and ground in a wet-pulverizer to a particle size of about 1 to 3 μm. Portions of in each case 0.43 g of the mixture are then transferred to soft gelatin capsules by means of a capsule-filling machine.

EXAMPLE 35

Analogously to Example 1, 2-(cis-2-amino-cyclohexyl-amino)-6-(3-chloro-phenyl-amino)-9-ethyl-9H-purine (cf. Example 3) is obtained from 539 mg (1.75 mmol) of 2-chloro-6-(3-chloro-phenyl-amino)-9-ethyl-9H-purine [described in Stage 1.2] and 3.32 ml (28.6 mmol) of cis-1,2-diamino-cyclohexane after 6 h at 150° C., in the form of the enantiomeric mixture which is split into the two enantiomers by means of high pressure liquid chromatography by a chiral stationary phase (Chiralpak® AD, silica gel, 20 μm, Daicel, Chemical Industry Tokyo, Japan). 2-[(2S,1R)-2-Amino-cyclohexyl-amino]-6-(3-chloro-phenyl-amino)-9-ethyl-9H-purine (preliminary assignment of the absolute stereochemistry);
$[a]_D^{20}=+8.6°$ [methanol, c=1] and 2-[(2R,1 S)-2-amino-cyclohexyl-amino)-6-(3-chloro-phenyl-amino)-9-ethyl-9H-purine (preliminary assignment of the absolute stereochemistry);
$[a]_D^{20}=-8.8\%$ [methanol, c=1] are obtained. The other physical data are identical to those given in Example 3.

EXAMPLE 36

Analogously to Example 1, 6-(3-chloro-phenyl-amino)-9-ethyl-2-[2-hydroxy-methyl-piperidin-1-yl]-9H-purine is obtained from 308 mg (1.00 mmol) of 2-chloro-6-(3-chloro-phenyl-amino)-3-ethyl-9H-purine [described in Stage 1.2] and 2.30 g (20 mmol) of racemic 2-piperidinemethanol after 7.75 h at 150° C.; m.p. 184° C.; FAB-MS: $(M+H)^+=387$; HPLC: $t_{ret}$ $(grad_{20/2})=14.17$ minutes.

EXAMPLE 37

Analogously to Example 1, 2-[(2R,1R)-2-amino-cyclohexyl-amino]-6-(3-chloro-phenyl-amino)-9-ethyl-9H-purine is obtained from 539 mg (1.75 mmol) of 2-chloro-6-(3-chloro-phenyl-amino)-9-ethyl-9H-purine [described in Stage 1.2] and 3.26 g (28.6 mmol) of (1R,2R)(−)-1,2-diamino-cyclohexane after 6 h at 150° C. and purification by means of column chromatography and digestion in diisopropyl ether; m.p. 151.9° C.; FAB-MS: $(M+H)^+=386$; HPLC: $t_{ret}$ $(grad_{20/2})=10.14$ minutes, $[\alpha]_D^{20}=-36.3°$ [methanol, c=1].

EXAMPLE 38

Analogously to Example 1, 2-(trans-4-amino-cyclohexyl-amino)-6-(3-chloro-phenyl-amino)-9-ethyl-9H-purine; FAB-MS: $(M+H)^+=386$; HPLC: $t_{ret}$ $(grad_{20/2})=8.47$ minutes, and 2-(cis-4-amino-cyclohexyl-amino)-6-(3-chloro-phenyl-amino)-9-ethyl-9H-purine; FAB-MS: $(M+H)^+=386$; HPLC: $t_{ret}$ $(grad_{20/2})=9.37$ minutes are obtained from 308 mg (1.00 mmol) of 2-chloro-6-(3-chloro-phenyl-amino)-9-ethyl-9H-purine [described in Stage 1.2] and 3.26 g (28.6 mmol) of 1,4-diamino-cyclohexane (cis/trans mixture) after 25 h at 100° C. and purification by means of column chromatography.

EXAMPLE 39

Analogously to Example 1, 2-(trans-3-amino-cyclohexyl-amino)-6-(3-chloro-phenyl-amino)-9-ethyl-9H-purine; FAB-MS: (M+H)$^+$=386; HPLC: $t_{ret}$ (grad$_{20/2}$)=9.32 minutes, and 2-(cis-3-amino-cyclohexyl-amino)-6-(3-chloro-phenyl-amino)-9-ethyl-9H-purine; FAB-MS: (M+H)$^+$=386; HPLC: $t_{ret}$ (grad$_{20/2}$)=9.19 minutes, are obtained from 308 mg (1.00 mmol) of 2-chloro-6-(3-chloro-phenyl-amino)-9-ethyl-9H-purine [described in Stage 1.2] and 3.26 g (28.6 mmol) of 1,3-diamino-cyclohexane (cis/trans mixture) after 13 h at 100° C. and purification by means of column chromatography.

EXAMPLE 40

Analogously to Example 1, 6-(3-chloro-phenyl-amino)-9-ethyl-2-[(S)-2-hydroxymethyl-pyrrolidin-1-yl]-9H-purine is obtained from 250 mg (0.81 mmol) of 2-chloro-6-(3-chloro-phenyl-amino)-9-ethyl-9H-purine [described in Stage 1.2] and 2.5 ml of L-prolinol [i.e. S(−)-prolinol] after 5 h at 60° C. and purification by means of column chromatography and digestion in diisopropyl ether; m.p. 169° C.; FAB-MS: (M+H)$^+$=373, HPLC: $t_{ret}$ (grad$_{20/2}$)=13.78 minutes.

EXAMPLE 41

Analogously to Example 1, 2-(trans-2-amino-cyclohexyl-amino)-6-(3-chloro-phenyl-amino)-9-ethyl-9H-purine is obtained from 539 mg (1.751 mmol) of 2-chloro-6-(3-chloro-phenyl-amino)-9-ethyl-9H-purine [described in Stage 1.2] and 3.266 g of (1S,2S)-(+)-1,2-diamino-cyclohexane after 6 h at 150° C. and purification by means of column chromatography; m.p. 152.3° C.; FAB-MS: (M+H)$^+$=386; HPLC: $t_{ret}$ (grad$_{20/2}$)=10.18 minutes.

EXAMPLE 42

Analogously to Example 1, 2-[3-amino-phenylamino]-6-(3-chloro-phenyl-amino)-9-ethyl-9H-purine is obtained from 308 mg (1.0 mmol) of 2-chloro-6-(3-chloro-phenyl-amino)-9-ethyl-9H-purine [described in Stage 1.2] and 324 mg of 1,3-phenylendiamine in 10 ml of n-butanol after 72 h at 135° C. in a glass pressure reactor and purification by means of column chromatography and digestion in diisopropyl ether; m.p. 205° C.; FAB-MS: (M+H)$^+$=380; HPLC: $t_{ret}$ (grad$_{20/2}$)=10.36 minutes.

EXAMPLE 43

Analogously to Example 1, 2-(adamant-1-ylamino)-6-(3-chloro-phenyl-amino)-9-ethyl-9H-purine is obtained from 308 mg (1.0 mmol) of 2-chloro-6-(3-chloro-phenyl-amino)-9-ethyl-9H-purine [described in Stage 1.2] and 2.27 g (15 mmol) of 1-amino-adamantane in 10 ml of n-butanol after 72 h at 150° C., followed by a further addition of 1.14 g of 1-amino-adamantane and further reaction for 24 h, after purification by means of column chromatography (MPLC); FAB-MS: (M+H)$^+$=423; HPLC: $t_{ret}$ (grad$_{20/2}$)=18.56 minutes.

EXAMPLE 44

Analogously to Example 1, 6-(3-chloro-phenyl-amino)-9-ethyl-2-([N$^1$-methyl]-2-amino-ethyl-amino)-9H-purine is obtained from 616 mg (2.0 mmol) of 2-chloro-6-(3-chloro-phenyl-amino)-9-ethyl-9H-purine [described in Stage 1.2] and 8.6 ml of N$^1$-methyl-ethylendiamine after 18 h at 45° C. and purification by means of column chromatography; m.p. 162.2° C.; FAB-MS: (M+H)$^+$=346, HPLC: $t_{ret}$ (grad$_{20/2}$) =9.50 minutes.

EXAMPLE 45

Analogously to Example 1, 2-[(R)-(−)-2-carbamoyl-pyrrolidin-1-yl]-6-(3-chloro-phenyl-amino)-9-ethyl-9H-purine is obtained from 616 mg (2.0 mmol) of 2-chloro-6-(3-chloro-phenyl-amino)-9-ethyl-9H-purine [described in Stage 1.2], 456 mg (4.0 mmol) of D-prolinamide [i.e. (R)-(−)-prolinamide] and 0.328 ml (2.2 mmol) of 1,8-diazabicyclo-[5.4.0]undec-7-ene(1.5–5)(=DBU) in 2.5 ml of dimethyl sulfoxide after 23 h at 65° C.; m.p.>230° C.; FAB-MS: (M+H)$^+$=386; HPLC: $t_{ret}$ (grad$_{20/2}$)=11.59 minutes; $[\alpha]_D^{20}$=+4.7° [DMSO, c=0.51].

EXAMPLE 46

A suspension of 56 mg (1.47 mmol) of LiAlH$_4$ in 2 ml of abs. THF is added to a suspension of 150 mg of 2-[(R)-(−)-2-carbamoyl-pyrrolidin-1-yl]-6-(3-chloro-phenyl-amino)-9-ethyl-9H-purine (cf. Example 45) in 10 ml of abs. THF and the mixture is stirred at 80° C. for 22 h. After further addition of 56 mg of LiAlH$_4$, the mixture is allowed to react further for 18 h. 5 ml of WATER are then added dropwise, with ice/water cooling, and the reaction mixture is then poured onto 50 ml of ice/water. The mixture is extracted three times with ethyl acetate. The combined organic extracts are washed twice with water and once with saturated sodium chloride solution and dried over magnesium sulfate. After filtration, the filtrate is concentrated under reduced pressure. The resulting crude product (oil) is purified by means of column chromatography and digestion in diisopropyl ether. 2-[(R)-2-Aminomethyl-pyrrolidin-1-yl]-6-(3-chloro-phenyl-amino)-9-ethyl-9H-purine is obtained; m.p. 126–129° C.; FAB-MS: (M+H)$^+$=372, HPLC: $t_{ret}$ (grad$_{20/2}$)=11.09 minutes.

EXAMPLE 47

Analogously to Example 1, 2-(2-amino-propyl-amino)-6-(3-chloro-phenyl-amino)-9-ethyl-9H-purine is obtained from 308 mg (1.0 mmol) of 2-chloro-6-(3-chloro-phenyl-amino)-9-ethyl-9H-purine [described in Stage 1.2] and 2.44 ml of 1,2-diamino-propane after 17 h at 60° C., followed by 6 h at 120° C. and purification by means of column chromatography; m.p. 119–120° C.; FAB-MS: (M+H)$^+$=346, HPLC: $t_{ret}$ (grad$_{20/2}$)=8.85 minutes.

EXAMPLE 48

Analogously to Example 1, 6-(3-chloro-phenyl-amino)-9-ethyl-2-(3-formylamino-piperidin-1-yl)-9H-purine is obtained from 308 mg (1.0 mmol) of 2-chloro-6-(3-chloro-phenyl-amino)-9-ethyl-9H-purine [described in Stage 1.2], 190 mg (1.1 mmol of 3-amino-piperidine dihydrochloride and 0.314 ml (2.1 mmol) of 1,8-diazabicyclo[5.4.0]undec-7-ene(1.5–5)(=DBU) in 7.5 ml of dimethylformamide in a glass pressure reactor after 40 h at 150° C. and purification by means of column chromatography (MPLC); m.p. 184.3° C.; FAB-MS: (M+H)$^+$=400; HPLC: $t_{ret}$ (grad$_{20/2}$)=12.56 minutes.

EXAMPLE 49

Analogously to Example 1, 2-[(S)-1-carbamoyl-ethylamino]-6-(3-chloro-phenyl-amino)-9-ethyl-9H-purine is obtained from 308 mg (1.0 mmol) of 2-chloro-6-(3-chlorophenyl-amino)-9-ethyl-9H-purine [described in Stage 1.2], 137 mg (1.1 mmol) of L-alaninamide hydrochloride [i.e. (S)-(+)-2-amino-propionamide] and 0.314 ml (2.1 mmol) of 1,8-diazabicyclo[5.4.0]undec-7-ene(1.5–5)(=DBU) in 3.0 ml of dimethyl sulfoxide in a glass pressure reactor after 42 h at 140° C. and purification by means of column chromatography (MPLC) and digestion in diisopropyl ether; m.p. 117–121° C.; FAB-MS: $(M+H)^+360$; HPLC: $t_{ret}$ $(grad_{20/2})$ =9.88 minutes.

EXAMPLE 50

Analogously to Example 1, 2-(2-amino-2-methyl-propylamino)-6-(3-chloro-phenyl-amino)-9-ethyl-9H-purine hydrochloride is obtained from 462 mg (1.5 mmol) of 2-chloro-6-(3-chloro-phenyl-amino)-9-ethyl-9H-purine [described in Stage 1.2] and 4.45 ml of 1,2-diamino-2-methyl-propane after 8 h at 120° C., followed by 14 h at 60° C. and purification by means of column chromatography; m.p. 196° C.; FAB-MS: $(M+H)^+=360$; HPLC: $t_{ret}$ $(grad_{20/2})$=9.27 minutes.

EXAMPLE 51

Analogously to Example 1, 6-(3-chloro-phenyl-amino)-9-ethyl-2-[imidazol-1-yl]-9H-purine is obtained from 308 mg (1.0 mmol) of 2-chloro-6-(3-chloro-phenyl-amino)-9-ethyl-9H-purine [described in Stage 1.2] and 1.95 g of imidazole in a glass pressure reactor after 16 h at 140° C. and purification by means of digestion in diisopropyl ether; m.p. 193.2° C.; FAB-MS: $(M+H)^+=339$; HPLC: $t_{ret}$ $(grad_{20/2})$ =11.50 minutes.

EXAMPLE 52

Analogously to Example 1, 2-[3-amino-pyrrolidin-1-yl]-6-(3-chloro-phenyl-amino)-9-ethyl-9H-purine is obtained from 462 mg (1.5 mmol) of 2-chloro-6-(3-chloro-phenyl-amino)-9-ethyl-9H-purine [described in Stage 1.2], 262 mg (1.65 mmol) of 3-amino-pyrrolidine dihydrochloride and 0.417 ml (2.1 mmol) of 1,8-diazabicyclo[5.4.0]undec-7-ene (1.5–5)(=DBU) in 3.0 ml of dimethyl sulfoxide in a glass pressure reactor after 24 h at 140° C. and purification by means of column chromatography (MPLC); FAB-MS: $(M+H)^+=358$; HPLC: $t_{ret}$ $(grad_{20/2})$=9.10 minutes.

EXAMPLE 53

Analogously to Example 1, 2-[carbamoyl-methyl-amino]-6-(3-chloro-phenyl-amino)-9-ethyl-9H-purine is obtained from 462 mg (1.5 mmol) of 2-chloro-6-(3-chloro-phenyl-amino)-9-ethyl-9H-purine [described in Stage 1.2], 121.6 mg (1.1 mmol of glycinamide hydrochloride and 0.314 ml (2.1 mmol) of 1,8-diazabicyclo[5.4.0]undec-7-ene(1.5–5) (=DBU) in 3.0 ml of dimethyl sulfoxide in a glass pressure reactor after 18 h at 150° C. and purification by means of column chromatography; m.p.>220° C.; FAB-MS: $(M+H)^+$ =346; HPLC: $t_{ret}$ $(grad_{20/2})$=8.99 minutes.

EXAMPLE 54

Analogously to Example 1, 6-(3-chloro-phenyl-amino)-2-(1,4-dioxa-8-azaspiro[4.5]dec-8-yl)-9-ethyl-9H-purine is obtained from 308 mg (1.0 mmol) of 2-chloro-6-(3-chlorophenyl-amino)-9-ethyl-9H-purine [described in Stage 1.2] and 3.67 ml (28.6 mmol) of 1,4-dioxa-8-azaspiro[4.5]decane after 22 h at RT, followed by purification by means of digestion several times in diethyl ether; as pale beige crystals; m.p. 159–161° C.; FAB-MS: $(M+H)^+=415$; HPLC: $t_{ret}$ $(grad_{20/2})$=12.23 minutes.

EXAMPLE 55

Analogously to Example 1, 2-[3-amino-2-hydroxy-prop-1-yl-amino]-6-(3-chloro-phenyl-amino)-9-ethyl-9H-purine is obtained from 308 mg (1.0 mmol) of 2-chloro-6-(3-chloro-phenyl-amino)-9-ethyl-9H-purine [described in Stage 1.2] and 2.58 g of 1,3-diamino-2-propanol after 6 h at 150° C. and purification by means of digestion in diisopropyl ether; FAB-MS: $(M+H)^+=362$; HPLC: $t_{ret}$ $(grad_{20/2})$ =7.68 minutes.

EXAMPLE 56

Analogously to Example 1, 2-[4-amino-phenyl-amino]-6-(3-chloro-phenyl-amino)-9-ethyl-9H-purine is obtained from 308 mg (1.0 mmol) of 2-chloro-6-(3-chloro-phenyl-amino)-9-ethyl-9H-purine [described in Stage 1.2], 324 mg (3 mmol) of 1,4-phenylendiamine in 10 ml of n-butanol in a glass pressure reactor after 48 h at 150° C. and purification by means of column chromatography; FAB-MS: $(M+H)^+$ =380; HPLC: $t_{ret}$ $(grad_{20/2})$=8.87 minutes.

EXAMPLE 57

Analogously to Example 1, 2-[2-amino-benzyl-amino]-6-(3-chloro-phenyl-amino)-9-ethyl-9H-purine is obtained from 308 mg (1.0 mmol) of 2-chloro-6-(3-chloro-phenyl-amino)-9-ethyl-9H-purine [described in Stage 1.2] and 3.5 g of 2-amino-benzylamine after 5 h at 140° C. and purification by means of column chromatography (MPLC) and crystallization from diethyl ether/hexane; m.p. 166,5° C.; FAB-MS: $(M+H)^+=393$; HPLC: $t_{ret}$ $(grad_{20/2})$=11.13 minutes.

EXAMPLE 58

Analogously to Example 1, 2-(2-acetylamino-ethylamino)-6-(3-chloro-phenyl-amino)-9-ethyl-9H-purine is obtained from 308 mg (1.0 mmol) of 2-chloro-6-(3-chlorophenyl-amino)-9-ethyl-9H-purine [described in Stage 1.2] and 2.78 ml of 2-acetylamino-1-amino-ethane after 30 h at 60° C. and purification by means of column chromatography; FAB-MS: $(M+H)^+=374$; HPLC: $t_{ret}$ $(grad_{20/2})$=10.15 minutes.

EXAMPLE 59

Analogously to Example 1, 308 mg (1.0 mmol) of 2-chloro-6-(3-chloro-phenyl-amino)-9-ethyl-9H-purine [described in Stage 1.2] and 324 mg (3 mmol) of 1,2-phenylendiamine are reacted in 10 ml of n-butanol in a glass pressure reactor for 19 h at 140° C., followed by addition of 486 mg (4.5 mmol) of 1,2-phenylenediamine and further reaction at 135° C. for 17 h. After purification by means of column chromatography, 2-[2-amino-phenyl-amino]-6-(3- chloro-phenyl-amino)-9-ethyl-9H-purine is obtained; FAB-MS: (M+H)$^+$=380; HPLC: t$_{ret}$ (grad$_{20/2}$)=11.36 minutes.

EXAMPLE 60

Analogously to Example 1, 2-(2-[2-amino-ethyl-amino]-ethyl-amino)-6-(3-chloro-phenyl-amino)-9-ethyl-9H-purine is obtained from 308 mg (1.0 mmol) of 2-chloro-6-(3-chloro-phenyl-amino)-9-ethyl-9H-purine [described in Stage 1.2] and 5.43 ml of diethylenetriamine after 14 h at 75° C. and purification by means of column chromatography; FAB-MS: (M+H)$^+$=375, HPLC: t$_{ret}$ (grad$_{20/2}$)=7.40 minutes.

EXAMPLE 61

Analogously to Example 1, 2-([3-aminomethyl]-benzyl-amino)-6-(3-chloro-phenyl-amino)-9-ethyl-9H-purine is obtained from 308 mg (1.0 mmol) of 2-chloro-6-(3-chloro-phenyl-amino)-9-ethyl-9H-purine [described in Stage 1.2) and 6.48 ml of 1,3-di-(aminomethyl)benzene after 24 at 75° C. and purification by means of column chromatography; FAB-MS: (M+H)$^+$=408; HPLC: t$_{ret}$(grad$_{20/2}$)=9.70 minutes.

EXAMPLE 62

Analogously to Example 1, 6-(3-chloro-phenyl-amino)-2-[N-cyclohexyl-N-(2-hydroxy-ethyl)-amino]-9-ethyl-9H-purine is obtained from 308 mg (1.0 mmol) of 2-chloro-6-(3-chloro-phenyl-amino)-9-ethyl-9H-purine [described in Stage 1.2] and 358 mg (2.5 mmol) of 2-cyclohexylamino-ethanol in 2 ml of DMSO after 22 h at 100° C., 20 h at 135° C. and 3 h at 150° C., followed by purification by means of digestion several times in diethyl ether and column chromatography; as a yellowish solid; m.p. 125–128° C.; FAB-MS: (M+H)$^+$=415; HPLC: t$_{ret}$ (grad$_{20/3}$)=12.93 minutes.

EXAMPLE 63

150 mg (3.95 mmol) of LiAlH$_4$ are added to a suspension of 400 mg (0.79 mmol) of 6-(3-chloro-phenyl-amino)-9-ethyl-2-[2-(4-methoxy-phenyl-amino-carbonyl)-hexahydro-pyridazino]-9H-purine (cf. Example 77) in 7 ml of abs. diethyl ether and the mixture is stirred in a glass pressure reactor under argon at 80° C. for 15 h. After cooling, 0.66 ml of water and 0.16 ml of aqueous 15% NaOH solution are added dropwise and the reaction mixture is then concentrated under reduced pressure. The resulting product mixture is purified by means of column chromatography and digestion in diisopropyl ether. 6-(3-Chloro-phenyl-amino)-9-ethyl-2-[2-{1-hydroxy-1-(4-methoxy-phenyl-amino)-methyl}-hexahydropyrdazino]-9/purine is obtained; m.p. 163–166° C.; FAB-MS: (M+H)$^+$=509, HPLC: t$_{ret}$ (grad$_{20/2}$)=9.89 minutes.

EXAMPLE 64

Analogously to Example 1, 2-[(S)-2-carbamoyl-pyrrolidin-1-yl]-6-(3-chloro-phenyl-amino)-9-ethyl-9H-purine is obtained from 1.232 g (4.0 mmol) of 2-chloro-6-(3-chloro-phenyl-amino)-9-ethyl-9H-purine (described in Stage 1.2], 913 mg (4.0 mmol of L-prolinamide [i.e. (S)-(–)-prolinamide] in 5 ml of dimethyl sulfoxide after 5 days at 80° C. and purification by means of digestion in diisopropyl ether; m.p.>240° C.; FAB-MS: (M+H)$^+$=386; HPLC: t$_{ret}$ (grad$_{20/2}$)=11.70 minutes; [α]$_D^{20}$=–8.0° [DMSO, c=0.5].

EXAMPLE 65

Analogously to Example 1, 6-(3-chloro-phenyl-amino)-9-ethyl-2-(trans-4-hydroxy-cyclohexyl-amino)-9H-purine is obtained from 616 mg (2.00 mmol) of 2-chloro-6-(3-chloro-phenyl-amino)-9-ethyl-9H-purine [described in Stage 1.2], 607 mg (4.0 mmol) of trans-4-amino-cyclohexanol hydrochloride and 1.315 ml (8.8 mmol) of 1,8-diazabicyclo-[5.4.0]undec-7-ene(1.5–5)(=DBU) after 3 days at 100° C., 3 days at 50° C. and purification by means of column chromatography; m.p. 116.5° C.; FAB-MS: (M+H)$^+$=387; HPLC: t$_{ret}$ (grad$_{20/2}$)=11.64 minutes.

EXAMPLE 66

100 mg (0.25 mmol) of 6-(3-chloro-phenyl-amino)-9-ethyl-2-(3-[N-formyl]-amino-piperidin-1-yl)-9H-purine (cf. Example 48) are suspended in a total of 9.3 ml of methanolic hydrochloric acid (0.5 molar) and the suspension is stirred at room temperature for 1 day and then at 60° C. for 4 days. The reaction mixture is poured onto 50 ml of a saturated sodium bicarbonate solution and extracted three times with ethyl acetate. The combined organic extracts are washed with water and brine and dried (sodium sulfate) and the solvent is removed on a rotary evaporator. After digestion in a little diethyl ether, 2-(3-amino-piperidin-1-yl)-6-(3-chloro-phenyl-amino)-9-ethyl-9H-purine is obtained; m.p. 165° C.; FAB-MS: (M+H)$^+$=372; HPLC: t$_{ret}$ (grad$_{20/2}$)=10.30 minutes.

EXAMPLE 67

A suspension of 230 mg (6.07 mmol) of LiAlH$_4$ in 5 ml of abs. THF is added dropwise to a suspension of 600 mg (1.6 mmol) of 6-(3-chloro-phenyl-amino)-9-ethyl-[(S)-2-carbamoyl-pyrrolidin-1-yl]-9H-purine (cf. Example 64) in 15 ml of abs. THF, and the mixture is stirred at 80° C. for 24 h. Thereafter, 10 ml of ice/water are cautiously added dropwise and the reaction mixture is poured onto 50 ml of ice/water. The mixture is extracted three times with ethyl acetate (100 ml each time). The combined organic extracts are washed with aqueous sodium bicarbonate solution, water and saturated sodium chloride solution and dried over sodium sulfate. After filtration, the filtrate is concentrated under reduced pressure. The resulting crude product (oil) is purified by means of column chromatography (silica gel), digestion in diethyl ether/hexane and RP-MPLC (medium pressure chromatography, Lichroprep® RP-18 (irregular silica gel support material, Merck, Darmstadt, Germany)). 2-[(S)-2-Aminomethyl-pyrrolidin-1-yl]-6-(3-chloro-phenyl-amino)-9-ethyl-9H-purine is obtained as an oil; FAB-MS: (M+H)$^+$=372, HPLC: t$_{ret}$ (grad$_{20/2}$)=11.25 minutes; [α]$_D^{20}$=–56.1° [DMSO, c=0.51].

EXAMPLE 68

Analogously to Example 1, 6-(3-chloro-phenylamino)-9-ethyl-[4-hydroxymethyl-(imidazolyl)]-9H-purine is obtained from 308 mg (1.0 mmol) of 2-chloro-6-(3-chloro-phenyl-amino)-9-ethyl-9H-purine [described in Stage 1.2], 148 mg (1.1 mmol) of 4-(hydroxymethyl)-imidazole hydrochloride and 0.314 ml (2.1 mmol) of DBU in 2.5 ml of dimethyl sulfoxide in a glass pressure reactor after 48 h at 140° C. followed by purification by means of MPLC (silica gel); FAB-MS: (M+H)$^+$=370; HPLC: t$_{ret}$ (grad$_{20/2}$)=10.96 minutes.

EXAMPLE 69

Analogously to Example 1, 6-(3-chloro-phenyl-amino)-2-(trans-2-hydroxy-cyclohexylamino)-9-ethyl-9H-purine is obtained from 308 mg (1.0 mmol) of 2-chloro-6-(3-chloro-phenyl-amino)-9-ethyl-9H-purine [described in Stage 1.2], 166.8 mg (1.1 mmol) of trans-2-amino-cyclohexanol hydrochloride and 0.314 ml (2.1 mmol) of DBU in 2 ml of dimethylsulfoxide after 24 h at 130° C. and purification by means of MPLC (silica gel); FAB-MS: $(M+H)^+$=387; HPLC: $t_{ret}$ ($grad_{20/2}$)=13.38 minutes.

EXAMPLE 70

Analogously to Example 1, 6-(3-chloro-phenyl-amino)-9-ethyl-2-(1-hydroxymethyl-cyclopent-1-yl-amino)-9H-purine is obtained from 308 mg (1.0 mmol) of 2-chloro-6-(3-chloro-phenyl-amino)-9-ethyl-9H-purine [described in Stage 1.2] and 1.47 g (12.8 mmol) of 1-amino-1-hydroxymethyl-cyclopentane in 1 ml of dimethyl sulfoxide in a glass pressure reactor after 24 h at 130° C. and purification by means of MPLC (silica gel); FAB-MS: $(M+H)^+$=387; HPLC: $t_{ret}$ ($grad_{20/2}$)=13.43 minutes.

EXAMPLE 71

Analogously to Example 1, 6-(3-chloro-phenyl-amino)-2-(2-cyano-ethylamino)-9-ethyl-9H-purine trifluoracetate is obtained as an oil from 308 mg (1.0 mmol) of 2-chloro-6-(3-chloro-phenyl-amino)-9-ethyl-9H-purine [described in Stage 1.2], 282 mg (1.1 mmol) of 3-amino-propionitrile fumarate and 0.314 ml (2.1 mmol) of DBU in 2.5 ml of dimethyl sulfoxide in a glass pressure reactor after 30 h at 150° C., followed by purification by means of column chromatography (silica gel), digestion in diisopropyl ether and RP-MPLC column chromatography (medium pressure chromatography, Lichroprep RP-18); FAB-MS: $(M+H)^+$=342; HPLC: $t_{ret}$ ($grad_{20/2}$)=12.35 minutes.

EXAMPLE 72

Analogously to Example 1, 6-(3-chloro-phenyl-amino)-9-ethyl-2-(4-hydroxy-piperidino)-9H-purine is obtained from 308 mg (1.0 mmol) of 2-chloro-6-(3-chloro-phenyl-amino)-9-ethyl-9H-purine [described in Stage 1.2] and 2.89 g (28.6 mmol) of 4-hydroxypiperidine in a glass pressure reactor after 17 h at 130° C., followed by purification by means of digestion in diisopropyl ether; m.p. 198.7° C.; FAB-MS: $(M+H)^+$=373; HPLC: $t_{ret}$ ($grad_{20/2}$)=12.63 minutes.

EXAMPLE 73

Analogously to Example 1, 6-(3-chloro-phenyl-amino)-9-ethyl-2-(hexahydropyridazino)-9H-purine is obtained from 308 mg (1.0 mmol) of 2-chloro-6-(3-chloro-phenyl-amino)-9-ethyl-9H-purine [described in Stage 1.2] and 431 mg (4.64 mmol) of hexahydropyridazine in a glass pressure reactor after 20 h at 65° C., followed by purification by means of digestion in diisopropy ether; m.p. 126° C.; FAB-MS: $(M+H)^+$=358; HPLC: $t_{ret}$ ($grad_{20/2}$)=12.03 minutes.

EXAMPLE 74

Analogously to Example 1, 6-(3-chloro-phenylamino)-2-[(2,6-dimethyl)-piperazino]-9-ethyl-9H-purine is obtained as a colourless powder from 308 mg (1.0 mmol) of 2-chloro-6-(3-chloro-phenyl-amino)-9-ethyl-9H-purine [described in Stage 1.2] and 3.26 g (28.61 mmol) of 2,6-dimethyl-piperazine in a glass pressure reactor after 16 h at 140° C., followed by purification by means of digestion in diisopropyl ether; m.p. 183° C.; FAB-MS: $(M+H)^+$=386; HPLC: $t_{ret}$ ($grad_{20/2}$)=10.49 minutes.

EXAMPLE 75

Analogously to Example 1, 2-[4-amino-piperazin-1-yl]-6-(3-chloro-phenyl-amino)-9-ethyl-9H-purine is obtained from 308 mg (1.0 mmol) of 2-chloro-6-(3-chloro-phenyl-amino)-9-ethyl-9H-purine [described in Stage 1.2], 191 mg (1.1 mmol) of piperazin-1-yl-amine and 0.314 ml (2.1 mmol) of DBU in 1.0 ml of dimethyl sulfoxide in a glass pressure reactor after 20 h at 100° C., followed by purification by means of column chromatography, digestion in diisopropyl ether and MPLC (silica gel); FAB-MS: $(M+H)^+$=373; HPLC: $t_{ret}$ ($grad_{20/2}$)=9.65 minutes.

EXAMPLE 76

Analogously to Example 1, 6-(3-chloro-phenyl-amino)-9-ethyl-2-(cis-2-hydroxy-cyclohex-1-yl-amino)-9H-purine is obtained as a solid oil from 308 mg (1.0 mmol) of 2-chloro-6-(3-chloro-phenyl-amino)-9-ethyl-9H-purine [described in Stage 1.2], 177 mg (1.1 mmol) of cis-2-amino-cyclohexanol hydrochloride and 0.314 ml (2.1 mmol) of DBU in 2.0 ml of dimethyl sulfoxide in a glass pressure reactor after 17 h at 100° C. and then 5 h at 150° C., followed by purification by means of column chromatography; FAB-MS: $(M+H)^+$=387; HPLC: $t_{ret}$ ($grad_{20/2}$)=13.86 minutes.

EXAMPLE 77

0.126 ml of p-tolyl isocyanate is added dropwise in portions to a solution of 358 mg (1 mmol) of 6-(3-chloro-phenyl-amino)-9-ethyl-2-(hexahydropyridazino)-9H-purine (cf. Example 73) in 2 ml of methylene chloride while cooling with ice/water. The white suspension formed is stirred at RT for 20 h and dissolved in 100 ml of methylene chloride and the solution is extracted with saturated aqueous $NaHCO_3$ solution, water and brine and dried over sodium sulfate. After filtration, the filtrate is concentrated under reduced pressure. The resulting crude product is purified by means of digestion in diethyl ether. 6-(3-Chloro-phenyl-amino)-9-ethyl-2-[2-(p-tolyl-amino-carbonyl)-hexahydro-pyridazino]-9H-purine is obtained as colourless crystals; m.p. 224° C.; FAB-MS: $(M+H)^+$=491; HPLC: $t_{ret}$ ($grad_{20/2}$)=17.67 minutes.

EXAMPLE 78

73.1 mg of methyl isothiocyanate are added in portions to a solution of 358 mg (1 mmol) of 6-(3-chloro-phenyl-amino)-9-ethyl-2-(hexahydropyridazino)-9H-purine (cf. Example 73) in 2 ml of methylene chloride, while cooling with ice/water. The white suspension formed is stirred at RT for 20 h and dissolved in 100 ml of methylene chloride and the solution is extracted with saturated aqueous $NaHCO_3$ solution, water and brine and dried over sodium sulfate. After filtration, the filtrate is concentrated under reduced pressure. The resulting crude product is purified by means of digestion in diethyl ether. 6-(3-Chloro-phenyl-amino)-9-ethyl-2-[2-(N-methyl-thiocarbamoyl)-hexahydropyridazino]-9H-purine is obtained as colourless crystals; m.p. 119° C.; FAB-MS: (M+H)$^+$=431; HPLC: t$_{ret}$ (grad$_{20/2}$) =16.21 minutes.

EXAMPLE 79

0.074 ml of tert-butyl isocyanate is added dropwise in portions to a solution of 230 mg (0.64 mmol) of 6-(3-chloro-phenyl-amino)-9-ethyl-2-(hexahydropyridazino)-9H-purine (cf. Example 73) in 1 ml of methylene chloride, while cooling with ice/water, and the mixture is stirred at RT for 17 h. A further 0.034 ml of tert-butyl isocyanate is added and the mixture is stirred at RT for 4 h. The reaction mixture is then dissolved in 100 ml of methylene chloride and the solution is extracted with sat. aqueous sodium bicarbonate solution, water and brine and dried over sodium sulfate. After filtration, the filtrate is concentrated under reduced pressure. The resulting crude product is purified by means of digestion in a little hexane/methylene chloride. 2-[2-(tert-Butyl-amino-carbonyl)-hexahydro-pyridazino]-6-(3-chloro-phenyl-amino)-9-ethyl-9H-purine is obtained; FAB-MS: (M+H)$^+$=457; HPLC: t$_{ret}$ (grad$_{20/2}$)=17.96 minutes.

EXAMPLE 80

0.082 ml of cyclohexyl isocyanate is added dropwise in portions to a solution of 230 mg (0.64 mmol) of 6-(3-chloro-phenyl-amino)-2-(hexahydropyridazino)-9-ethyl-9H-purine (cf. Example 73) in 1 ml of methylene chloride, while cooling with ice/water, and the mixture is stirred at RT for 17 h. A further 0.027 ml of cyclohexyl isocyanate is added and the mixture is stirred at RT for 2 h. The reaction mixture is then dissolved in 100 ml of methylene chloride and the solution is extracted with sat. aqueous sodium bicarbonate solution, water and brine and dried over sodium sulfate. After filtration, the filtrate is concentrated under reduced pressure. The resulting crude product is purified by means of digestion in a little hexane/methylene chloride. 6-(3-Chloro-phenyl-amino)-2-[2-(cyclohexyl-amino-carbonyl)-hexahydropyridazino]-9-ethyl-9H-purine is obtained; FAB-MS: (M+H)$^+$=483; HPLC: t$_{ret}$ (grad$_{20/2}$)=18.82 minutes.

EXAMPLE 81

Analogously to Example 1, 6-(3-chloro-phenyl-amino)-9-ethyl-2-(3-hydroxy-2-methyl-prop-2-yl-amino)-9H-purine is obtained from 308 mg (1.0 mmol) of 2-chloro-6-(3-chloro-phenyl-amino)-9-ethyl-9H-purine [described in Stage 1.2] and 2.74 ml (28.6 mmol) of 2-amino-2-methyl-1-propanol in a glass pressure reactor under argon after 17 h at 100° C. and then 6 h at 150° C., followed by purification by means of digestion several times; FAB-MS: (M+H)$^+$ =361; HPLC: t$_{ret}$ (grad$_{20/2}$)=12.23 minutes.

EXAMPLE 82

Analogously to Example 1, 6-(3-chloro-phenyl-amino)-9-ethyl-2-piperidino-9H-purine is obtained from 308 mg (1.0 mmol) of 2-chloro-6-(3-chlor-phenyl-amino)-9-ethyl-9H-purine [described in Stage 1.2] and 2.83 ml of piperidine in a glass pressure reactor under argon after 17 h at 100° C., followed by purification by means of digestion in a little hexane/methylene chloride; m.p. 126° C.; FAB-MS: (M+H)$^+$=357; HPLC: t$_{ret}$ (grad$_{20/2}$)=18.23 minutes.

EXAMPLE 83

Analogously to Example 1, 6-(3-chloro-phenyl-amino)-9-ethyl-2-[(S)-1-hydroxy-but-2-yl-amino]-9H-purine is obtained as colourless crystals from 308 mg (1.0 mmol) of 2-chloro-6-(3-chloro-phenyl-amino)-9-ethyl-9H-purine [described in Stage 1.2] and 2.7 ml (28.6 mmol) of S-(+)-2-amino-1-butanol in a glass pressure reactor under argon after 18 h at 150° C., followed by purification by means of digestion in diethyl ether; m.p. 203° C.; FAB-MS: (M+H)$^+$ =361; HPLC: t$_{ret}$ (grad$_{20/2}$)=12.20 minutes, [α]$_D^{20}$=−23.0° [methanol, c=1].

EXAMPLE 84

Analogously to Example 1, 6-(3-chloro-phenyl-amino)-9-ethyl-2-[(R)-1-hydroxy-but-2-yl-amino)-9H-purine is obtained as colourless crystals from 308 mg (1.0 mmol) of 2-chloro-6-(3-chloro-phenyl-amino)-9-ethyl-9H-purine [described in Stage 1.2] and 2.7 ml (28.6 mmol) of R-(+)-2-amino-1-butanol (R:S>90:10) in a glass pressure reactor under argon after 18 h at 150° C., followed by purification by means of digestion in diethyl ether; m.p. 200° C.; FAB-MS: (M+H)$^+$=361; HPLC: t$_{ret}$ (grad$_{20/2}$)=12.22 minutes, [α]$_D^{20}$=+19.2° [methanol, c=1].

EXAMPLE 85

Analogously to Example 1, 6-(3-chloro-phenyl-amino)-2-cyclohexylamino-9-ethyl-9H-purine is obtained from 308 mg (1.0 mmol) of 2-chloro-6-(3-chloro-phenyl-amino)-9-ethyl-9H-purine [described in Stage 1.2] and 3.27 ml (28.6 mmol) of cyclohexylamine after 20 h at 100° C., followed by purification by means of digestion in diisopropyl ether; as colourless crystals; m.p. 143° C.; FAB-MS: (M+H)$^+$=371; HPLC: t$_{ret}$ (grad$_{20/3}$)=12.94 minutes.

EXAMPLE 86

Analogously to Example 1, 6-(3-chloro-phenyl-amino)-9-ethyl-2-(1,3-dihydroxy-prop-2-yl-amino)-9H-purine is obtained from 308 mg (1.0 mmol) of 2-chloro-6-(3-chloro-phenyl-amino)-9-ethyl-9H-purine [described in Stage 1.2] and 2.6 g (28.6 mmol) of 2-amino-1,3-propanediol after 23 h at 100° C., followed by purification by means of digestion several times in diethyl ether; FAB-MS: (M+H)$^+$=363; HPLC: t$_{ret}$ (grad$_{20/3}$)=7.06 minutes.

EXAMPLE 87

Analogously to Example 1, 6-(3-chloro-phenyl-amino)-9-ethyl-2-(4-methyl-cyclohexyl-amino)-9H-purine is obtained from 308 mg (1.0 mmol) of 2-chloro-6-(3-chloro-phenyl-amino)-9-ethyl-9H-purine [described in Stage 1.2] and 3.8 ml (28.6 mmol) of 4-methyl-cyclohexyl-amine after 17 h at 95° C., followed by purification by means of MPLC column chromatography; FAB-MS: (M+H)$^+$=385; HPLC: t$_{ret}$ (grad$_{20/3}$)=13.85 minutes.

EXAMPLE 88

Analogously to Example 1, 6-(3-chloro-phenyl-amino)-9-ethyl-2-[(R)-2-hydroxy-propylamino]-9H-purine is obtained as pale reddish crystals from 308 mg (1.0 mmol) of 2-chloro-6-(3-chloro-phenyl-amino)-9-ethyl-9H-purine [described in Stage 1.2] and 2.25 g (28.6 mmol) of R-(−)-1-amino-2-propanol after 18 h at 100° C., followed by purification by means of digestion in diethyl ether; m.p. 161° C.; FAB-MS: $(M+H)^+$=347; HPLC: $t_{ret}$ (grad$_{20/3}$)=8.39 minutes; $[\alpha]_D^{20}$=−20.8°[methanol, c=1].

EXAMPLE 89

Analogously to Example 1, 6-(3-chloro-phenyl-amino)-9-ethyl-2-[(S)-2-hydroxy-propylamino]-9H-purine is obtained as pale beige crystals from 308 mg (1.0 mmol) of 2-chloro-6(3-chloro-phenyl-amino)-9-ethyl-9H-purine [described in Stage 1.2] and 2.25 g (28.6 mmol) of S-(+)-1-amino-2-propanol after 18 h at 100° C., followed by purification by means of digestion in diethyl ether; m.p. 161° C.; FAB-MS: $(M+H)^+$=347; HPLC: $t_{ret}$ (grad$_{20/3}$)=8.40 minutes; $[\alpha]_D^{20}$=+21.7° [methanol, c=1].

EXAMPLE 90

0.2 g (0.62 mmol) of 2-chloro-9-ethyl-6-(3-fluoro-phenyl-amino)-9H-purine is stirred in 2.5 ml of ethylenediamine at 75° C. for 3 h, and the mixture is allowed to cool and is diluted with ethyl acetate. The organic phase is washed with water, separated off and dried over sodium sulfate. After removal of the solvent, the residue is dissolved in dioxane, and treated with 4 N HCl in dioxane. 2-(2-Amino-ethyl-amino)-9-ethyl-6-(3-fluor-phenyl-amino)-9H-purine hydrochloride is obtained as a crystalline precipitate by this procedure. This precipitate is filtered off and dried; m.p.>250° C.; FAB-MS: $(M+H)^+$=315; $R_f$=0.6 (ethyl acetate:isopropanol:water:22% aqueous ammonium hydroxide solution=40:60:15:18).

The starting material is obtained as follows:

Stage 90.1: 2 g (10.58 mmol) of 2,6-dichloro-purine and 5.9 g (52.9 mmol) of 3-fluoro-aniline (Fluka, Buchs, Switzerland) are stirred in 60 ml of n-butanol and 3 ml of DMF at 80° C. for 5 h. The cooled reaction mixture is treated with isopropanol and the crystal mass which has precipitated out is filtered off and dried. 2-Chloro-6-(3-fluoro-phenyl-amino)-purine is obtained; m.p.>250° C.; FAB-MS: $(M+H)^+$=264; $R_f$=0.3 (CH$_2$Cl$_2$:methanol 9:1).

Stage 90.2: 1 g (3.47 mmol) of 2-chloro-6-(3-fluoro-phenyl-amino)-purine, 1.8 g (5.5 mmol) of caesium carbonate and 2.3 ml (27.8 mmol) of iodoethane are stirred in 14 ml of a dioxane/water mixture (4:3) and 12 ml of DMF at RT for 16 h. Thereafter, the reaction mixture is diluted with ethyl acetate and the organic phase is washed with water and dried over sodium sulfate. After removal of the solvent, the residue is chromatographed over silica gel (mobile phase: ethyl acetate/hexane=4:1) and 2-chloro-9-ethyl-6-(3-fluoro-phenyl-amino)-9H-purine is isolated; m.p. 136° C.; FAB-MS: $(M+H)^+$=292; $R_f$=0.7 (CH$_2$Cl$_2$:methanol=9:1).

EXAMPLE 91

0.2 g (0.63 mmol) of 2-chloro-9-isopropyl-6-(3-fluoro-phenyl-amino)-9H-purine is stirred in 2.5 ml of ethylenediamine at 75° C. for 5 h. The mixture is allowed to cool and is diluted with ethyl acetate. The organic phase is washed with water and dried over sodium sulfate. After removal of the solvent, the residue is dissolved in dioxane and treated with 4 N HCl in dioxane. 2-(2-Amino-ethyl-amino)-6-(3-fluoro-phenyl-amino)-9-isopropyl-9H-purine precipitates out as a crystalline precipitate by this procedure; m.p.>250° C.; FAB-MS: $(M+H)^+$=329; $R_f$=0.1 (CH$_2$Cl$_2$:methanol=9:1).

The starting material is obtained as follows:

Stage 91.1: Analogously to Stage 90.2, 2-chloro-9-isopropyl-6-(3-fluoro-phenyl-amino)-9H-purine is obtained from 1 g (3.47 mmol) of 2-chloro-6-(3-fluoro-phenyl-amino)-purine (prepared according to Stage 90.1), 2.3 g of caesium carbonate (6.95 mmol) and 2.1 ml (20.8 mmol) of isopropyl iodide in 48 ml of a mixture comprising dioxane/water/DMF in a ratio of 2:3:5, after stirring at 80° C. for 6 h; m.p. 130° C.; FAB-MS: $(M+H)^+$306; $R_f$=0.85 (CH$_2$Cl$_2$:methanol=9:1).

EXAMPLE 92

0.2 g (0.62 mmol) of 2-chloro-9-ethyl-6-(3-fluoro-phenyl-amino)-9H-purine (prepared according to Stage 90.2) is stirred in 1 ml of ethanolamine at 150° C. for 3 h, and the mixture is allowed to cool and is diluted with ethyl acetate. The organic phase is washed with water, separated off and dried over sodium sulfate. On concentration, 2-(2-hydroxy-ethyl-amino)-6-(3-fluoro-phenyl-amino)-9-ethyl-9H-purine is obtained as a crystalline precipitate. This precipitate is filtered off and dried; m.p. 184° C.; FAB-MS: $(M+H)^+$=317; $R_f$=0.5 (CH$_2$Cl$_2$:methanol=9:1).

EXAMPLE 93

0.2 g (0.63 mmol) of 2-chloro-9-isopropyl-6-(3-fluoro-phenyl-amino)-9H-purine (prepared according to Stage 91.1) is stirred in 1 ml of ethanolamine at 150° C. for 5 h, and the mixture is then allowed to cool and is diluted with ethyl acetate. The organic phase is washed with water and dried over sodium sulfate. On concentration of the solvent, 6-(3-fluoro-phenyl-amino)-2-(2-hydroxy-ethyl-amino)-9-isopropyl-9H-purine is obtained as a crystalline mass. This is filtered off and dried; m.p. 142° C.; FAB-MS: $(M+H)^+$=330; $R_f$=0.6 (CH$_2$Cl$_2$:methanol 9:1).

EXAMPLE 94

0.2 g (0.6 mmol) of 2-chloro-9-ethyl-6-(3-cyano-phenyl-amino)-9H-purine is stirred in 2.5 ml of ethylenediamine at 75° C. for 3.5 h, and the mixture is allowed to cool and is diluted with ethyl acetate. The organic phase is washed with water, separated off and dried over sodium sulfate. After removal of the solvent, the residue is dissolved in 3 ml of dioxane and treated with 4 N HCl in dioxane. 2-(2-Amino-ethyl-amino)-6-(3-cyano-phenyl-amino)-9-ethyl-9H-purine hydrochloride is obtained as a crystalline precipitate. This is filtered off and dried; m.p. 200° C.; FAB-MS: $(M+H)^+$=323; $R_f$=0.5 (ethyl acetate:i-propanol:water: 22% aqueous ammonium hydroxide solution=40:60:15:10).

The starting material is obtained as follows:

Stage 94.1: 2 g (10.6 mmol) of 2,6-dichloropurine and 6.3 g (52.9 mmol) of 3-amino-benzonitrile are stirred in 63 ml of a DMF:n-butanol mixture (1:30) at 80° C. for 18 h. The cooled reaction mixture is treated with ethyl acetate, 2-chloro-6-(3-cyano-phenyl-amino)-purine precipitating. The crystal mass is filtered off and dried; m.p.>250° C.; FAB-MS: $(M+H)^+$=271; $R_f$=0.45 (CH$_2$Cl$_2$:methanol=9:1).

Stage 94.2: 1.5 g (3.95 mmol) of 2-chloro-6-(3-cyano-phenyl-amino)-purine, 2.1 g (6.3 mmol) of caesium carbonate and 2.6 ml (31.6 mmol) of iodoethane are stirred in 66 ml of a mixture comprising dioxane:water:DMF in a ratio of 1:2:3 at RT for 19 h. Thereafter, the reaction mixture is diluted with ethyl acetate and the organic phase is washed with water. After drying over sodium sulfate, the residue is chromatographed over silica gel (mobile phase: ethyl acetate:hexane=4:1). After removal of the solvent, 2-chloro-9-ethyl-6-(3-cyano-phenyl-amino)-9H-purine is obtained as a crystalline precipitate. This precipitate is filtered off and dried; m.p. 189° C.; FAB-MS: (M+H)$^+$=299; $R_f$=0.9 (CH$_2$Cl$_2$:methanol 9:1).

EXAMPLE 95

0.19 g (0.55 mmol) of 2-chloro-9-ethyl-6-(3-trifluoromethyl-phenyl-amino)-9H-purine is stirred in 0.6 ml of ethylenediamine at 140° C. for 2 h, and the mixture is then allowed to cool and is diluted with ethyl acetate. The organic phase is washed with water, separated off and dried over sodium sulfate. After removal of the solvent, the residue is dissolved in isopropanol. After addition of 4 N HCl in dioxane, 2-(2-amino-ethyl-amino)-9-ethyl-6-(3-trifluoromethyl-phenyl-amino)-9H-purine precipitates out as crystals and is filtered off and dried; m.p.>250° C.; FAB-MS: (M+H)$^+$=366; $R_f$=0.4 (CH$_2$Cl$_2$:methanol:water=70:30:5).

The starting material is obtained as follows:

Stage 95.1: 1.9 g (10 mmol) of 2,6-dichloro-purine are stirred in 60 ml of butanol and 3 ml of DMF with 8.05 g (50 mmol) of 3-amino-benzotrifluoride at 60° C. for 3 h. On cooling, 2-chloro-6-(3-trifluoromethyl-phenyl-amino)-purine is obtained as a crystalline mass. This is filtered off and dried in vacuo; m.p. 248° C.; FAB-MS: (M+H)$^+$=314; $R_f$=0.45 (CH$_2$Cl$_2$:methanol=95:5).

Stage 95.2: 1 g (3.2 mmol) of 2-chloro-6-(3-trifluoromethyl-phenyl-amino)-purine, 1.7 g (5.1 mmol) of caesium carbonate and 2.1 ml (25.6 mmol) of ethyl iodide are stirred in 7 ml of a mixture comprising dioxane, water and DMF in a ratio of 8:2:2 at RT for 18 h. Thereafter, the reaction mixture is diluted with ethyl acetate and the organic phase is washed with water. After drying over sodium sulfate and removal of the solvent, 2-chloro-9-ethyl-6-(3-trifluoro-methyl-phenyl-amino)-9H-purine is obtained as a crystalline compound. This is filtered off and dried; m.p. 129° C.; FAB-MS: (M+H)$^+$=342; $R_f$=0.6 (CH$_2$Cl$_2$:methanol=9:1).

EXAMPLE 96

Analogously to Example 92, 6-(4-fluoro-phenyl-amino)-2-(2-hydroxy-ethyl-amino)-9-isopropyl-9H-purine is obtained as a crystalline compound from 0.2 g (0.52 mmol) of 2-chloro-9-isopropyl-6-(4-fluoro-phenyl-amino)-9H-purine in 1 ml of ethanolamine at 150° C. for 48 h; m.p. 139° C.; FARMS: (M+H)$^+$=331; $R_f$=0.45 (CH$_2$Cl$_2$:methanol=9:1).

The starting material is obtained as follows:

Stage 96.1: 2 g (10.6 mmol) of 2,6-dichloro-purine are stirred in 50 ml of n-butanol with 5.1 ml (52.9 mmol) of 4-fluoro-aniline at 70° C. for 10 h. The crystal mass which has precipitated out on cooling is the desired 2-chloro-6-(4-fluoro-phenyl-amino)-purine. This is filtered off and dried in vacuo. m.p.>250° C.; FAB-MS: (M+H)$^+$=264; $R_f$=0.5 (CH$_2$Cl$_2$:methanol=9:1).

Stage 96.2: A mixture comprising 1 g (3.3 mmol) of 2-chloro-6-(4-fluoro-phenyl-amino)-purine, 2.1 g (6.6 mmol) of caesium carbonate and 2 ml of isopropyl iodide is stirred in 32 ml of a mixture comprising dioxane, water and DMF in a ratio of 2:3:7 at 100° C. for 20 h. Thereafter, the reaction mixture is diluted with ethyl acetate and the organic phase is washed with water. After drying over sodium sulfate and removal of the solvent, the residue is chromatographed over silica gel (mobile phase: ethyl acetate:hexane=4:1). On concentration, 2-chloro-9-isopropyl-6-(4-fluoro-phenyl-amino)-9H-purine is obtained as a crystalline compound. m.p. 154° C.; FAB-MS: (M+H)$^+$=306; $R_f$=0.2 (ethyl acetate:hexane=4:1).

EXAMPLE 97

Analogously to Example 90, 2-(2-amino-ethyl-amino)-6-(4-fluoro-phenyl-amino)-9-isopropyl-9H-purine hydrochloride is obtained from 0.2 g (0.52 mmol) of 2-chloro-9-isopropyl-6-(4-fluoro-phenyl-amino)-9H-purine in 2.5 ml of ethylenediamine after 48 h at 75° C.; m.p.>250° C.; FAB-MS: (M+H)$^+$=330; $R_f$=0.7 (ethyl acetate:isopropanol:water: 22% aqueous ammonium hydroxide solution=40:60:15:10).

EXAMPLE 98

Analogously to Example 91, 2-(2-amino-ethyl-amino)-9-ethyl-6-(4-fluoro-phenyl-amino)-9H-purine hydrochloride is obtained in crystalline form from 0.24 g (0.68 mmol) of 2-chloro-9-ethyl-6-(4-fluoro-phenyl-amino)-9H-purine in 2.5 ml of ethylenediamine after 48 h at 75° C.; m.p.>250° C.; FAB-MS: (M+H)$^+$=316; $R_f$=0.6 (ethyl acetate:isopropanol:water:22% aqueous ammonium hydroxide solution=40:60:15:10).

The starting material is obtained as follows:

Stage 98.1: Analogously to Stage 96.2, 2-chloro-9-ethyl-6-(4-fluoro-phenyl-amino)-9H-purine is obtained in crystalline form from 1 g (3.3 mmol) of 2-chloro-6-(4-fluoro-phenyl-amino)-purine (prepared according to Stage 96.1), 1.7 g (5.2 mmol) of caesium carbonate and 2.1 ml of ethyl iodide with additional purification of the resulting compound by chromatography over silica gel (mobile phase: ethyl acetate:hexane=4:1); m.p. 184° C.; FAB-MS: (M+H)$^+$=292; $R_f$=0.8 (CH$_2$Cl$_2$:methanol=9:1).

EXAMPLE 99

Analogously to Example 92, 9-ethyl-6-(4-fluoro-phenyl-amino)-2-(2-hydroxy-ethyl-amino)-9H-purine is obtained from 0.24 g (0.68 mmol) of 2-chloro-9-ethyl-6-(4-fluoro-phenyl-amino)-9H-purine (prepared according to Stage 98.1) and 1 ml of ethanolamine after 48 h at 150° C., and is purified still further by chromatography over silica gel and then obtained as a crystalline mass; m.p. 152° C.; FAB-MS: (M+H)$^+$=317; $R_f$=0.3 (CH$_2$Cl$_2$:methanol 9:1).

EXAMPLE 100

Analogously to Example 92, 9-ethyl-2-(3-hydroxy-propyl-amino)-6-(3-trifluoromethyl-phenyl-amino)-9H-purine is obtained as colourless crystals from 0.2 g (0.58 mmol) of 2-chloro-9-ethyl-6-(3-trifluoromethyl-phenyl-amino)-9H-purine (prepared according to Stage 95.2) in 2 ml of 3-amino-1-propanol after 2 h at 140° C.; m.p. 136° C.; FAB-MS: (M+H)$^+$=381; $R_f$=0.3 (CH$_2$Cl$_2$:methanol 95:5).

EXAMPLE 101

Analogously to Example 90, 2-(2-amino-ethyl-amino)-9-isopropyl-6-(3-methoxy-phenyl-amino)-9H-purine is obtained in crystalline form from 0.2 g (0.63 mmol) of 2-chloro-9-isopropyl-6-(3-methoxy-phenyl-amino)-9H-purine in 4 ml of ethylenediamine after 16 h at 75° C.; m.p. 181° C.; FAB-MS: (M+H)$^+$=342; $R_f$=0.1 (CH$_2$Cl$_2$:methanol=7:3).

The starting material is obtained as follows:

Stage 101.1: 2 g (7.25 mmol) of 2-chloro-6-(3-methoxy-phenyl-amino)-purine (prepared according to Stage 26.1), 4.7 g (14.5 mmol) of caesium carbonate and 3.8 ml (38.2 mmol) of isopropyl iodide are stirred in 60 ml of a mixture comprising dioxane:water:DMF in a ratio of 9:1:1 at 60° C. for 6 h. Thereafter, the reaction mixture is diluted with ethyl acetate and the organic phase is washed with water and dried over sodium sulfate. After removal of the solvent, the residue is chromatographed over silica gel (mobile phase: $CH_2Cl_2$:methanol=9:1). The crystalline precipitate obtained on concentration is 2-chloro-9-isopropyl-6-(3-methoxy-phenyl-amino)-9H-purine; m.p. 101° C.; FAB-MS: $(M+H)^+$=318; $R_f$=0.8 ($CH_2Cl_2$:methanol=9:1).

EXAMPLE 102

0.15 g (0.4 mmol) of 2-chloro-9-isopropyl-6-(3-methoxy-phenyl-amino)-9H-purine (prepared according to Stage 101.1) and 23 mg (0.44 mmol) of hydrazine monohydrate are stirred in 1 ml of n-butanol/pyridine (4:1) at 70° C. for 6 h. The mixture is allowed to cool and is diluted with ethyl acetate. The organic phase is washed with water and dried over sodium sulfate. After removal of the solvent, the residue is dissolved in dioxane. The crystalline precipitate obtained after dropwise addition of 4 N HCl in dioxane, which is 2-hydrazino-6-(3-methoxy-phenyl-amino)-9-isopropyl-9H-purine hydrochloride, is filtered off and dried; m.p. 250° C.; FAB-MS: $(M+H)^+$=314; $R_f$=0.5 ($CH_2Cl_2$:methanol=95:5).

EXAMPLE 103

Analogously to Example 91, 2-(2-amino-ethyl-amino)-9-ethyl-6-(3-nitro-phenyl-amino)-9H-purine hydrochloride is obtained as a crystalline compound from 0.22 g (0.7 mmol) of 2-chloro-9-isopropyl-6-(4-nitro-phenyl-amino)-9H-purine in 3 ml of ethylenediamine after 2 h at 75° C.; m.p.>250° C.; FAB-MS: $(M+H)^+$=357; $R_f$=0.1 ($CH_2Cl_2$:methanol=9:1).

The starting material is obtained as follows:

Stage 103.1: 1.9 g (10 mmol) of 2,6-dichloro-purine are stirred in 40 ml of DMF/n-butanol (1:3) with 4.1 g (30 mmol) of 4-nitro-aniline at 130° C. for 24 h and the crystal mass which precipitates out on cooling is filtered off and dried in vacuo. 2-Chloro-6-(4-nitro-phenyl-amino)-purine is obtained; m.p.>270° C.; FAB-MS: $(M+H)^+$=291; $R_f$=0.6 ($CH_2Cl_2$:methanol=9:1).

Stage 103.2: A mixture comprising 0.87 g (3 mmol) of 2-chloro-6-(4-nitro-phenyl-amino)-purine, 0.15 g (4.5 mmol) of caesium carbonate and 1.8 ml (18 mmol) of isopropyl iodide is stirred in 22 ml of a mixture comprising dioxane:water:DMF in a ratio of 2:1:4 at 100° C. for 48 h. Thereafter, the reaction mixture is diluted with ethyl acetate and the organic phase is washed with water and dried over sodium sulfate. After removal of the solvent, the residue is chromatographed over silica gel (mobile phase: $CH_2Cl_2$:methanol=9:1). The crystalline precipitate obtained on concentration is filtered off and dried. 2-Chloro-9-isopropyl-6-(4-nitro-phenyl-amino)-9H-purine is obtained; m.p.>260° C.; FAB-MS: $(M+H)^+$=333; $R_f$=0.8 ($CH_2Cl_2$:methanol=9:1).

EXAMPLE 104

25 mg (0.1 mmol) of 2-(2-hydroxy-ethyl-amino)-6-thiomethyl-9-ethyl-9H-purine and 38 μl (0.3 mmol) of 4-amino-benzotrifluoride are dissolved in 2 ml of methylene chloride, and 52 mg (0.3 mmol) of 3-chloro-perbenzoic acid, dissolved in 3 ml of methylene chloride, are added dropwise at RT in the course of 1 h. The reaction mixture is stirred at RT for 3 h and diluted with ethyl acetate. The organic phase is washed with sat. aqueous sodium bicarbonate solution and brine and dried over sodium sulfate. After removal of the solvent, the residue is chromatographed over silica gel (mobile phase: methylene chloride:methanol=95:5). 9-Ethyl-2-(2-hydroxy-ethyl-amino)-6-(4-trifluoromethyl-phenyl-amino)-9H-purine is obtained as a crystalline compound; m.p. 191–192° C.; FAB-MS: $(M+H)^+$=367; $R_f$=0.5 (methylene chloride:methanol=9:1).

The starting material is obtained as follows:

Stage 104.1: 3 g (15.9 mmol) of 2,6-dichloro-purine are stirred in 15 ml of n-butanol with 2.4 g (31.8 mmol) of sodium methanethiolate at 100° C. for 1 h. The reaction mixture is cooled and diluted with ethyl acetate. The desired compound, 2-chloro-6-thiomethyl-purine, precipitates out as a crystalline compound by dropwise addition of 1 N HCl, and is filtered off and dried; m.p. 289° C.; FAB-MS: $(M+H)^+$=201; $R_f$=0.3 (ethyl aceate:hexane=4:1).

Stage 104.2: 0.6 g (3 mmol) of 2-chloro-6-thiomethyl-purine, 1.5 g (4.5 mmol) of caesium carbonate and 1.5 ml (18 mmol) of ethyl iodide are stirred in 30 ml of a mixture comprising dioxane:water:DMF in a ratio of 2:1:4 at RT for 16 h. Thereafter, the reaction mixture is diluted with ethyl acetate and washed with water. After the organic phase has been separated off, this is dried over sodium sulfate and concentrated. The desired compound, crystalline 2-chloro-9-ethyl-6-thiomethyl-9H-purine, is separated off from the by-product, 2-chloro-7-ethyl-6-thiomethyl-7H-purine, by chromatography over silica gel (mobile phase: methylene chloride:methanol=95:5); m.p. 119° C.; FAB-MS: $(M+H)^+$=229; $R_f$=0.8 (methylenechloride:methanol=9:1).

Stage 104.3: 0.2 g (0.9 mmol) of 2-chloro-9-ethyl-6-thiomethyl-9H-purine is stirred in 1 ml of ethanolamine at 105° C. for 18 h. After removal of the ethanolamine under a high vacuum, the residue is chromatographed over silica gel (mobile phase: methylene chloride:methanol=9:1) and the desired compound, 2-(2-hydroxy-ethyl-amino)-6-thiomethyl-9-ethyl-9H-purine, is isolated as a crystalline solid; m.p. 115° C.; FAB-MS: $(M+H)^+$=254; $R_f$=0.5 (methylene chloride:methanol=9:1).

The disubstituted compound, 2,6-di-(2-hydroxy-ethyl-amino)-9-ethyl-9H-purine, can be isolated as a by-product.

EXAMPLE 105

Analogously to Example 92, 9-ethyl-2-(2-hydroxy-ethyl-amino)-6-(3,5-di-trifluoromethyl-phenyl-amino)-9H-purine is obtained from 360 mg (0.6 mmol) of 2-(chloro-9-ethyl-6-(3,5-di-trifluoromethyl-phenyl-amino)-9H-purine in 2.03 ml (32 mmol) of ethanolamine after 21 h at 100° C. Purification is carried out by chromatography over silica gel (mobile phase: acetone:hexane=1:1). The substance is crystalline; m.p. 202° C.; FAB-MS: $(M+H)^+$=435; $R_f$=0.11 (ethyl acetate:hexane=4:1).

The starting material is obtained as follows:

Stage 105.1: Analogously to Stage 96.1, 2-chloro-6-(3,5-di-trifluoromethyl-phenyl-amino)-purine is obtained from 1.5 g (7.7 mmol) of 2,6-dichloro-purine and 1.9 g (7.78 mmol) in 45 ml of n-butanol after 13 h at 100° C. Purification is carried out by recrystallization from ethyl acetate/hexane. Colourless crystals are obtained; m.p. 265° C.; FAB-MS: $(M+H)^+$=382; $R_f$=0.26 (ethyl acetate:hexane=4:1).

Stage 105.2: Analogously to Stage 96.2, 2-chloro-9-ethyl-6-(3,5-di-trifluoromethyl-phenyl-amino)-9-H-purine is obtained from 1 g (2.36 mmol) of 2,6-chloro-6-(di-trifluoromethyl-phenyl-amino)-purine, 2.4 g (7.54 mmol) of caesium carbonate and 3 ml (37.6 mmol) of ethyl iodide after stirring at RT for 21 h in 60 ml of DMF/water (8:2) and 15 ml of dioxane. Purification is carried out by chromatography over silica gel (mobile phase: ethyl acetate:hexane=4:1) and recrystallization from t-butyl methyl ether. Colourless crystals are obtained; m.p. 158° C.; FAB-MS: (M+H)$^+$=410; $R_f$=0.47 (ethyl acetate:hexane=4:1).

EXAMPLE 106

Analogously to Example 92, 6-(4-chloro-3-trifluoromethyl-phenyl-amino)-9-ethyl-2-(2-hydroxy-ethyl-amino)-9H-purine is obtained from 340 mg (0.68 mmol) of 2-chloro-9-ethyl-6-(4-chloro-3-trifluoromethyl-phenyl-amino)-9H-purine in 2.03 ml of ethanolamine after 21 h at 65° C. Purification is carried out by chromatography over silica gel (mobile phase: acetone:hexane=1:1); m.p. 194° C.; FAB-MS: (M+H)$^+$=401; $R_f$=0.04 (ethyl acetate:hexane=4:1).

The starting material is obtained as follows:

Stage 106.1: Analogously to Stage 96.1, 2-chloro-6-(4-chloro-3-trifluoromethyl-phenyl-amino)-purine is obtained from 1.5 g (7.78 mmol) of 2,6-dichloro-purine and 1.6 g (7.78 mmol) of 5-amino-2-chloro-benzotrifluoride in 45 ml of n-butanol after 13 h at 100° C. Purification is carried out by trituration of the crude product in t-butyl methyl ether. Colourless crystals are obtained; m.p. 283° C.; FAB-MS: (M+H)$^+$=348; $R_f$=0.1 (ethyl acetate:hexane=4:1).

Stage 106.2: Analogously to Stage 96.2, 2-chloro-9-ethyl-6-(4-chloro-3-trifluoromethyl-phenyl-amino)-9H-purine is obtained from 400 mg (1.03 mmol) of 2-chloro-6-(4-chloro-3-trifluoromethyl-phenyl-amino)-purine, 1.1 g (3.3 mmol) of caesium carbonate and 1.37 ml (16.8 mmol) of ethyl iodide after 25 h at RT in 40 ml of DMF/water (8:2) and 10 ml of dioxane. Purification is carried out by recrystallization from t-butyl methyl ether. Colourless crystals are obtained; m.p. 167° C.; FAB-MS: (M+H)$^+$=376; $R_f$=0.2 (ethyl acetate:hexane=4:1).

EXAMPLE 107

Analogously to Example 92, 6-(4-benzyloxycarbonylamino-phenyl-amino)-9-ethyl-2-(2-hydroxy-ethyl-amino)-9H-purine is obtained from 1 g (2.36 mmol) of 2-chloro-9-ethyl-6-(4-benzyloxycarbonylamino-phenyl-amino)-9H-purine in 10 ml of ethanolamine after 2 h at 120° C. Purification is carried out by chromatography over silica gel (mobile phase: methylene chloride:methanol=9:1); m.p. 148° C.; FAB-MS: (M+H)$^+$=448; $R_f$=0.3 (methylene chloride:methanol=9:1).

The starting material is obtained as follows:

Stage 107.1: 5.4 g (50 mmol) of 1,4-phenylendiamine are dissolved in 100 ml of ethyl acetate, and 14.3 g (50 mmol) of dibenzyl dicarbonate in 20 ml of dioxane are added dropwise at RT in the course of 15 min. After the reaction mixture has been stirred at RT for 3 h, it is diluted with ethyl acetate and washed with 4 N NaOH and with water until neutral. After drying over sodium sulfate, some of the solvent is removed. The desired compound, 4-benzyloxycarbonylamino-aniline, crystallizes out by addition of diethyl ether/hexane (1:4); m.p. 85° C.; FAB-MS: (M+H)$^+$=243; $R_f$=0.3 (methylene chloride:methanol=97:3).

Stage 107.2: Analogously to Stage 96.1, the desired compound, 2-chloro-6-(4-benzyloxycarbonylamino-phenyl-amino)-purine, is obtained from 2.7 g (14 mmol) of 2,6-dichloro-purine and 4.4 g (18 mmol) of 4-benzyloxycarbonylamino-aniline in 42 ml of n-butanol:DMF (20:1) after 18 h at 50° C. The compound is crystalline. m.p.>320° C.; FAB-MS: (M+H)$^+$=395; $R_f$=0.3 (methylene chloride:methanol=9:1).

Stage 107.3: Analogously to Stage 96.2, 2-chloro-9-ethyl-6-(4-benzyloxycarbonylamino-phenyl-amino)-9H-purine is obtained from 2.5 g (6.3 mmol) of 2-chloro-6-(4-benzyloxycarbonylamino-phenyl-amino)-purine, 3.1 g (9.45 mmol) of caesium carbonate and 3.05 ml (37.8 mmol) of ethyl iodide after 16 h at RT in 40 ml of DMF/water/dioxane (2:1:4). Purification is carried out by chromatography over silica gel (mobile phase: ethyl acetate:hexane=4:1); m.p. 202° C.; FAB-MS: (M+H)$^+$=423; $R_f$=0.6 (methylene chloride:methanol=9:1).

EXAMPLE 108

0.45 g (1 mmol) of 2-(2-hydroxy-ethyl-amino)-6-(4-benzyloxycarbonylamino-phenyl-amino)-9-ethyl-9H-purine (prepared according to Example 107) are hydrogenated with 0.1 g of 10% Pd/C in 8 ml of methanol at RT for 5 h. The catalyst is filtered off, the residue on the filter is rinsed with dioxane/water (95:5) and the solvent is removed in vacuo. The desired compound, 6-(4-amino-phenyl-amino)-9-ethyl-2-(2-hydroxy-ethyl-amino)-9H-purine, can be isolated in crystalline form by this procedure; m.p. 210° C.; FAB-MS: (M+H)$^+$=314; $R_f$=0.15 (methylene chloride:methanol=9:1).

EXAMPLE 109

63 mg (0.2 mmol) of 2-(2-hydroxy-ethyl-amino)-6-(4-amino-phenyl-amino)-9-ethyl-9H-purine (prepared according to Example 108) are dissolved in 1 ml of pyridine and treated with 139 µl (1 mmol) of trifluoroacetic anhydride at RT. The reaction mixture is stirred at RT for 30 minutes. It is diluted with ethyl acetate and washed with water. On concentration, the desired compound, 9-ethyl-2-(2-hydroxy-ethyl-amino)-6-(4-trifluoro-acetylamino-phenyl-amino)-9H-purine, is obtained in crystalline form; m.p. 185° C.; FAB-MS: (M+H)$^+$410; $R_f$=0.15 (methylene chloride:methanol=9:1).

EXAMPLE 110

62 mg (0.2 mmol) of 6-(4-amino-phenyl-amino)-9-ethyl-2-(2-hydroxy-ethyl-amino)-9H-purine (prepared according to Example 108), 0.18 g (0.4 mmol) of (benzotriazol-1-yloxy)-tris-(dimethylamino)-phosphonium hexafluorophosphate (BOP), 54 mg (0.4 mmol) of 1-hydroxybenzotriazole (HOBT) and 68 µl of diisopropylamine are stirred in 6 ml of dimethylacetamide at RT for 5 min and then treated with 63 mg (0.4 mmol) of 3-chlorobenzoic acid. After the reaction mixture has been stirred at RT for 30 min, it is diluted with ethyl acetate and washed with water. The crude product is purified by chromatography over silica gel (mobile phase: methylene chloride:methanol=9:1). 6-(4-[3-Chloro-benzoyl-amino]-phenyl-amino)-9-ethyl-2-(2-hydroxy-ethyl-amino)-9H-purine is obtained; FAB-MS: (M+H)$^+$=452; $R_f$=0.45 (methylene chloride:methanol=9:1).

EXAMPLE 111

The following compounds are obtained analogously to the processes described in this text:

a1) 2-(cis-2-Amino-cyclohexyl-amino)-9-ethyl-6-(3-trifluoromethyl-phenylamino)-9H-purine
a2) 9-Ethyl-2-[(R)-1-hydroxy-but-2-yl-amino]-6-(3-trifluoromethyl-phenyl-amino)-9H-purine
a3) 9-Ethyl-2-(trans-4-hydroxy-cyclohexyl-amino)-6-(3-trifluoromethyl-phenyl-amino)-9H-purine
a4) 2-(trans-4-Amino-cyclohexyl-amino)-9-ethyl-6-(3-trifluoromethyl-phenyl-amino)-9-H-purine
a5) 2-(2-Amino-ethyl-amino)-9-ethyl-6-(3-trifluoromethyl-phenylamino)-9H-purine
a6) 2-(cis-4-Amino-cyclohexyl-amino)-9-ethyl-6-(3-trifluoromethyl-phenyl-amino)-9H-purine
b1) 2-(cis-2-Amino-cyclohexyl-amino)-6-[(4-fluoro-phenylamino)-9-ethyl-9H-purine
b2) 6-(4-Fluoro-phenyl-amino)-9-ethyl-2-[(R)-1-hydroxy-but-2-yl-amino]-9H-purine
b3) 6-(4-Fluoro-phenyl-amino)-9-ethyl-2-(trans-4-hydroxy-cyclohexyl-amino)-9H-purine
b4) 2-(trans-4-Amino-cyclohexyl-amino)-6-(4-fluoro-phenyl-amino)-9-ethyl-9H-purine
b5) 2-(2-Amino-ethyl-amino)-6-(4-fluoro-phenylamino)-9-ethyl-9H-purine
b6) 2-(cis-4-Amino-cyclohexyl-amino)-6-(4-fluoro-phenyl-amino)-9-ethyl-9H-purine
c1) 2-(cis-2-Amino-cyclohexyl-amino)-9-ethyl-6-(4-trifluoromethyl-phenylamino)-9H-purine
c2) 9-Ethyl-2-[(R)-1-hydroxy-but-2-yl-amino]-6-(4-trifluoromethyl-phenyl-amino)-9H-purine
c3) 9-Ethyl-2-(trans-4-hydroxy-cyclohexyl-amino)-6-(4-trifluoromethyl-phenyl-amino)-9H-purine
c4) 2-(trans-4-Amino-cyclohexyl-amino)-9-ethyl-6-(4-trifluoromethyl-phenyl-amino)-9H-purine
c5) 2-(2-Amino-ethyl-amino)-9-ethyl-6-(4-trifluoromethyl-phenylamino)-9H-purine
c6) 2-(cis-2-Amino-cyclohexyl-amino)-9-ethyl-6-(4-trifluoromethyl-phenyl-amino)-9H-purine
d1) 2-(cis-2-Amino-cyclohexyl-amino)-6-(3-fluoro-phenylamino)-9-ethyl-9H-purine
d2) 6-(3-Fluoro-phenyl-amino)-9-ethyl-2-[(R)-1-hydroxy-but-2-yl-amino]-9H-purine
d3) 6-(3-Fluoro-phenyl-amino)-9-ethyl-2-(trans 4-hydroxy-cyclohexyl-amino)-9H-purine
d4) 2-(trans-4-Amino-cyclohexyl-amino)-6-(3-fluoro-phenyl-amino)-9H-purine
d5) 2-(2-Amino-ethyl-amino)-6-(3-fluoro-phenylamino)-9-ethyl-9H-purine
d6) 2-(cis-4-Amino-cyclohexyl-amino)-6-(3-fluoro-phenyl-amino)-9-ethyl-9H-purine
e1) 2-(cis-2-Amino-cyclohexyl-amino)-9-ethyl-6-(3-methoxy-phenylamino)-9H-purine
e2) 9-Ethyl-2-[(R)1-hydroxy-but-2-yl-amino]-6-(3-methoxy-phenyl-amino)-9H-purine
e3) 9-Ethyl-2-(trans-4-hydroxy-cyclohexyl-amino)-6-(3-methoxy-phenyl-amino)-9H-purine
e4) 2-(trans-4-Amino-cyclohexyl-amino]-9-ethyl-6-(3-methoxy-phenyl-amino)-9H-purine
e5) 2-(2-Amino-ethyl-amino)-9-ethyl-6-(3-methoxy-phenylamino)-9H-purine
e6) 2-(cis-4-Amino-cyclohexyl-amino)-9-ethyl-6-(3-methoxy-phenyl-amino)-9H-purine
f1) 2-(cis-2-Amino-cyclohexyl-amino)-6-(3-cyano-phenylamino)-9-ethyl-9H-purine
f2) 6-(3-Cyano-phenyl-amino)-9-ethyl-2-[(R)-1-hydroxy-but-2-yl-amino]-9H-purine
f3) 6-(3-Cyano-phenyl-amino)-9-ethyl-2-(trans-4-hydroxy-cyclohexyl-amino)-9H-purine
f4) 2-(trans-4-Amino-cyclohexyl-amino)-6-(3-cyano-phenyl-amino)-9-ethyl-9H-purine
f5) 2-(2-Amino-ethyl-amino)-6-(3-cyano-phenylamino)-9-ethyl-9H-purine
f6) 2-(cis-4-Amino-cyclohexyl-amino)-6-(3-cyano-phenyl-amino)9-ethyl-9H-purine
g1) 2-(cis-2-Amino-cyclohexyl-amino)-6-(4-amino-phenylamino)-9-ethyl-9H-purine
g2) 6-(4-Amino-phenyl-amino)-9-ethyl-2-[(R)-1-hydroxy-but-2-yl-amino]-9H-purine
g3) 6-(4-Amino-phenyl-amino)-9-ethyl-2-(trans-4-hydroxy-cyclohexyl-amino)-9H-purine
g4) 2-(trans-4-Amino-cyclohexyl-amino)-6-(4-amino-phenyl-amino)-9-ethyl-9H-purine
g5) 2-(2-Amino-ethyl-amino)-6-(4-amino-phenylamino)-9-ethyl-9H-purine
g6) 2-(cis-4-Amino-cyclohexyl-amino)-6-(4-amino-phenyl-amino)-9-ethyl-9H-purine
h1) 2-(cis-2-Amino-cyclohexyl-amino)-6-(4-chloro-3-trifluoromethyl-phenylamino)-9-ethyl-9H-purine
h2) 6-(4-Chloro-3-trifluoromethyl-phenyl-amino)-9-ethyl-2-[(R)-1-hydroxy-but-2-yl-amino]-9H-purine
h3) 6-(4-Chloro-3-trifluoromethyl-phenyl-amino)-9-ethyl-2-(trans-4-hydroxy-cyclohexyl-amino)-9H-purine
h4) 2-(trans-4-Amino-cyclohexyl-amino)-6-(4-chloro-3-trifluoromethyl-phenyl-amino)-9-ethyl-9H-purine
h5) 2-(2-Amino-ethyl-amino)-6-(4-chloro-3-trifluoromethyl-phenylamino)-9-ethyl-9H-purine
h6) 2-(cis-4-Amino-cyclohexyl-amino)-6-(4-chloro-3-trifluoromethyl-phenyl-amino)-9-ethyl-9H-purine
i1) 2-(cis-2-Amino-cyclohexyl-amino)-9-ethyl-6-(3,5-di-trifluoromethyl-phenylamino)-9H-purine
i2) 9-Ethyl-2-[(R)-1-hydroxy-but-2-yl-amino]-6-(3,5-di-trifluoromethyl-phenyl-amino)-9H-purine
i3) 9-Ethyl-2-(trans-4-hydroxy-cyclohexyl-amino)-6-(3,5-di-trifluoromethyl-phenyl-amino)-9H-purine
i4) 2-(trans-4-Amino-cyclohexyl-amino)-9-ethyl-6-(3,5-di-trifluoromethyl-phenyl-amino)-9H-purine
i5) 2-(2-Amino-ethyl-amino)-9-ethyl-6-(3,5-di-trifluoromethyl-phenylamino)-9H-purine
i6) 2-(cis-4-Amino-cyclohexyl-amino)-9-ethyl-6-(3,5-di-trifluoromethyl-phenyl-amino)-9H-purine
k) 9-Ethyl-2-[2-(2-hydroxyethyl-hexahydropyridazino)-6-(3-chloro-phenyl-amino)-9H-purine
l) 9-Ethyl-2-[2-(2-cyanoethyl-hexahydropyridazino)-6-(3-chloro-phenyl-amino)-9H-purine
m) 2-[2-(3 Aminopropyl-hexahydropyridazino)-6-(3-chloro-phenyl-amino)-9-ethyl-9H-purine
n) 9-Ethyl-2-[(R)-1-amino-but-2-yl-amino]-6-(3-chloro-phenyl-amino)-9H-purine
o) 6-(3-Chloro-phenyl-amino)-9-ethyl-2-[2-guanidino-ethylamino]-9H-purine
p) 6-(3-Chloro-phenyl-amino)-9-ethyl-2-guanidino-9H-purine and
q) 6-(3-Chloro-phenyl-amino)-9-ethyl-2-(cis-2-guanidino-cyclohexyl-amino)-9H-purine.

What is claimed is:

1. A compound of the formula II

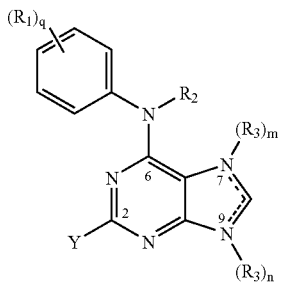

in which q is 1–5, $R_1$ is halogen; lower alkyl; hydroxyl; lower alkanoyloxy; lower alkoxy which is unsubstituted or substituted by hydroxyl, lower alkoxy or carboxyl; a radical of the formula —O(—CH$_2$—CH$_2$—O)$_t$—R$_6$, in which t is 2–5 and $R_6$ is hydrogen or lower alkyl; carboxyl; lower alkoxycarbonyl; piperazin-1-yl-carbonyl; carbamoyl; N-lower alkyl-carbamoyl which is unsubstituted in the lower alkyl moiety or substituted by hydroxyl or amino; N,N-di-lower alkyl-carbamoyl; cyano; nitro; amino; lower alkanoylamino; lower alkylamino; N,N-di-lower alkylamino; aminosulfonyl or trifluoromethyl, where, if more than one radical $R_1$ is present in the molecule, these can be identical or different from one another, $R_2$ is hydrogen, carbamoyl or N-lower alkyl-carbamoyl, m and n are each 0 or 1, where m is 0 if n is 1 and m is 1 if n is 0, dashed lines represent a single bond which is located between N-7 and C-8 if m is 0 and located between C-8 and N-9 if m is 1, $R_3$ is lower alkyl or phenyl which are unsubstituted or in each case substituted by hydroxyl, lower alkoxy, amino, lower alkylamino or N,N-di-lower alkylamino and Y is a suitable leaving group, it being possible for free functional groups present therein to be protected by easily detachable protective groups, or a salt thereof.

* * * * *